(12) United States Patent
Varley et al.

(10) Patent No.: US 12,042,931 B2
(45) Date of Patent: Jul. 23, 2024

(54) MECHANICAL HAND

(71) Applicant: COVVI Limited, Harrogate (GB)

(72) Inventors: Edward William Varley, Leeds (GB); Simon David Taylor, Leeds (GB)

(73) Assignee: COVVI LIMITED, Harrogate (GB)

( * ) Notice: Subject to any disclaimer, the term of this patent is extended or adjusted under 35 U.S.C. 154(b) by 741 days.

(21) Appl. No.: 17/278,952

(22) PCT Filed: Sep. 13, 2019

(86) PCT No.: PCT/GB2019/052565
§ 371 (c)(1),
(2) Date: Mar. 23, 2021

(87) PCT Pub. No.: WO2020/065265
PCT Pub. Date: Apr. 2, 2020

(65) Prior Publication Data
US 2022/0048208 A1    Feb. 17, 2022

(30) Foreign Application Priority Data
Sep. 25, 2018  (GB) ..................................... 1815634

(51) Int. Cl.
*A61F 2/58*     (2006.01)
*A61F 2/50*     (2006.01)
(Continued)

(52) U.S. Cl.
CPC ............... *B25J 15/10* (2013.01); *A61F 2/583* (2013.01); *A61F 2002/5079* (2013.01);
(Continued)

(58) Field of Classification Search
CPC .... B25J 17/02; B25J 17/0208; B25J 17/0233; B25J 17/0241; A61F 2/583; A61F 2/585; A61F 2002/5079
See application file for complete search history.

(56) References Cited

U.S. PATENT DOCUMENTS 3,824,674 A * 7/1974 Inoyama .................. G05D 3/20
                                                                  901/45
8,795,387 B1 * 8/2014 Razink .................... A61F 2/585
                                                                  623/62
(Continued)

FOREIGN PATENT DOCUMENTS

AU            527645 B2    3/1983

OTHER PUBLICATIONS

Intellectual Property Office, Great Britain Search Report for British Patent Application No. 1815634.9, Mar. 20, 2019, (5 pages), South Wales, United Kingdom.
(Continued)

*Primary Examiner* — Dean J Kramer
(74) *Attorney, Agent, or Firm* — Alston & Bird LLP

(57) ABSTRACT

The present application describes apparatus for supporting a mechanical hand, comprising a support member (200) pivotally coupled at a hinge axis (604) to a mounting member (700); and at least one leaf spring (707) configured to resist movement of the support member about the hinge axis. Apparatus for supporting a mechanical hand, comprising a lock arrangement (750) to lock the support member with respect to the mounting member in a rotational position about the hinge axis is also described.

20 Claims, 40 Drawing Sheets

(51) Int. Cl.
  *B25J 15/10*    (2006.01)
  *B25J 17/02*    (2006.01)
  *A61F 2/70*     (2006.01)
  *A61F 2/76*     (2006.01)

(52) U.S. Cl.
  CPC ... *A61F 2002/587* (2013.01); *A61F 2002/704* (2013.01); *A61F 2002/7625* (2013.01); *B25J 17/02* (2013.01)

(56) References Cited

U.S. PATENT DOCUMENTS

| | | | |
|---|---|---|---|
| 8,900,327 B2 * | 12/2014 | Bertels | A61F 2/585 623/61 |
| 9,469,036 B1 | 10/2016 | Kozlowski et al. | |
| 2007/0173955 A1 | 7/2007 | Archer et al. | |
| 2008/0269907 A1 | 10/2008 | Puchhammer | |
| 2017/0281368 A1 * | 10/2017 | Gill | A61F 2/588 |
| 2018/0036145 A1 | 2/2018 | Jury et al. | |

OTHER PUBLICATIONS

International Searching Authority, International Search Report and Written Opinion for International Application No. PCT/GB2019/052565, Mar. 5, 2020, (14 pages), European Patent Office, Rijswijk, Netherlands.

Scarcia, Umberto et al. "Modeling, Design, and Experimental Evaluation of Rotational Elastic Joints For Underactuated Robotic Fingers," *2017 IEEE-RAS 17th International Conference On Humanoid Robotics (Humanoids)*, Nov. 15-17, 2017, pp. 353-358, Birmingham, United Kingdom. XP033291609.

Choi, Wonje et al. "Low Stiffness Design and Hysteresis Compensation Torque Control Of SEA For Active Exercise Rehabilitation Robots," *Autonomous Robots*, Springer, Jul. 8, 2016, (22 pages). DOI: 10.1007/s10514-016-9591-z. XP036203826.

* cited by examiner

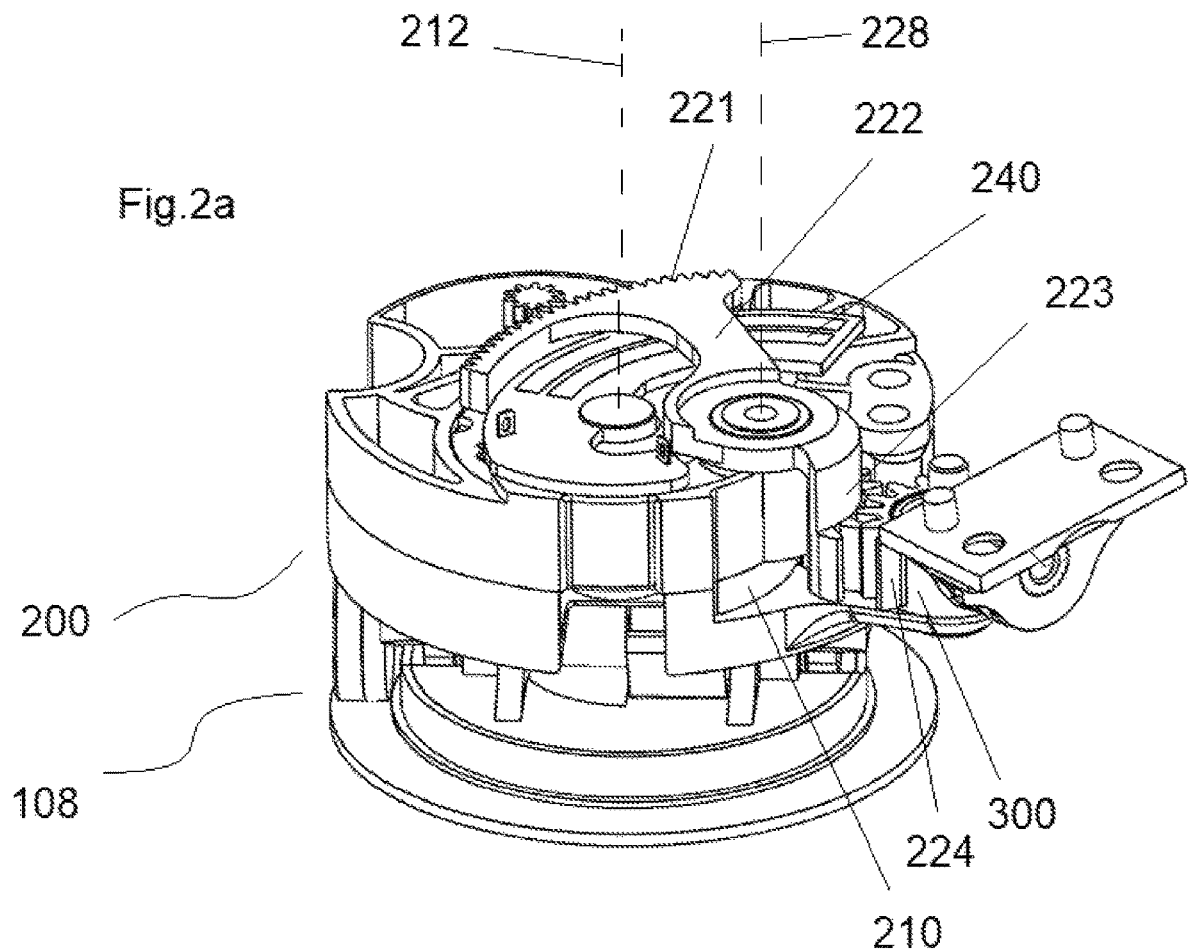

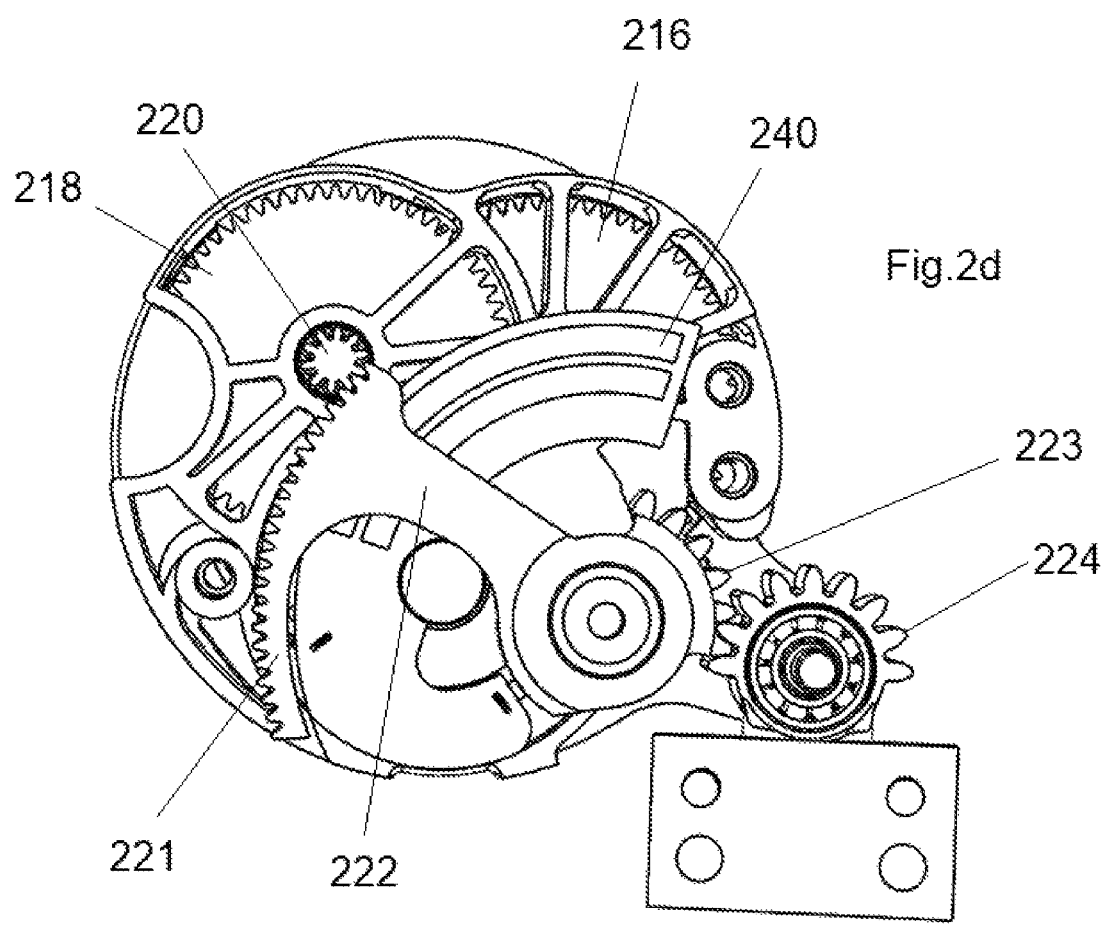

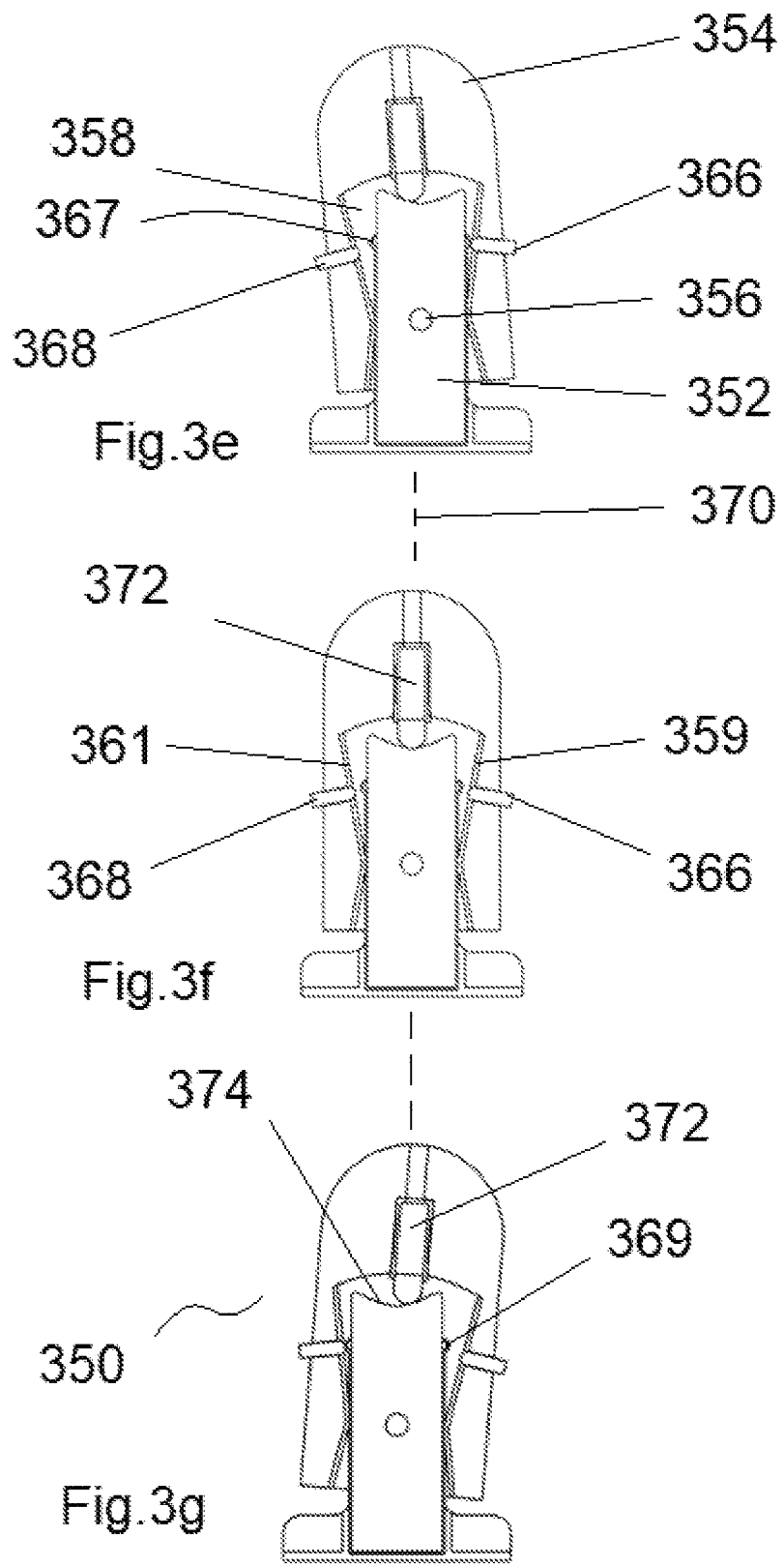

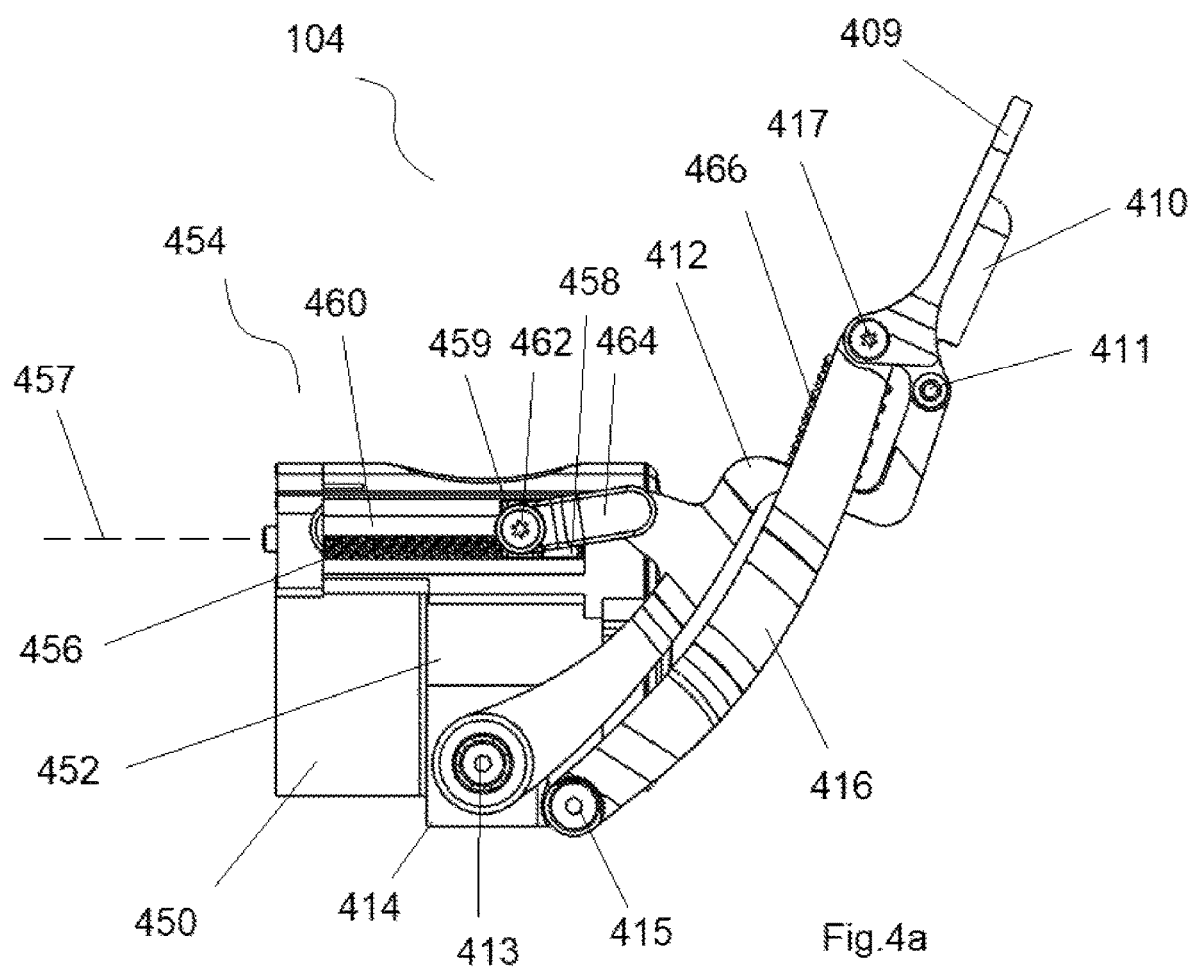

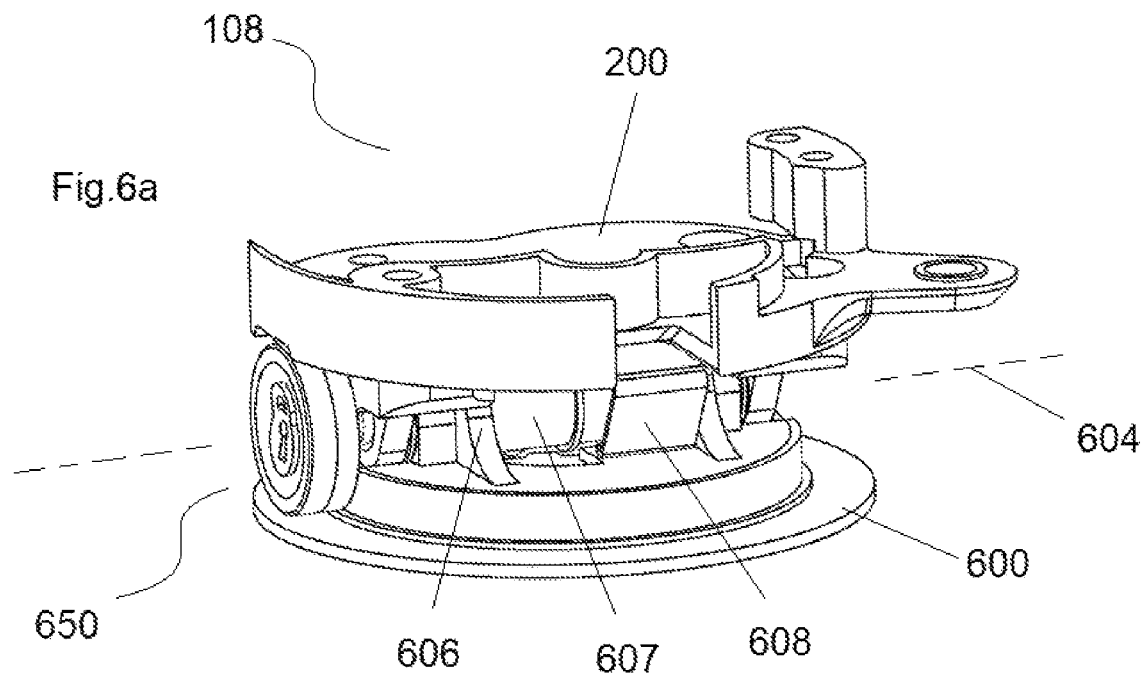
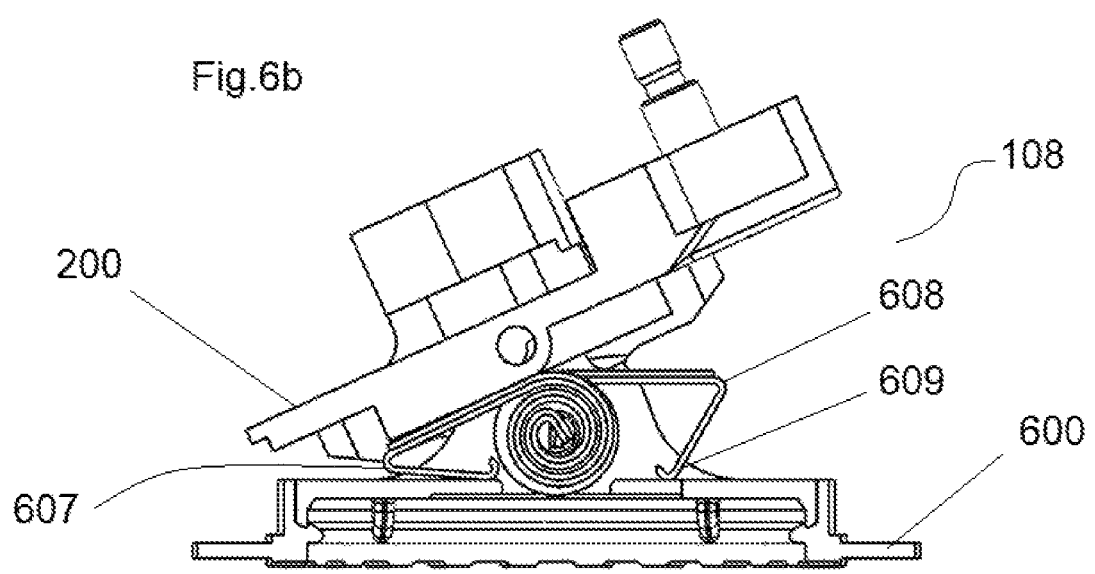

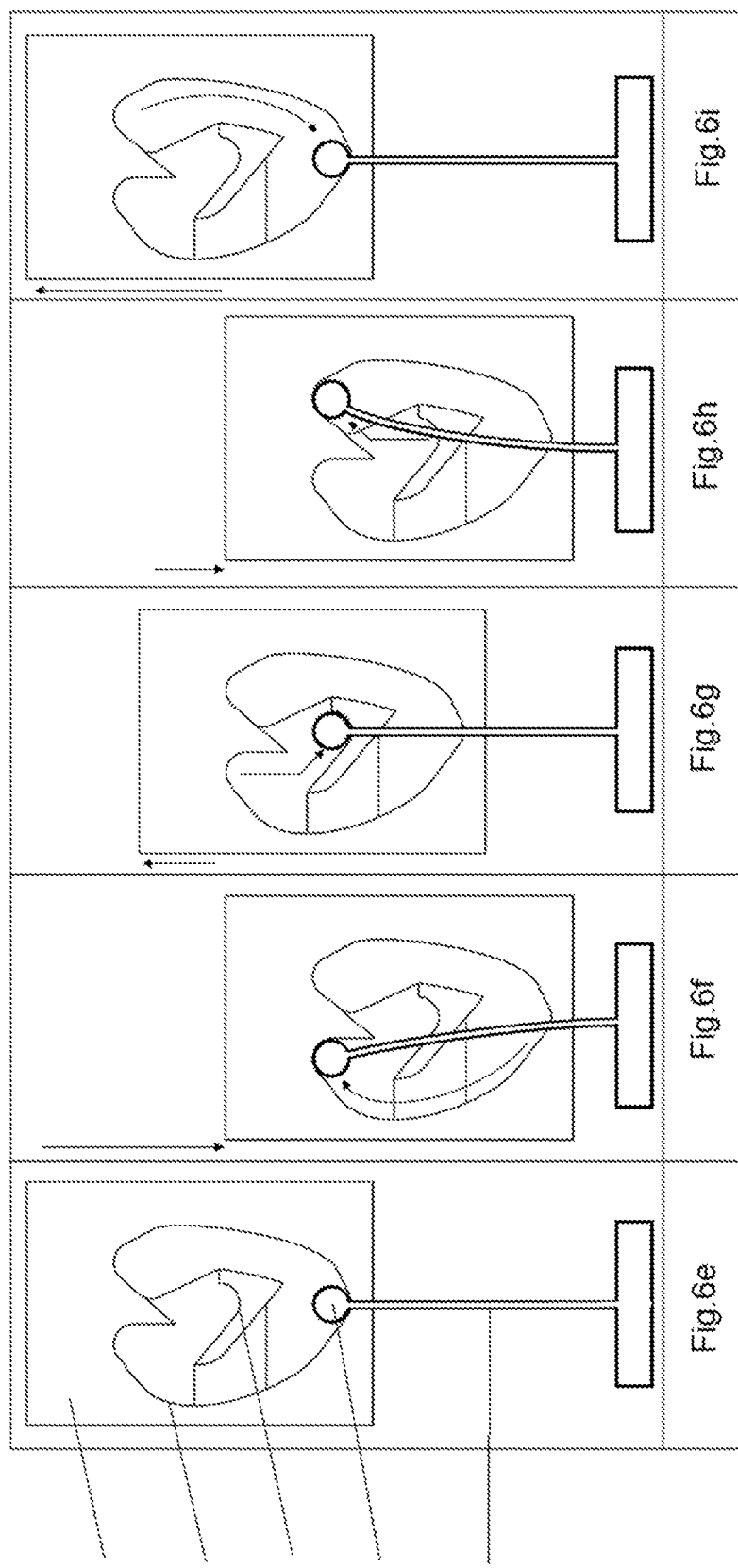

MECHANICAL HAND

CROSS REFERENCE TO RELATED APPLICATIONS

This application is a National Stage Application, filed under 35 U.S.C. 371, of International Application No. PCT/GB2019/052565, filed Sep. 13, 2019, which international application claims priority to and the benefit of United Kingdom Application No. 1815634.9, filed Sep. 25, 2018; the contents of both of which as are hereby incorporated by reference in their entireties.

BACKGROUND

Related Field

The present invention relates to mechanical hands such as for a robot or a prosthetic hand for a human. In particular, but not exclusively, the present invention relates to a prosthetic hand having improved functionality and operation.

Description of Related Art

A conventional prosthetic hand is typically controlled by a plurality of electrodes located on a user's residual limb which detect electrical signals generated by the user's muscles and send corresponding signals to a controller of the prosthetic hand. The controller actuates motors in response to the received signals which in turn drive motors to move fingers of the prosthetic hand. The signals are typically mapped to open (extend) and close (flex) the fingers relative to a palm portion of the hand.

Some devices also provide an adjustable thumb offering selectable opposed or non-opposed thumb positions. The opposed thumb position is when the thumb is facing, i.e. opposite, the fingers to allow 'pinch', 'tripod', 'power', 'hook' and 'trigger' grips, for example. The thumb may be manually moved by the user to either engage with the index finger only (pinch grip) or with the index and middle fingers (tripod grip) when in a closed 'opposed' configuration. Such grips may be used for picking up and manipulating small objects. With the thumb in the opposed position, a 'power' grip is where the fingers, followed by the thumb, close onto an object and may be used for clenching a ball or the like. A 'hook' grip is a partially closed 'power grip' for carrying a briefcase or the like. A 'trigger' grip may be used for operating the trigger of a spray bottle, for example, wherein the bottle is gripped between the thumb and the middle, ring and little fingers and the index fingers closes to operate the trigger of the bottle. The non-opposed thumb position is when the thumb is facing in a perpendicular direction to the fingers, i.e. in line with the palm portion, to allow 'key', 'finger point', 'mouse' and 'column' grips, for example. The 'key' grip is where the fingers are partially closed relative to the palm portion and the thumb closes on the side of the index finger. Such a grip may be used to hold a spoon or the like. The 'finger point' grip is where the ring, middle and little fingers are closed relative to the palm portion, the index finger is outstretched and the thumb is closed against the middle finger. Such a grip may be used to press a doorbell or type on a keyboard. The 'mouse' grip is where the thumb and little finger engage a computer mouse and the index finger is used to operate the mouse button. The 'column' grip is where the thumb is closed relative to the palm portion and the fingers are closed over the thumb. Such a grip may be used to push heavy objects or when getting dressed to avoid the thumb snagging on clothing.

However, the user must use their other hand to manually move the thumb of the prosthetic hand into the opposed or non-opposed position depending on the desired grip pattern. This takes effort and time, is not very discrete, and it can be difficult to tailor the position, sensing and index strength for a specific user, particularly in view of the many different requirements and environments for the prosthetic hand across different users and in different countries. Furthermore, the two thumb rotation positions offer limited grip choice and the force required to move the thumb between the opposed and non-opposed positions is relatively high which can undesirably cause the prosthetic hand to rotate about the wrist connection relative to the residual limb or knock the object to be gripped.

Electrically-controlled prosthetic hands broadly fall into two categories; robust 'myo' electrically-controlled terminal devices, and compliant multi-articulated devices that more accurately resemble a human hand. To achieve a high grip strength with the capability of rapid movement, the basic myo hands often include an automatic two speed gearbox. The extra dexterity provided by the multi-articulated hands typically comes with the compromise that they produce a reduced grip strength.

Traditionally actuators to drive a thumb have been mounted within the thumb body, either driving a worm gear around a static worm wheel or alternatively a linkage design with a leadscrew nut being pulled in the axis of the thumb and the mounting to cause the thumb to rotate forwards and backwards. Both these designs are limited to size of the actuators which can be accommodated within the thumb, which in turn limits grip force. Additionally, the line of action by these small motors relative to the direction of required grip force also significantly reduces the efficiency of the thumb.

Furthermore, traditionally motors have either been located in the fingers or mounted in the palm, with the motor parallel to the leadscrew actuator. Multi-articulated hands with the motor mounted in the fingers moves the centre of gravity away from the user, resulting in an increased moment around the socket attachment point and thus increases the potential for discomfort and also limits the power of the motor which can be fitted, resulting in a relatively weak hand. Multi-articulated hands with the motor mounted in the palm, and in parallel with a leadscrew actuator, enables the use of relatively powerful actuators, but results in an unnaturally deep palm section.

The ability for a prosthetic hand to be able to passively flex and extend is particularly desirable to allow a user to bend the wrist and orient the hand in a desired position to efficiently use an object they are gripping, whilst minimising excessive shoulder compensation. Allowing the hand to flex towards the user and lock in a desired position is particularly desirable when moving the prosthetic hand to the user's face. Conventionally, the limited space available has prevented the addition of a function attempting to provide one or more of these benefits such that, for example, a flex wrist function is completely omitted, particularly for relatively small limbs, or it may be a flex function relying on manual positioning. This is further compounded by the fact a user with a relatively long remnant limb may not have sufficient available length to allow the fitting of a hand and a flex wrist. An additional issue is the locking mechanism can be difficult for a user to activate and deactivate.

BRIEF SUMMARY

It is an aim of certain embodiments of the present invention to provide a prosthetic hand having improved functionality and operation.

It is an aim of certain embodiments of the present invention to provide a prosthetic hand that is relatively quick and easy to operate, particularly in terms of selecting a desired grip from a variety of different selectable grips.

It is an aim of certain embodiments of the present invention to provide a prosthetic hand configured to maximise the number of different selectable grip configurations.

It is an aim of certain embodiments of the present invention to provide a prosthetic hand that is accurate, consistent, non-complex, and relatively quick to calibrate.

It is an aim of certain embodiments of the present invention to provide a method of operating a prosthetic hand to select a desired grip from a variety of different grip configurations for the prosthetic hand to adopt for a particular application.

It is an aim of certain embodiments of the present invention to provide a prosthetic hand that is able to produce grip forces similar to that of a 'myo' electrically-controlled terminal device, whilst retaining the dexterity and compliant gripping of a multi-articulated hand.

It is an aim of certain embodiments of the present invention to provide a prosthetic hand having a relatively compact finger and/or thumb drive assembly.

It is an aim of certain embodiments of the present invention to provide a prosthetic hand including a relatively powerful actuator mounted in the palm, but with an inline actuation system which mounts the motor relatively close to the wrist to thereby ensure a centre of gravity of the device is relatively close to the user's body and patient fatigue is reduced.

It is an aim of certain embodiments of the present invention to provide a prosthetic hand including a relatively short and compact wrist assembly which allows automatic flex functionality, such as when the hand is bent backwards on impact with an object or the like.

It is an aim of certain embodiments of the present invention to provide a prosthetic hand including a wrist assembly which provides a non-complex and compact locking/unlocking function to allow the user to efficiently lock the hand in a desired orientation with respect to the limb socket.

According to a first aspect of the present invention there is provided apparatus for supporting a mechanical hand, comprising:
  a support member pivotally coupled at a hinge axis to a mounting member; and
  at least one leaf spring configured to resist movement of the support member about the hinge axis.

Optionally, the at least one leaf spring is configured to urge the support member towards a neutral equilibrium position with respect to the mounting member.

Optionally, the at least one leaf spring comprises a first leaf spring configured to resist movement of the support member in a first direction about the hinge axis, and a second leaf spring configured to resist movement of the support member in a second direction about the hinge axis, the second direction being opposed to the first direction.

Optionally, each spring is configured such that both springs engage the mounting member when the support member is in the neutral equilibrium position.

Optionally, the at least one leaf spring comprises an elongate main portion coupled to the support portion and at least one elongate leg portion extending from the main portion and engageable with the mounting member to provide a reaction force when the support member is forced to move about the hinge axis.

Optionally, the leg portion defines a first angle with respect to a plane of the main portion which is around 5-85 degrees.

Optionally, the leg portion is coupled to the main portion by an intermediate portion which defines a second angle with the respect to the plane of the main portion which is greater than the first angle.

Optionally, the at least one leaf spring comprises a plurality of unconnected layers.

Optionally, the at least one leaf spring is a linear leaf spring.

Optionally, the apparatus comprises a lock arrangement to lock the support member with respect to the mounting member in a rotational position about the hinge axis.

Optionally, the lock arrangement comprises a locking button to move a locking element to the locked position from an unlocked position, and vice versa.

According to a second aspect of the present invention there is provided apparatus for supporting a mechanical hand, comprising:
  a support member pivotally coupled at a hinge axis to a mounting member; and
  a lock arrangement to lock the support member with respect to the mounting member in a rotational position about the hinge axis,
  wherein the lock arrangement comprises a locking element selectively movable from an unlocked position to a locked position, and vice versa, by a locking button.

Optionally, the lock arrangement is configured to move the locking element to and from the locked position by applying a force to the lock button in a first direction.

Optionally, the locking button is urged in a second direction opposed to the first direction by at least one first resilient member.

Optionally, the at least one first resilient member comprises a first compression spring.

Optionally, the locking element is urged in the second direction by a second resilient member.

Optionally, the second resilient member comprises a second compression spring.

Optionally, the lock arrangement comprises a driving cam member coupled to the locking button, and a driven cam member coupled to the locking element, wherein the cam members are configured such that a translation of the driving cam member causes the driven cam member to rotate about a locking axis of the locking element when the cam members are engaged.

Optionally, the driving cam member is rotationally constrained by at least one rail element along which the driving cam member is translatable.

Optionally, the driven cam member is rotatable about the locking axis with respect to the locking element and rotationally constrainable by the at least one rail element along which the driven cam member is translatable.

Optionally, the at least one rail element comprises a tapered end region for engagement with a cam surface of the driven cam element to rotatably urge the driven cam member about the locking axis when axially urged against the tapered end region.

Optionally, the locking element is selectively engageable with at least one locking aperture when in the locked position.

Optionally, the locking aperture is selectable from a plurality of spaced apart locking apertures each corresponding to a different rotational position of the support member with respect to the mounting member about the hinge axis.

Optionally, the locking apertures extend into an outer edge of at least one lug and the locking element comprises at least one recess for receiving the outer edge of the lug to allow the locking element to pass over the locking apertures when the locking element is in the unlocked position.

Optionally, the apparatus comprises at least one spring configured to resist movement of the support member with respect to the mounting member about the hinge axis when the locking element is in the unlocked position.

According to a third aspect of the present invention there is provided a mechanical hand comprising apparatus according to any preceding claim.

BRIEF DESCRIPTION OF THE FIGURES

Certain embodiments of the present invention will now be described with reference to the accompanying drawings in which:

FIG. 2a illustrates a thumb rotation mechanism of the hand of FIGS. 1a to 1f;

FIG. 2b illustrates an exploded view of a gearbox of the thumb rotation mechanism of FIG. 2a;

FIG. 2d illustrates a plan view of the thumb rotation mechanism with the thumb in the opposed position;

FIG. 3b illustrates a section through the thumb rocker mechanism of FIG. 3a;

FIGS. 3e to 3g illustrate an alternative embodiment of the thumb rocker mechanism;

FIGS. 4a and 4b illustrate the thumb assembly of the hand of FIGS. 1a to 1f in an extended state;

FIG. 6a illustrates a wrist assembly of the hand of FIGS. 1a to 1f;

FIG. 6b illustrates a side cross sectional view of the wrist assembly of FIG. 6a in a flexed state;

FIGS. 6e to 6i illustrate an actuation mechanism of the lock arrangement of FIGS. 6c and 6d;

DETAILED DESCRIPTION OF VARIOUS EMBODIMENTS

Figure 1A:
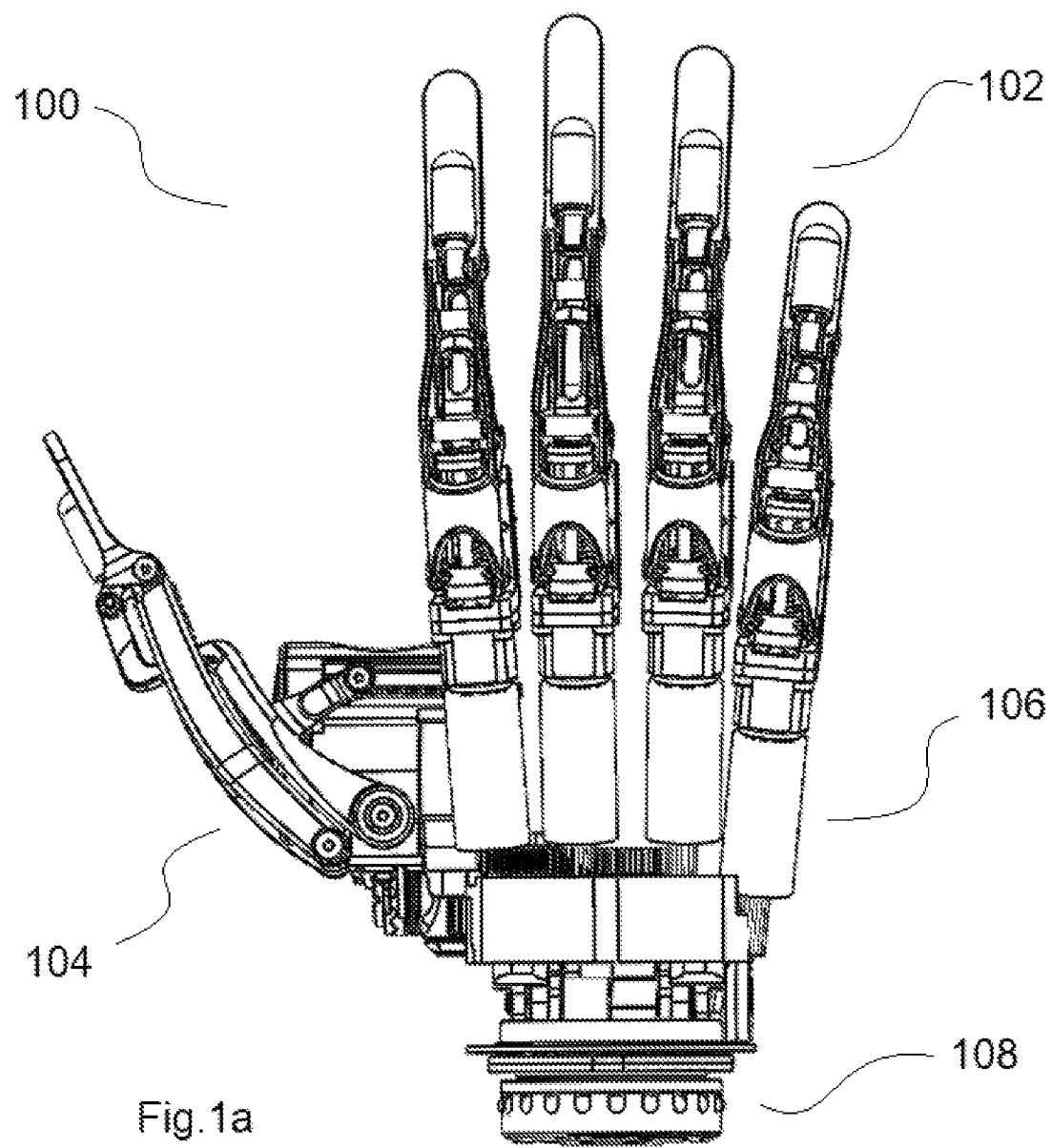
FIG. 1a illustrates the back side of a prosthetic hand according to certain embodiments of the present invention.
Figure 1B:
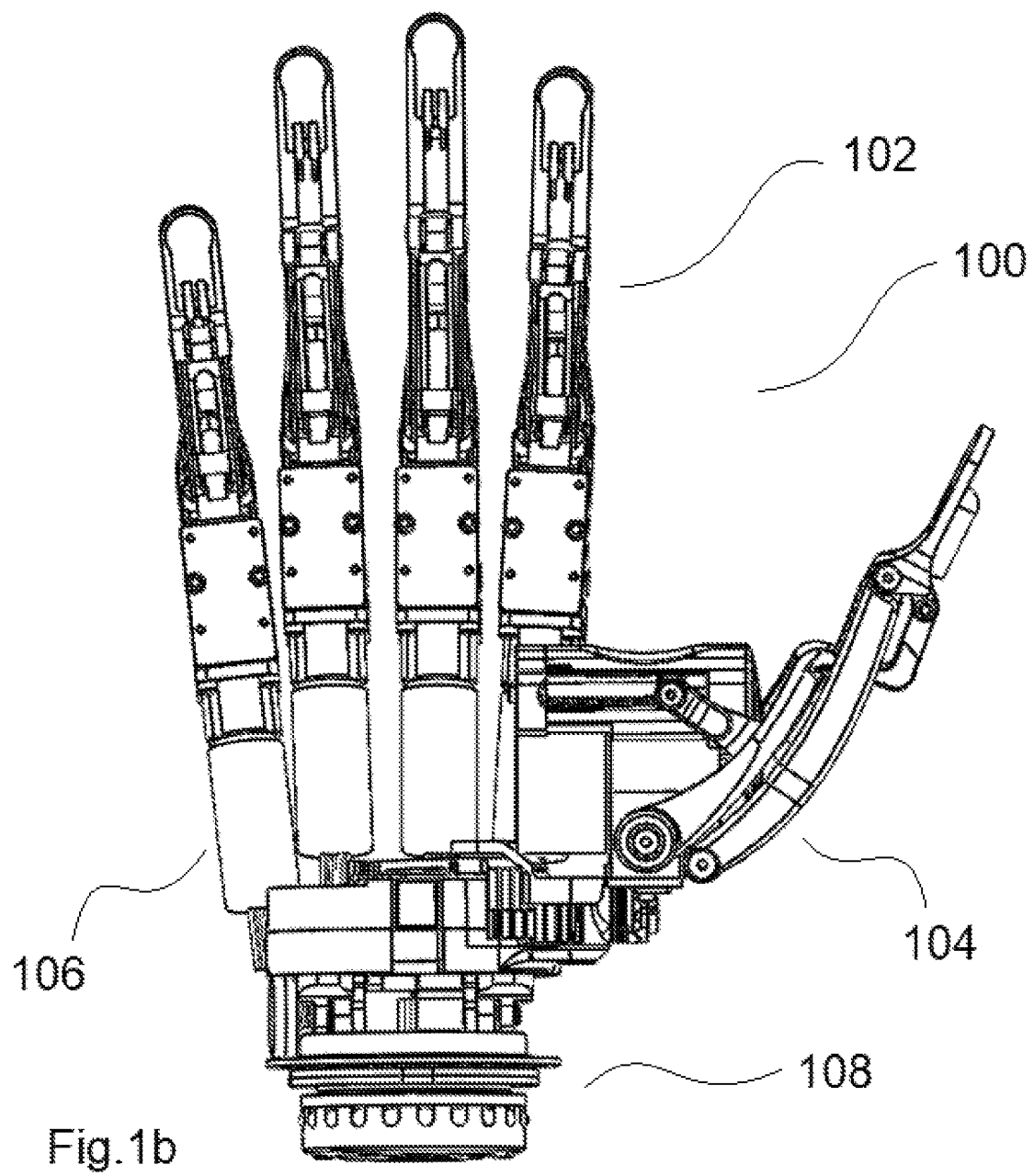
FIG. 1b illustrates the palm side of the hand of FIG. 1a with the thumb in a non-opposed position.
Figure 1C:
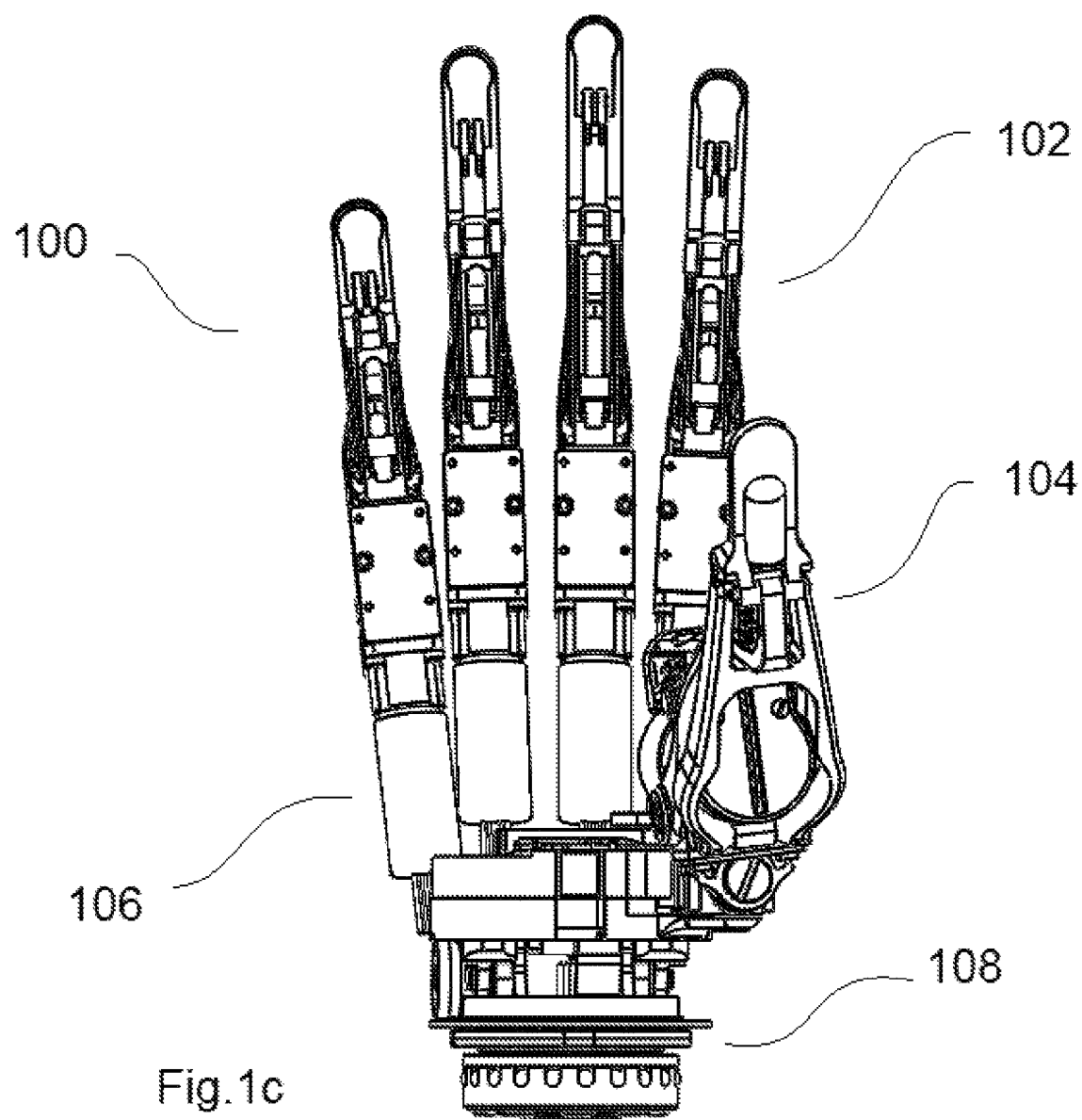
FIG. 1c illustrates the hand of FIGS. 1a and 1b with the thumb in an opposed position.
Figure 1D:
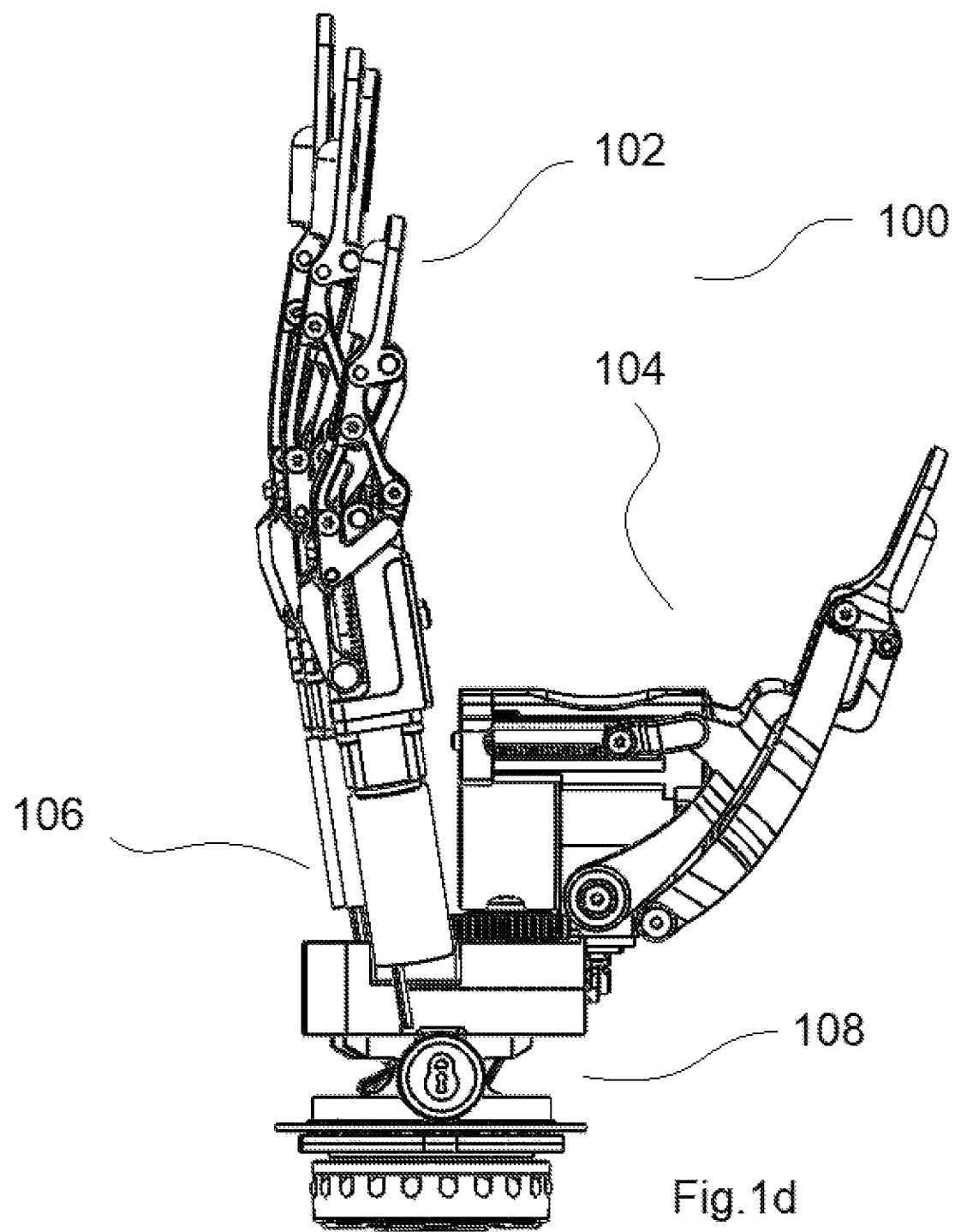
FIG. 1d illustrates a side view of the hand of FIGS. 1a to 1c with the thumb in an opposed position.
Figure 1E:
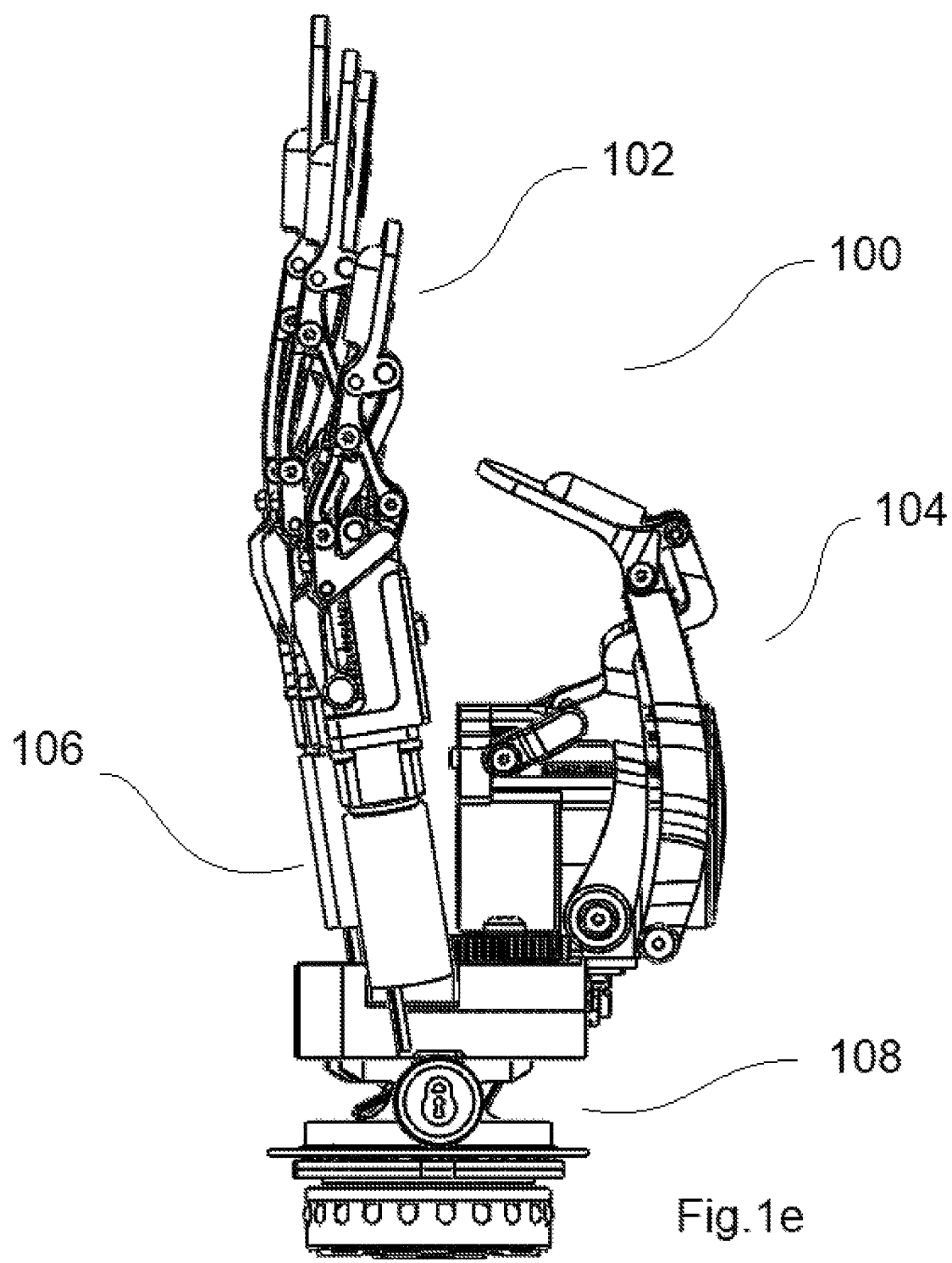
FIG. 1e illustrates a side view of the hand of FIGS. 1a to 1d with the thumb in an opposed position and in a flexed state.

As illustrated in FIGS. 1a to 1f, a prosthetic hand 100 according to certain embodiments of the present invention includes a plurality of finger assemblies 102 each extending from a palm region 106 and a thumb assembly 104. The hand 100 terminates at a wrist region 108 which is removably connectable to a socket (not shown) in which a residual limb of a user is received. The socket includes a plurality of sensors/electrodes arranged to engage with the skin of the user and detect electrical signals intentionally generated by the user's muscles which are then used by a controller to selectively control the finger assemblies 102 and thumb assembly 104 of the prosthetic hand 100. The connection between the wrist region and the socket may be any suitable connection, such as a bayonet connection, a threaded connection, a snap-fit connection, a frictional connection, or the like to secure the prosthetic hand to the socket and to allow electrical signals to pass from the sensors to the controller location in the hand. Alternatively, the sensors may communicate wirelessly with the controller located in the hand, e.g. via a Bluetooth™ or Wi-Fi connection, or the controller may be located remotely from the hand and connected wirelessly to operate the hand.

Figure 1F:
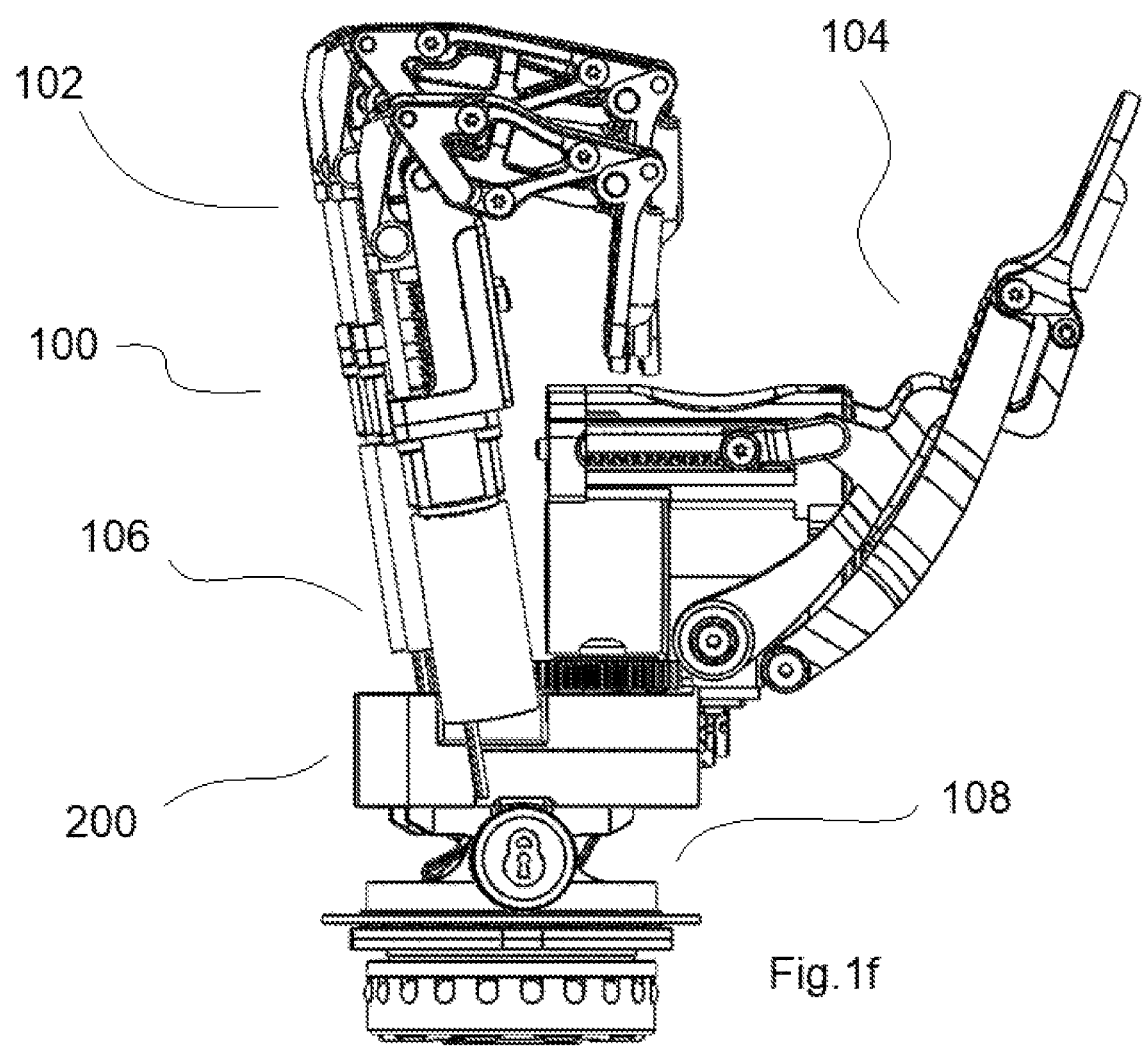
FIG. 1f illustrates a side view of the hand of FIGS. 1a to 1e with the thumb in an opposed position and the fingers in a flexed state.

As illustrated for example in FIG. 1f, a base chassis 200 of the hand 100 on which the finger assemblies 102, the palm region 106, and the thumb assembly 104 are supported is pivotally coupled to the wrist region 108.

Thumb Assembly

As illustrated in FIG. 2a, a first motor 210 is mounted in the base chassis 200 such that its drive shaft axis 212 is substantially parallel, if not substantially coaxial, with an axis of the wrist region 108 and/or the user's residual limb. This results in a system whereby the plane of rotation of the thumb is substantially perpendicular to the wrist and enables the thumb assembly to move in an efficient manner between opposed and non-opposed positions. It also allows the line of action of the thumb to be approximately colinear to the fingers when opposed and approximately perpendicular to the fingers when unopposed. The first motor 210 is aptly a DC brushed or brushless motor but may be any suitable rotational electric drive.

Figure 2B:
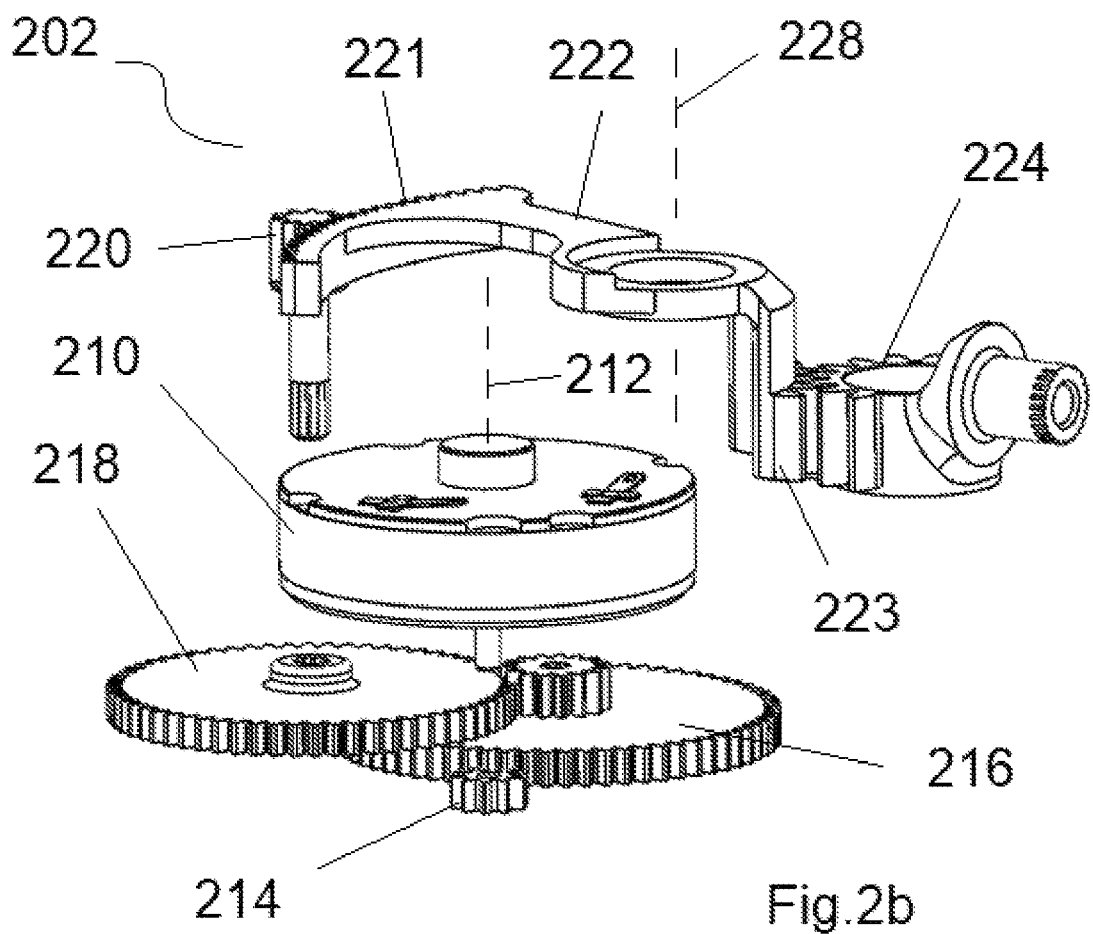

As illustrated in FIG. 2b, a reduction gearbox assembly 202 disposed in the base chassis 200 includes a drive gear 214 mounted on a shaft of the first motor 210 which is coupled via a plurality of gears 216,218,220,222 to a driven gear 224. Each of the plurality of gears is rotatably mounted in the base chassis 200 in a meshed relationship to an adjacent one of the gears to provide a desired reduction ratio between the drive gear 214 and the driven gear 224. Gear ratios in each pass are optionally around 7:1, 4:1 and 12:1 respectively which result is an effective ratio of around 350:1 and which in turn allows for a relatively fast speed and sufficient torque value for the thumb to rotate. A relatively high reduction ratio of greater than around 300:1 and/or a relatively inefficient gear assembly having multiple passes may effectively 'lock' the thumb 104 in a desired rotational position about the hub axis 302 against undesirable back-driving of the system. However, other suitable gear types and gear arrangements may be used to achieve a desired reduction ratio and/or locking effect.

The gear element 222 which is arranged to engage with the driven gear 224 is a compound gear having first and second gear portions 221,223 of different size. The gear portions may be integrally formed or fixed/connected to rotate together around the same axis 228. The first gear portion 221 is relatively thin and has a larger radius than the relatively thick and smaller second gear portion 223 which engages with the driven gear 224. The ratio between the first and second gears portions 221,223 is around 12:1. The first gear portion 221 defines an angle between its edges of around 70 degrees. The second gear portion 223 defines an angle between its edges of around 100 degrees.

Figure 2C:
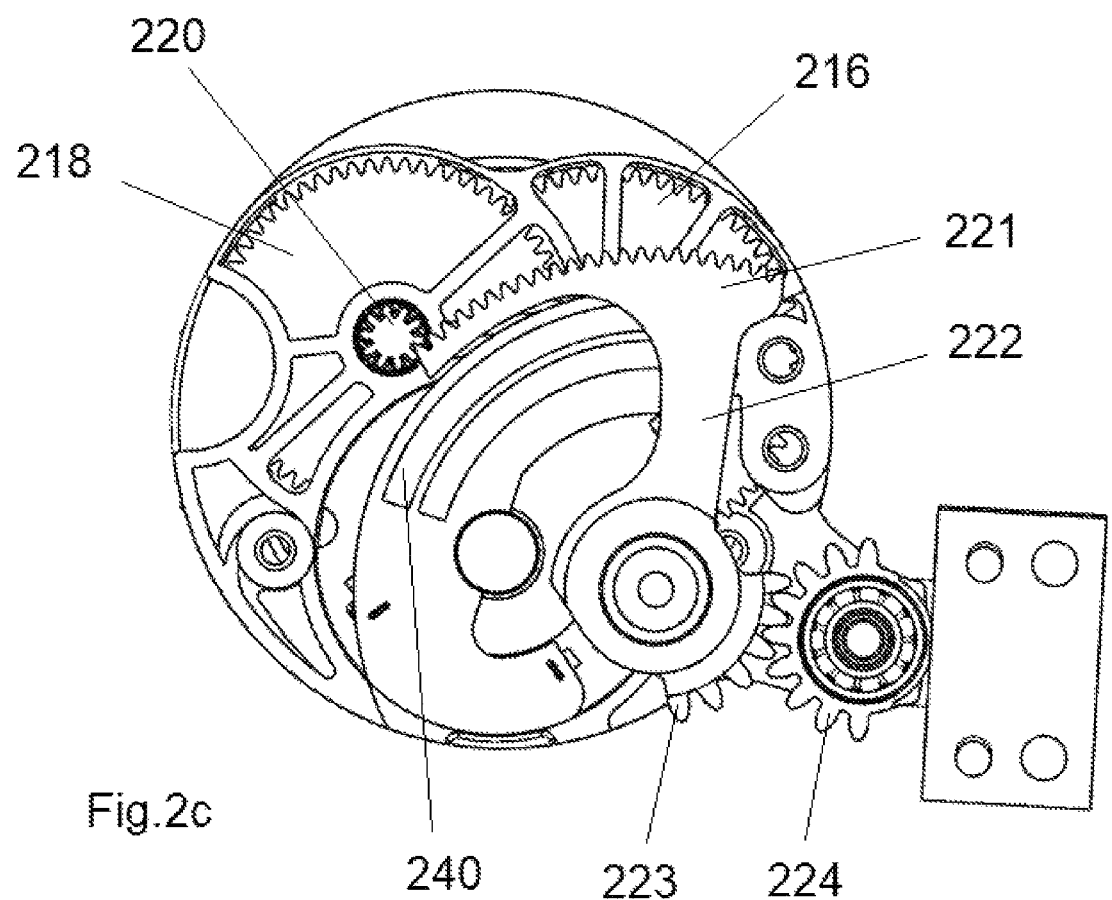
FIG. 2c illustrates a plan view of the thumb rotation mechanism with the thumb in the non-opposed position.

The thumb 104 is configured to rotate between opposed (FIG. 2c) and non-opposed (FIG. 2d) positions by around 60-70 degrees, aptly around 65 degrees. The driven gear 224 has 7 out of the 16 teeth of a complete gear and the second gear portion 223 of the compound gear element 222 has 6 of the 20 teeth of a complete gear. As such, the compound gear element 222 rotates about its axis 228 by around 65 degrees so does not need to be a complete gear and only a segment of the gear is required.

As illustrated in FIG. 2a, a track 240 of a linear potentiometer is fixed below the first gear portion 221 of the compound gear element 222 and a slider/wiper (not shown) of the linear potentiometer is fixed to the underside of the first gear portion 221 of the compound gear element 222. The linear potentiometer is electrically coupled to the controller to allow a rotational position of the compound gear element 222 and in turn the driven gear 224, and the thumb 104 between opposed and non-opposed positions, to be sensed for feedback, calibration and control purposes.

As illustrated in FIGS. 3a to 3d, the driven gear 224 is a segment gear and is aptly integral with a hub element 300 which is rotatable about a hub axis 302 and supported on a pair of axially spaced apart bearings 324,326. The hub axis 302 is substantially parallel with the drive shaft axis 212 and compound gear axis 228. The driven gear 224 may alternatively be connected to or mounted on the rotational hub element 300 instead of being an integral part thereof. Further alternatively, the driven gear 224 may be a full gear if required rather than a segment gear.

Extending from the hub element 300 is a rocker shaft 328 defining a rocker shaft axis 330 oriented substantially perpendicularly with respect to the hub axis 302. The rocker shaft 328 is integral with the hub element 300 to be rotationally movable therewith about the hub axis 302 when driven by the first motor 210. Alternatively, the rocker shaft 328 may be a separate component fixed to the hub element 300 to be rotationally movable therewith. A plurality of disc springs (e.g. Belleville washers) 331 are mounted on the rocker shaft 328 and located between a shoulder region 332 of the hub element 300 and a rocker platform 334 rotationally mounted to the rocker shaft 328. A retaining element 336 is mounted to the free end region of the rocker shaft 328 to be rotationally fixed thereto, e.g. by a spline arrangement, key, or the like, and to axially retain the rocker platform 334 on the rocker shaft 328. The abutting surfaces 335,339 of the rocker platform and retaining element respectively have a wave-form profile such that they correspondingly engage. The disc springs 331 urge the rocker platform 334 towards the retaining element 336. The retaining element 334 is axially secured to the rocker shaft 328 by a bolt or the like (not shown) which is received in a threaded bore 327 of the shaft 328.

The retaining element 336 includes a pair of lugs 341,343. Each lug is configured to engage a corresponding switch 345,347 located on the underside of the rocker platform 334. Each switch is a microswitch but could be any suitable push button/switch, or touch, optical, magnetic or capacitive sensor, or the like, which is suitable to indicate to a controller when the thumb 104 has been moved by a user to either side of the flexion/extension plane about the rocker shaft axis 330. Alternatively, the retaining element 336 may be suitable to allow a current to pass therethrough and each switch 345,347 may be an electrical contact which when engaged with a corresponding one of the lugs 341,343 completes an electrical circuit. Further alternatively, a sensor may send an input signal to the controller. Each lug 341,343 has a substantially curved contact surface but each contact surface could be substantially flat or the like.

Figure 3A:
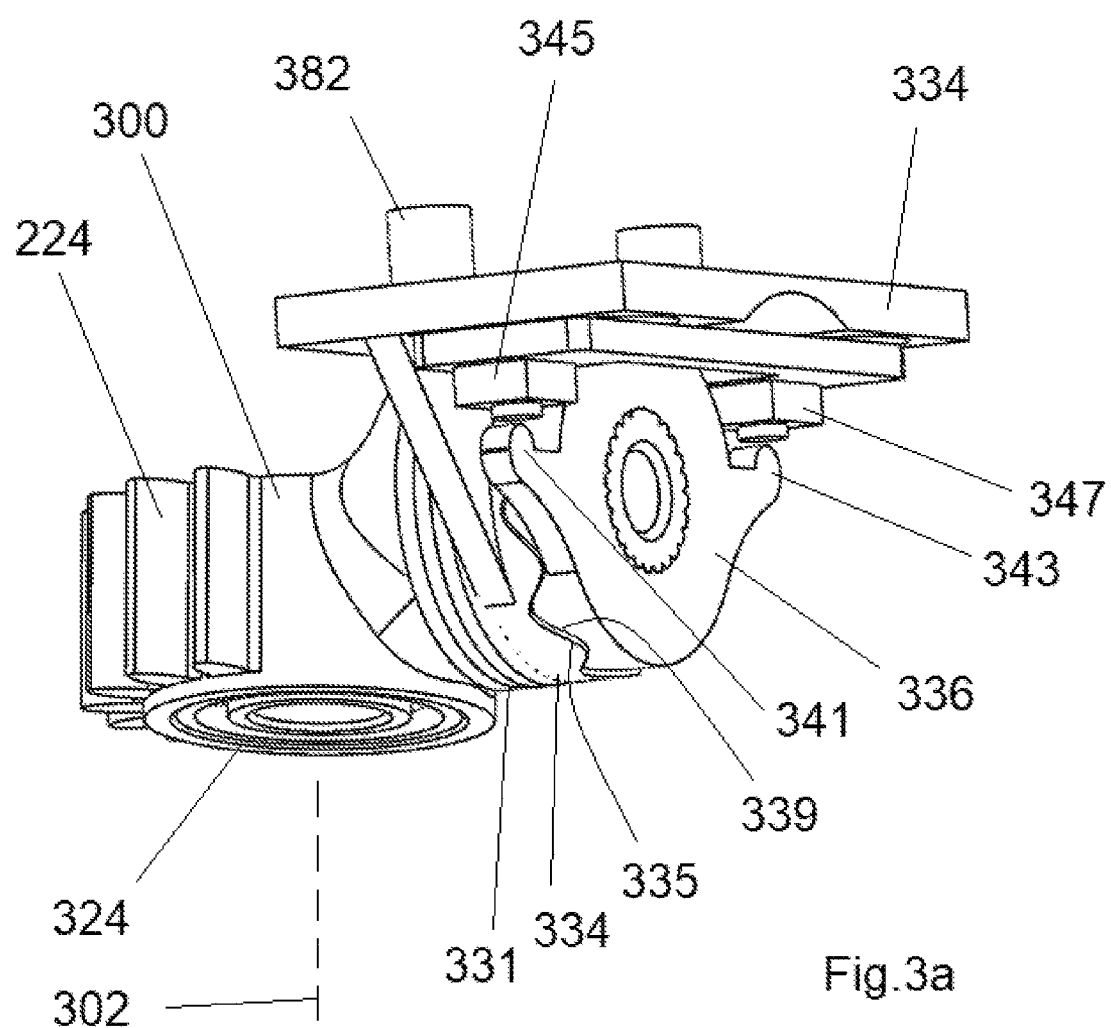
FIG. 3a illustrates a thumb rocker mechanism of the thumb assembly of the hand of FIGS. 1a to 1f.
Figure 3B:
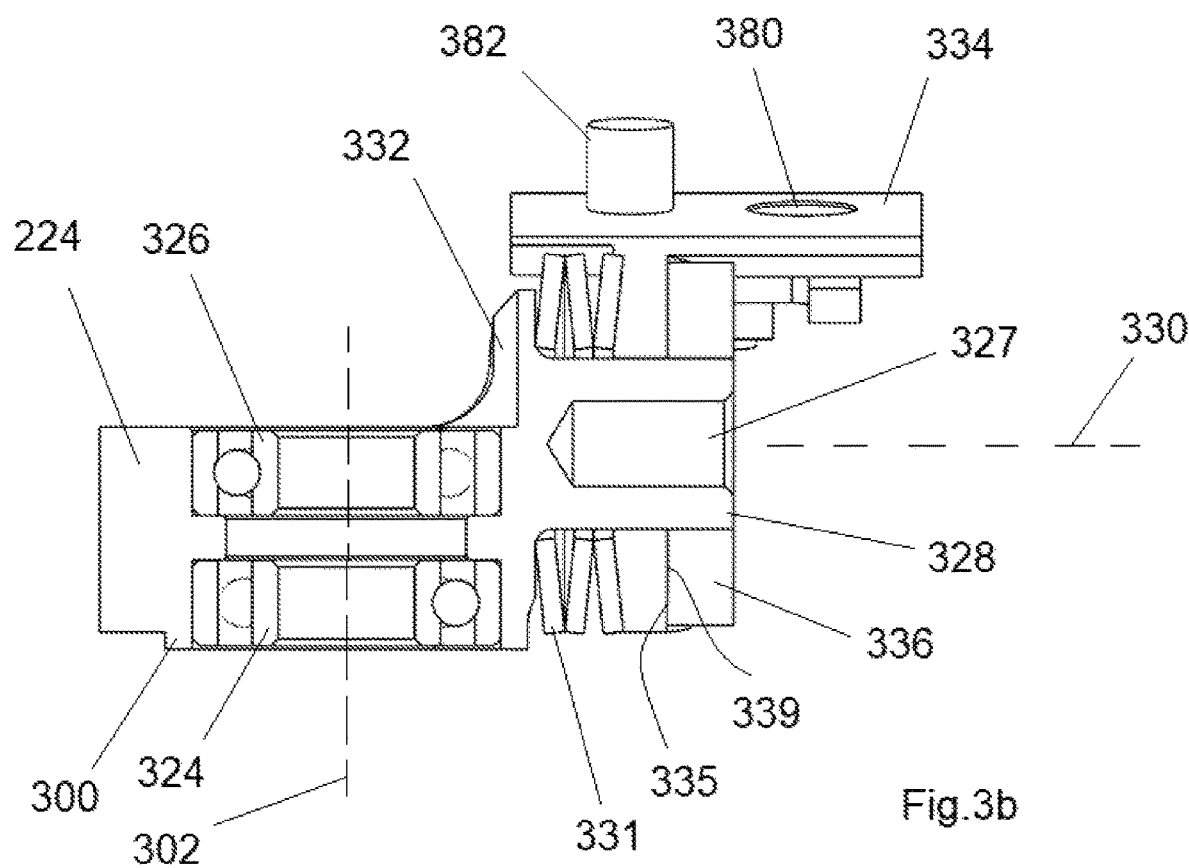
Figure 3C:
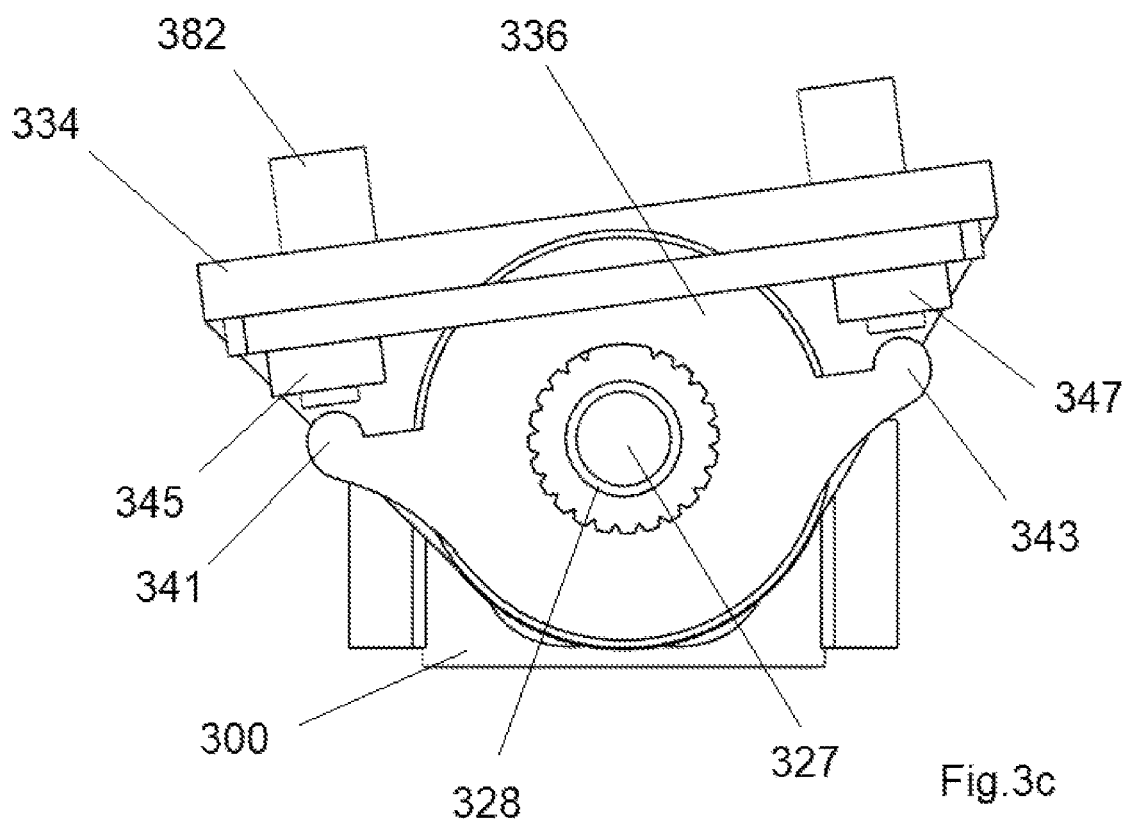
FIG. 3c illustrates an end view of the thumb rocker mechanism of FIGS. 3a and 3b.
Figure 3D:
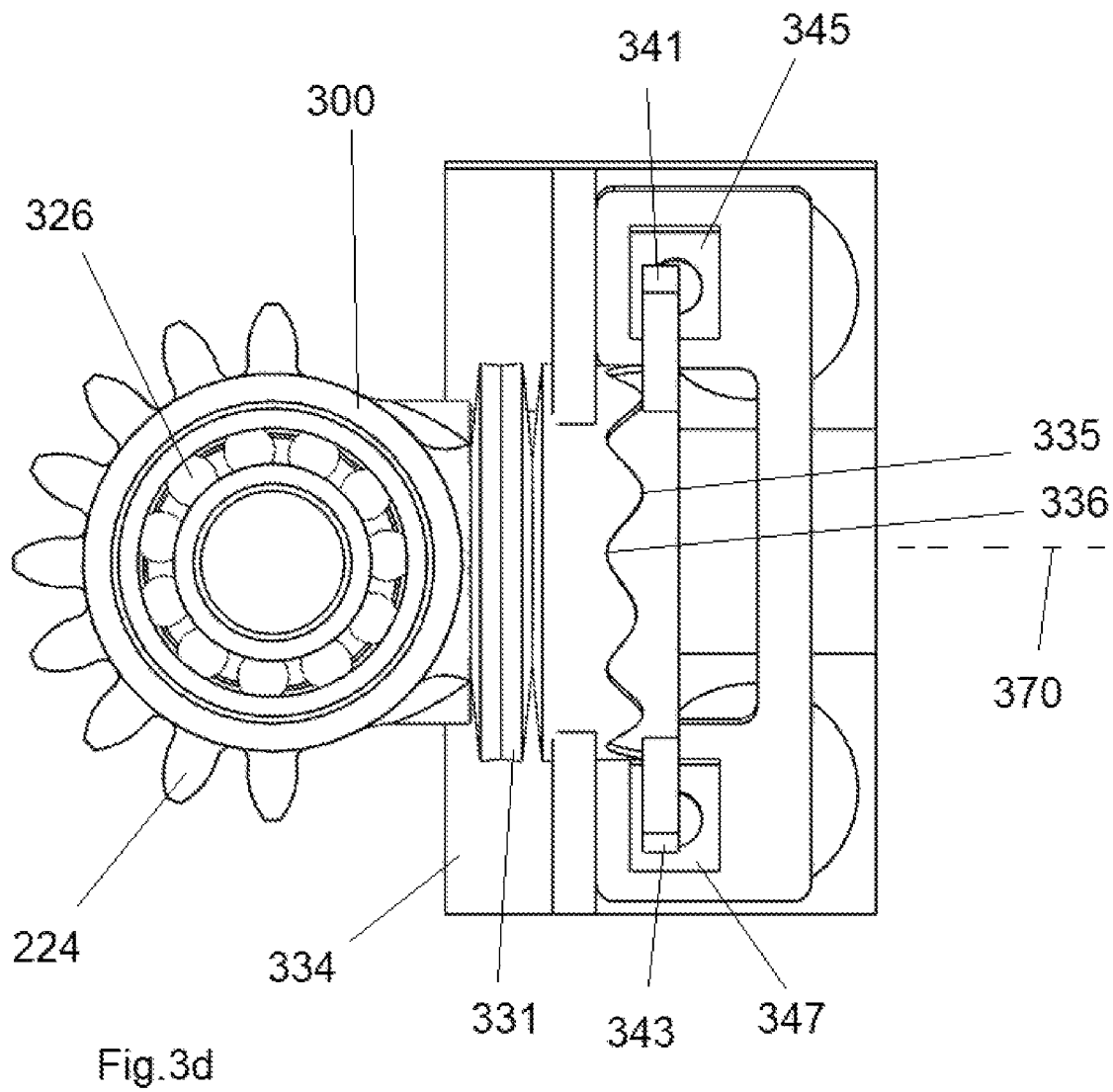
FIG. 3d illustrates a plan view of the thumb rocker mechanism of FIGS. 3a to 3c.

When a rotational force is applied to the rocker platform 334 about the rocker shaft axis 330, the wave-form profile of the abutting surfaces 335,339 cause the rocker platform 334 to move axially away from the retaining element 336 and against the force of the disc springs 331 to compress the same. A one of the switches is actuated by contact with a corresponding one of the lugs 341,343 which also limits the rotational travel of the rocker platform 334. When the rotational force is removed from the rocker platform 334, the same returns to its default position as illustrated in FIG. 3a such that a gap exists between the lugs and the switches and the platform is axially urged by the disc springs 331 to abut with the retaining element 336. Other mechanisms/arrangements may be used to urge the rocker platform 334 towards a neutral default position, such as torsion springs, clock springs or the like mounted on the rocker shaft 328 and engageable with the rocker platform.

An alternative arrangement for the rocker mechanism is illustrated in FIGS. 3e to 3g. The rocker mechanism 350 comprises an inner portion 352 and an outer portion 354. The inner portion 352 is fixed in relation to the rotatable hub element 300 and the outer portion 354 is pivotally coupled to the inner portion 352 by a pin 356. The outer portion 354 has a cavity 358 for receiving the inner portion 352 which defines inner surfaces 359, 361 to allow and limit the outer portion 354 to rotate about the pin 356 with respect to the inner portion 352. The degree of movement of the outer portion 354 is around +/−5 degrees. This in turn allows the thumb 104 which is coupled to the outer portion 352, such as via a rocker platform, to be selectively moved either side of a flexion/extension plane 365 of the thumb 104 about the pin axis 356 when a lateral force is applied to the thumb by a user. The pin 356 is disposed substantially on the flexion/extension plane 370 of the thumb 104 and substantially parallel with the hub axis 302. A pair of contact switches 366,368 are mounted on opposed inner surfaces of the cavity of the outer portion 354 such that, when the thumb 104 is moved laterally to either side, of the flexion/extension plane 370, one of the contact switches engages with a corresponding contact element 367,369 disposed on the inner portion 352. The switches could alternatively be push buttons/switches, or touch or optical or magnetic or capacitive sensors, or the like, which are suitable to indicate to a controller when the thumb 104 has been laterally moved by a user to either side of the flexion/extension plane 370 about an axis of the pin 356. Aptly, the thumb is urged by one or more spring elements, for example, towards a default position on the flexion/extension plane 370 thereof when no lateral force is being applied to it. In other words, the thumb rocker mechanism is configured to self-centre with respect to the flexion/extension plane 370 thereof when a lateral force is released from the thumb. For example, a spring-loaded follower 372 may be provided in the base region of the cavity 358 of the outer portion 354 which is adapted to follow a curved profile 374 at the end region of the inner portion 352 such that the follower 372 urges the outer portion 354 to return to the flexion/extension plane 370 when no lateral force is being applied to the thumb.

The thumb assembly 104 is mounted to the rocker platform 334 via fixing hole 380 and projections 382.

Figure 4B:
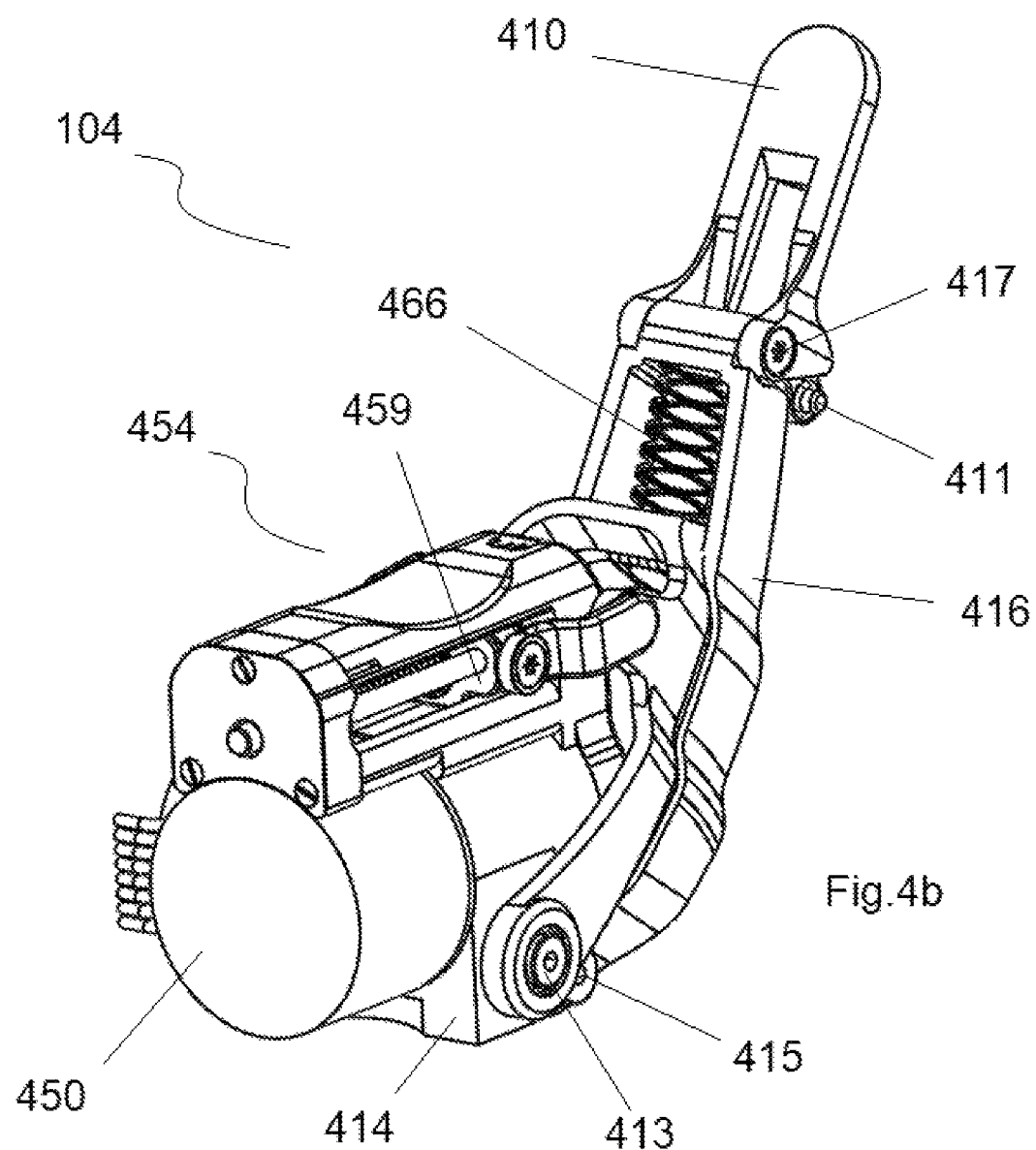

As illustrated in FIGS. 4a to 4d, the thumb assembly 104 includes a plurality of linkages which correspond to the phalanges of a real thumb. A first proximal phalange linkage 412 is pivotally coupled to a pivot base 414 by a first proximal pin 413 and is coupled to a second motor 450 by a drive linkage 464 to thereby selectively move the first proximal phalange linkage 412 between the extended and flexed positions along a thumb flexion/extension plane and about the first proximal pin 413. A distal phalange linkage 410 is pivotally coupled to the first proximal phalange linkage 412 via a first distal pin 411 enabling them to rotate relative to each other. A second proximal phalange linkage 416 is rotationally coupled at one end to the pivot base 414 by a second proximal pin 415 and at the other end to the distal phalange linkage 410 via a second distal pin 417. In the extended position, as illustrated in FIG. 4a, the second distal pin 417 is located inboard and above (distal direction) the first distal pin 411. The first proximal pin 413 is also located inboard and above the second proximal pin 415. This arrangement causes the distal phalange linkage 410 to rotate relative to the proximal phalange linkages 412,416 as the same rotate along the flexion/extension plane about the base axis 413 when the first proximal phalange linkage 412 is driven by the second motor 450.

Figure 4C:
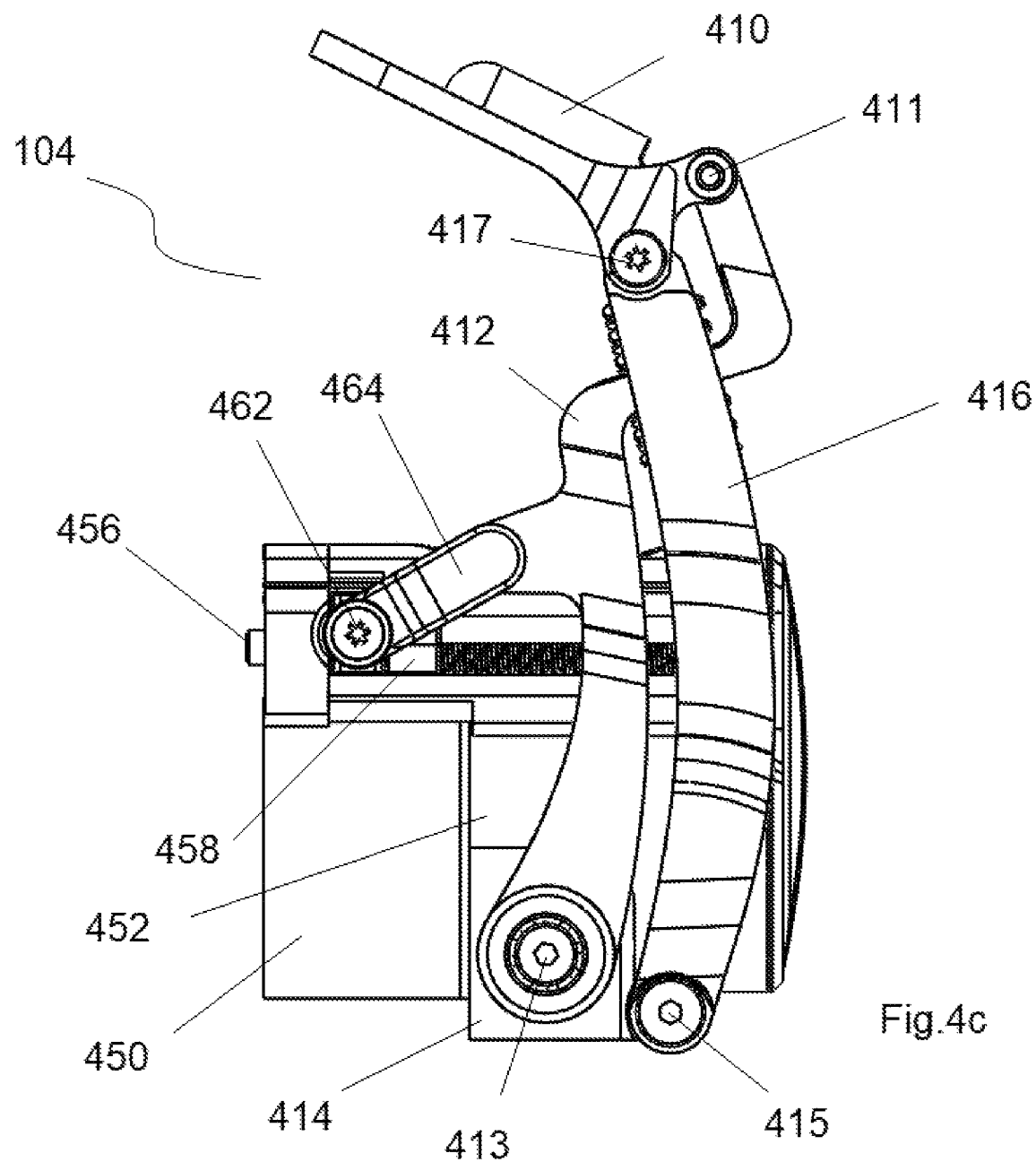
FIGS. 4c and 4d illustrate the thumb assembly of the hand of FIGS. 1a to 1f in a flexed state.
Figure 4D:
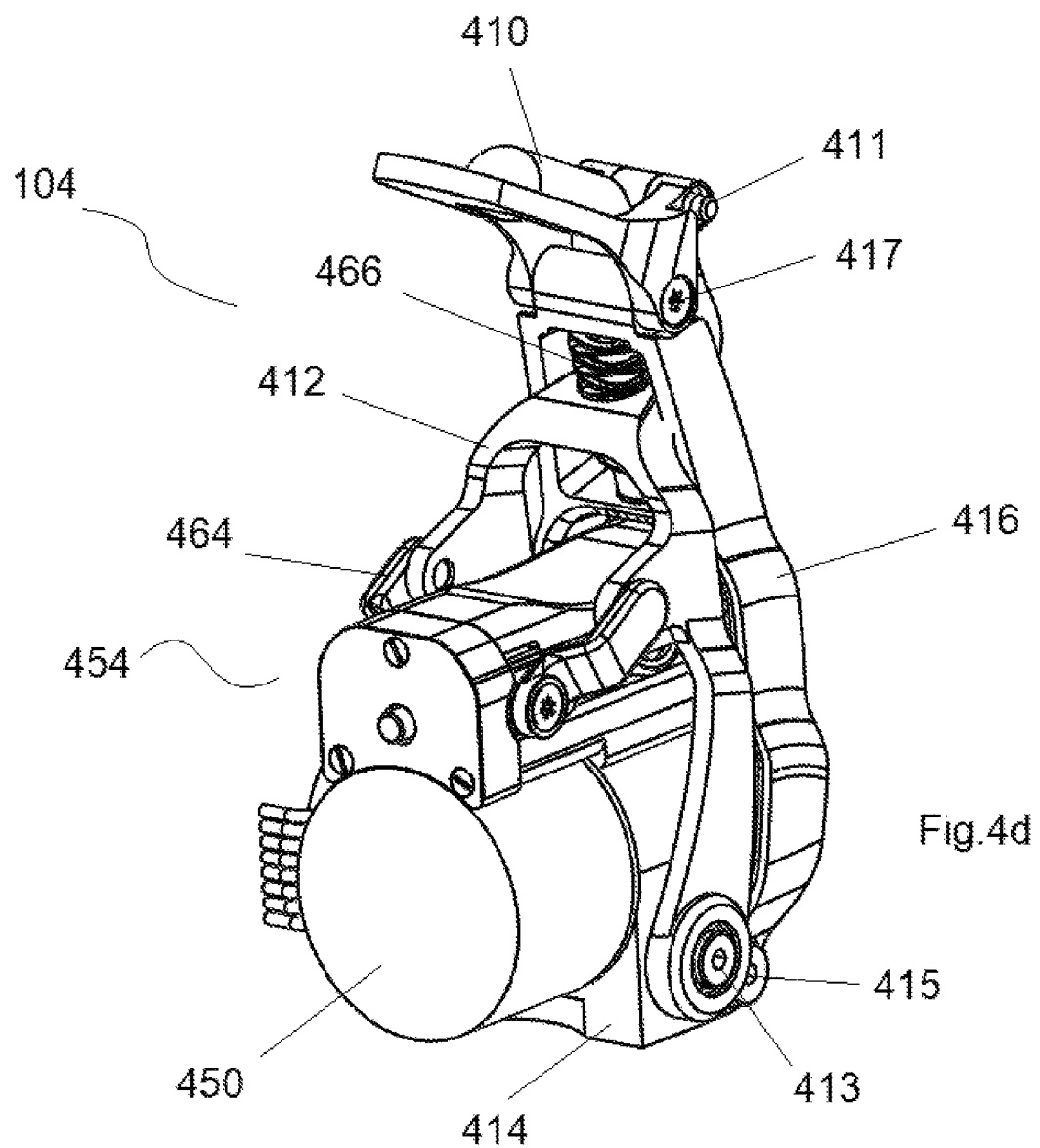

The thumb assembly 104 includes the second motor 450 coupled via a second reduction gearbox assembly 452 and a linear actuator 454 to the first proximal phalange linkage 412 to thereby selectively move the same towards or away from the palm region 106, i.e. along the flexion/extension plane of the thumb when the same is in, or between, opposed or non-opposed thumb positions (see FIGS. 4b and 4d). The second motor 450 is aptly a DC brushed or brushless motor but may be any suitable rotational electric drive. The linear actuator 454 aptly includes a leadscrew 456 selectively rotatable about a leadscrew axis 457 by the second motor 450 and via the second gearbox 452. A leadscrew nut 458 is moved along the leadscrew axis 457 by rotation of the leadscrew 456 and is in engagement with a leadscrew slider 459 slidably guided by a pair of elongate guide members 460 located on each side of the leadscrew 456. As best illustrated in FIG. 4b, the leadscrew slider 459 includes a pair of spaced apart through holes each for receiving a respective one of the guide members 460. Each end region of the leadscrew slider 459 is pivotally coupled via a pin 462 to the drive linkage 464 which in turn is pivotally coupled approximately midway along the first proximal phalange linkage 412.

The leadscrew 456, leadscrew nut 458 and slider 459 are coaxially arranged to share the leadscrew axis 457. Whilst the second motor 450 is located below the leadscrew axis 457 it may be also arranged on the leadscrew axis. Aptly, the leadscrew axis 457 is oriented substantially perpendicular to the wrist axis and substantially parallel with a path of the distal phalange tip during movement along the flexion/extension plane. This arrangement provides improved gripping in terms of direction, force and efficiency.

The first proximal phalange linkage 412 includes a support surface proximal its distal end which is oriented substantially perpendicularly with respect to a longitudinal axis of the first proximal phalange linkage 412. A spring 466 is located between the support surface of the first proximal phalange linkage 412 and a further support surface provided by a closed distal end region of the secondary proximal linkage 416 to urge the thumb assembly 104 towards an open (extended) thumb position (as illustrated in FIGS. 4a and 4b). The spring 466 may aptly be a continuous length extension spring, or alternatively the thumb may be urged towards the default thumb open position by another arrangement including a torsion, compression, or tension spring, or an elastic element, or a combination of the same. For example, a spring may act directly on the leadscrew slider 459 to urge it to follow the leadscrew nut 458 when the same is translated in the direction to extend (open) the thumb.

When the leadscrew nut is driven in the opposite direction to flex (close) the thumb, the slider is driven by the leadscrew nut which would compress the spring.

When a voltage is applied to the motor 450, a torque is transferred via the gearbox 452 to the leadscrew 456 which transmits a linear force to the leadscrew nut 458 and in turn to the leadscrew slider 459. The linear force, in the direction from proximal to distal (left to right in FIG. 4a), transmits from the leadscrew slider 459 through the drive linkage 464 and the first proximal phalange linkage 412 to the distal phalange linkage 410 and causes the thumb to rotate about its base axis 413 towards the palm region 106 along the extension/flexion plane and, in turn, the distal phalange linkage 410 to rotate inwardly, to a thumb closed (flexed) position (as illustrated in FIGS. 4c and 4d). When the second motor 450 is driven in the opposite direction, the leadscrew nut 458 is translated from distal to proximal (right to left in FIG. 4c) and, in turn, the leadscrew slider 459 is held in engagement with the leadscrew nut 458 by the spring element 466 within the thumb urging the same towards the thumb open (extended) position. Such an arrangement enables the thumb assembly 104 to fully fold towards the palm region 106 when an external force is exerted on it without driving the second motor 450 thus preventing the thumb assembly, particularly the drive assembly thereof, being damaged by unintentional knocks/impacts. When the external force is removed, the thumb assembly 104 is urged by the spring 466 back towards the thumb open position until the leadscrew slider 459 abuts the leadscrew nut 458. A linear potentiometer (not shown) is coupled to the leadscrew slider 459 to allow the controller to monitor a location thereof along the leadscrew 456, and in turn a position of the thumb along the flexion/extension plane, whether the thumb is moved by the second motor 450 or by an external force.

Aptly, the second gearbox 452 is a two-speed gearbox capable of switching between a low torque, high speed output and a high torque, low speed output when required. High torque is aptly only required for flexion. Extension is controlled by the spring and a high opening torque would merely lead to separation of the leadscrew nut and slider. Grip force is achieved by increasing the force in the thumb after the motion of the fingers has formed the grip. Increasing the torque in the second motor 450 causes the gearbox 452 to change gear and the grip force is increased with the thumb optionally moving at a slower speed. The leadscrew 456 in the thumb assembly prevents external loads applied to the thumb effecting a gear change. Changing from low output torque to high output torque is controlled by the motor torque. The gearbox remains in high torque until all the torque is wound off the shift spring. Back-driving is the result of the load (or thrust force) pushing axially on the screw or nut to create rotary motion. All screws, depending on their efficiency, will back drive. The resulting torque is known as 'back-driving torque' and is the torque required to hold a load in position. The gearbox changes between high and low speed at a back fixed torque, the back torque in the gearbox being generated by resisting the rotation of the leadscrew, as an item is gripped. As an item is released, the back torque reduces in low speed until the torque threshold is met and the gearbox shifts into high speed.

By defaulting to a relatively high speed, low force system, users will have a hand that is able to grasp objects with a compliant grip (the motive stage of the gripping sequence) before the thumb acts to secure the grip. FIGS. 7a to 7d show a range of different grips that may be required by typical users of the hand. In most cases the desire for a relatively high gripping force may be suitably achieved by having a single two-speed gearbox 452 for driving flexion and extension of the thumb. Enabling the high grip force may be selected dependent on grip, e.g. a high grip force is not appropriate for a point or mouse grip but may be desirable for a power or tripod grip. The torque output from the thumb may be kept relatively low enough to prevent an automatic gear change, whilst external loads exerted on the thumb will not force the gearbox to shift as no torque may be transmitted back through the leadscrew. Alternatively, or additionally, the high force gear shifting may be disabled/prevented when closing the hand for some grips to thereby promote safety.

Finger Assembly

One of the finger assemblies 500 according to certain embodiments of the present invention is illustrated in FIGS. 5a to 5d. A third motor 502 is coupled to a third reduction gearbox assembly 504 of which the output is coupled to a linear actuator 506. The motor 502 is aptly a DC brushed or brushless motor but may be any suitable rotational electric drive. The linear actuator 506 aptly includes a leadscrew 508 selectively rotatable about a leadscrew axis 510 by the motor 502 and via the gearbox assembly 504. The leadscrew 508 is supported at each end by a bearing 518 in a finger chassis 509. A leadscrew nut 512 is moved along the leadscrew axis 510 by rotation of the leadscrew 508 and is in engagement with a leadscrew slider 514 slidably guided by a pair of elongate guide members 516 located on each side of, and oriented parallel with, the leadscrew 508. The leadscrew slider 514 includes a pair of spaced apart through holes each for receiving a respective one of the guide members 516. The leadscrew nut 512 may also engage with the guide members 516. Such an arrangement prevents the leadscrew nut 512 and leadscrew slider 514 rotating whist the leadscrew 508 is being driven in either direction by the motor 502 whilst ensuring the same remain coaxial with respect to the leadscrew axis 510. The use of a leadscrew to convert motor rotation into a linear motion at a suitable pitch, such as 1 mm or less, also desirably prevents 'back driving' so the fingers are essentially locked in position when driven to a desired position and the motor power is removed. This may be desirable for certain grips, e.g. a hook grip for lifting items such as a bag, or to withstand a thumb force such as in a pinch grip. A position sensor 520 is mounted adjacent to the leadscrew 508 and configured to sense/monitor a position of the leadscrew slider 514 and feedback a corresponding signal to the controller. Aptly, the position sensor is a linear potentiometer to determine an absolute position of the slider 514 and in turn a position of the finger assembly along the flexion/extension plane. A Hall sensor arrangement is used to control the commutation of the motor and also to measure the rotational speed thereof allowing the current draw to be determined.

Desirably the motor, gearbox, leadscrew and leadscrew nut of each finger assembly all share the same axis 510, i.e. are coaxially arranged with respect to each other. The motor 502 is desirably located at the palm region of the hand therefore bringing the centre of gravity towards the wrist compared to conventional mechanical hands. This arrangement provides improved gripping of the fingers in terms of direction, force and efficiency, and in turn allows the use of a relatively small motor which in turn provides a more compact and shallower palm region and reduces patient fatigue and potential associated discomfort in view of the reduced weight and the centre of gravity of the hand being closer to the wrist.

Figure 5A:
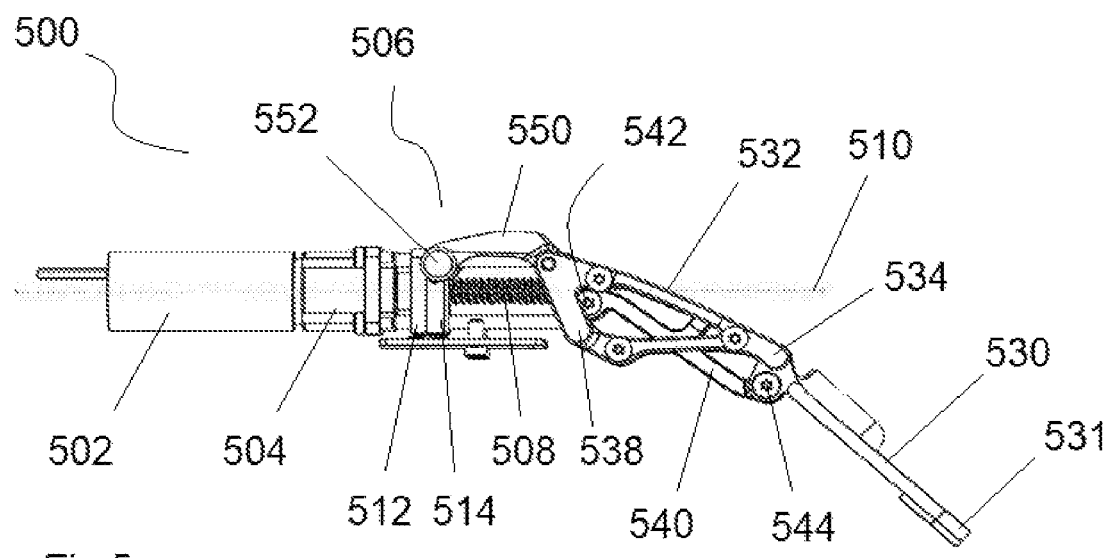
FIGS. 5a and 5c illustrate a side view of a finger assembly of the hand of FIGS. 1a to 1f in an extended state.
Figure 5B:
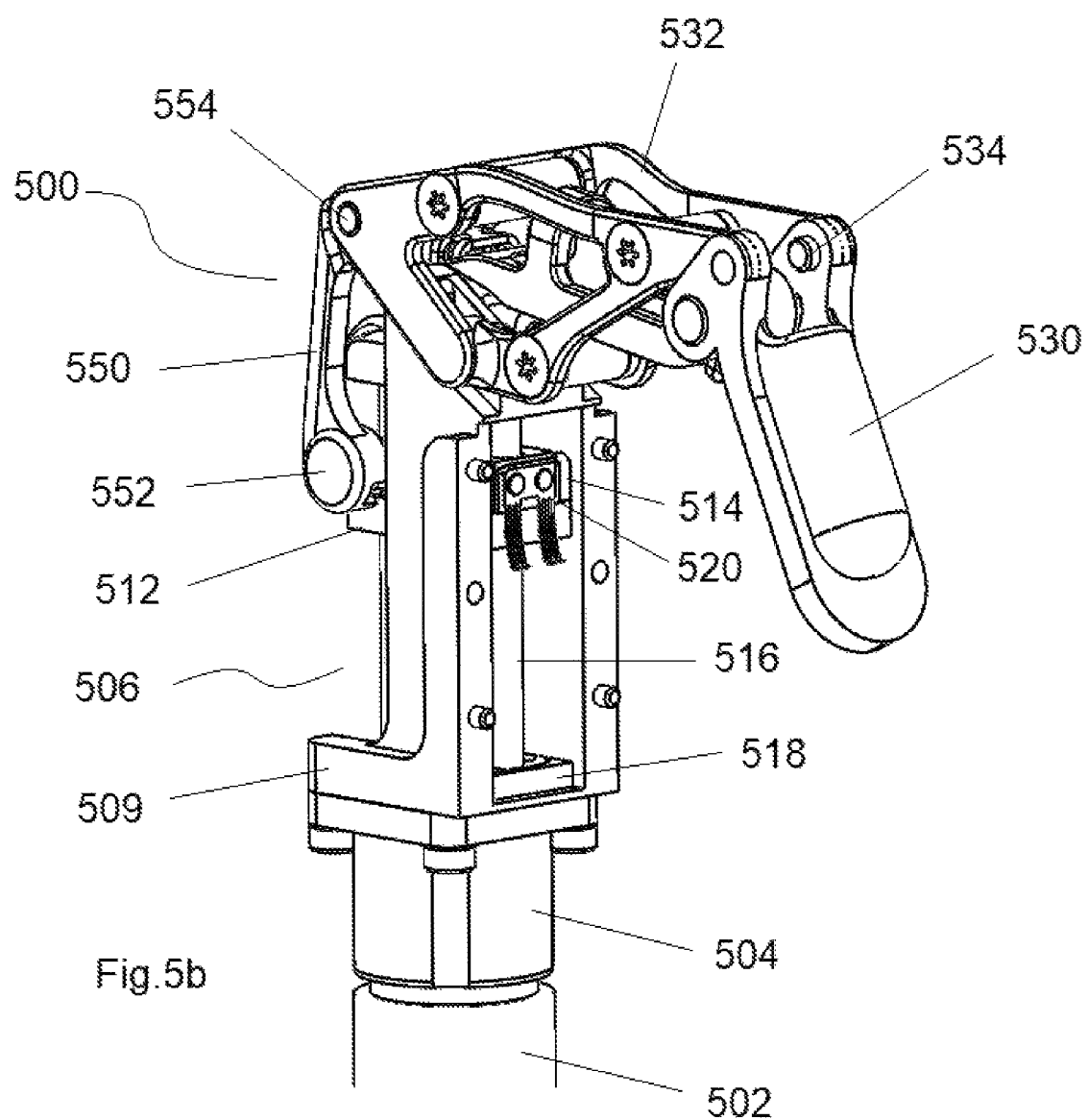
FIGS. 5b and 5d illustrate the finger assembly of FIGS. 5a and 5c in a flexed state.
Figure 5C:
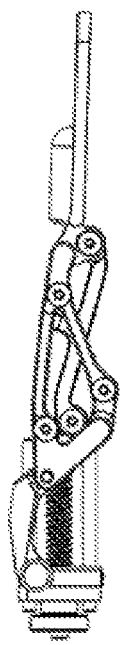

The finger assembly 500 includes a plurality of linkages which correspond to finger phalanges of a real finger. A first proximal phalange linkage 532 is pivotally coupled to a finger chassis 509 by a first proximal pin 538 and to the slider 514 by a knuckle linkage 550 to thereby allow the first proximal phalange linkage 532 to rotate about the first proximal pin 538 along the flexion/extension plane when driven by the motor 502. A distal phalange linkage 530 is pivotally coupled to the distal end region of the first proximal phalange linkage 532 by a first distal pin 534 enabling them to rotate relative to each other. A second proximal phalange linkage 540 is pivotally coupled at a proximal end region to the chassis 509 by a second proximal pin 542, which is located above the first proximal pin 538 (as viewed from the side in FIG. 5a) and is pivotally coupled at its distal end region by a second distal pin 544 which is located below the first distal pin 534. This arrangement causes the distal phalange linkage 530 to rotate relative to the proximal phalange linkages 532 as the same is rotated towards or away from the palm. This is because the second proximal phalange linkage 540 is pinned to the chassis above the first proximal phalange linkage 532 and, as the proximal phalange linkage is rotating away to maintain the fixed distance, the distal phalange linkage 530 is caused to rotate forward due to the second proximal phalange linkage 540. This arrangement causes the distal phalange tip 531 to move through a fixed arc when the first proximal phalange linkage 532 is rotated by the motor 502. The mechanism is driven by the knuckle linkage 550 which is pivotally coupled by a pin 552 to the leadscrew slider 514 and pivotally coupled to the first proximal phalange linkage 532 by a pin 554 which is located above both the proximal chassis pivot 538 (as viewed from the side in FIG. 5a) and the second proximal phalange linkage 540. The linkages are spring-loaded to urge the finger assembly 500 towards a default straight finger position (as illustrated in FIG. 5c). A continuous length extension spring may be used or the spring/s may be a torsion, compression, tension spring, or an elastic element, or a combination.

Figure 5D:
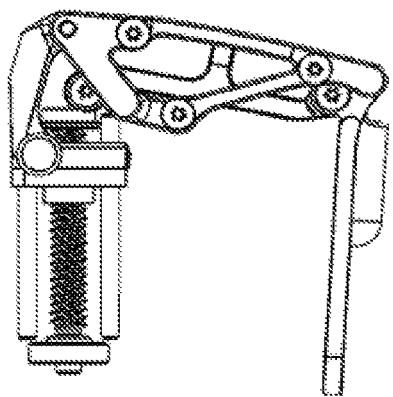

When a voltage is applied to the motor 502, a torque is transferred to the gearbox assembly 504 and to the leadscrew 508 which transmits a linear force to the leadscrew nut 512. The linear force in the direction from proximal to distal along the leadscrew axis 510 transmits from the leadscrew nut 512 to the leadscrew slider 514 which in turn transmits force to the knuckle linkage 550 and causes the first proximal phalange linkage 532 to rotate about the first proximal pin 538 and the second proximal phalange linkage 540 to rotate about the second proximal pin 542. Further rotation of the first proximal phalange linkage 532 and the second proximal phalange linkage 540 causes the distal phalange linkage 530 to rotate towards a closed (flexed) position (as illustrated in FIG. 5*d*). When the motor 502 is driven in the opposite direction, the leadscrew nut 512 is axially moved from distal to proximal along the leadscrew axis 510 and the leadscrew slider 514 is urged against the leadscrew nut 512 by the spring element/s within the finger linkages. Such an arrangement enables one or more finger assemblies 104 to independently fully fold towards the palm region 106 of the hand when an external force is exerted on them thus preventing one or more finger assemblies, particularly the drive assemblies thereof, being damaged by unintentional knocks/ impacts. When the external force is removed, the fingers spring in an opening direction until the leadscrew slider 514 abuts the leadscrew nut 512. In view of the linear potentiometer 520 coupled to the leadscrew slider 514, the controller can track/determine a position/orientation of each finger assembly 500 whether a finger/s is moved by the motor 502 or by an external force.

Each phalange tip 531 may include a force sensor, such as a force sensitive resistor (FSR), to enhance control responsive to a force applied at the phalange tip and enable a reliable auto-grip feature via feedback from one or more of the force sensors in use responsive on the grip selected, as described further below.

Wrist Assembly

As illustrated in FIGS. 6*a* and 6*b*, the wrist region 108 of the hand according to certain embodiments of the present invention comprises an arm plate 600 coupled to the base chassis 200. The base chassis 200 supports the finger assemblies and thumb assembly and the arm plate 600 is mountable to a limb socket. The base chassis 200 is pivotally coupled to the arm plate 600 by a hinge assembly including for example a hinge pin 602 defining a hinge axis 604. A pair of spaced apart lugs 605,606, or the like, respectively extend from each of the base chassis 200 and the arm plate 600 with which the hinge pin 602 engages to thereby pivotally couple the base chassis 200 and arm plate 600 together. Other forms of hinge arrangement may be suitable, such as the arm plate lugs each having an integral pin or projection which cooperates with a corresponding hole or recess in a respective one of the base chassis lugs. The hinge axis 604 is oriented substantially perpendicular to an axis of a user's radius and ulnar, and also to the wrist axis of the device.

One or more springs 607,608 are mounted on the pin to urge the base chassis 200 towards a neutral position, when no rotational force is being applied to the base chassis in use, wherein a plane of the base chassis is substantially parallel with a plane of the arm plate. As shown best in FIG. 6*b*, a pair of torsion springs are axially mounted on the hinge pin 602. The end region of a first leg of each spring is fixed or coupled to the hinge pin to be rotationally constrained thereto. An end region of a second leg 609 of each spring engages with the arm plate 600 on a respective side of the hinge pin. The second leg of each spring comprising the flat engagement surface is angled by around 60 degrees and has a curved ski-like end region to allow the same to slide over an upper surface of the arm plate when the spring is being compressed or uncompressed.

The second leg 609 of each spring is configured to perform like a leaf spring and the coiled portion is configured to perform like a spiral torsion spring, such that each spring is a hybrid combination of a spiral torsion spring and a leaf spring. The sum of the combined torques of the two types of spring provides a high resistive torque, but also a particularly compact size to allow the joint to be relatively compact and short and the flex axis to be closer to that of a natural wrist joint. The torsion springs are also laminated, i.e. comprising two or more unconnected layers which are allowed to slide over each other during coiling and uncoiling, to thereby reduce stress in the material which reduces fatigue during flexing and minimises/eliminates the risk of spring failure in use.

When the base chassis 200 is rotated relative to the arm plate 600 to either side about the hinge pin axis 604 when a rotational force is applied to the basis chassis, such as when the hand is unintentionally knocked in use, the underside of the base chassis 200 engages with a substantially flat engagement surface of the second leg of a respective one of the springs 607,608. Further rotation of the base chassis with respect to the arm plate causes the coiled torsion spring portion to tighten around the hinge pin and the leaf spring portion to compress. The combination of the two actions provides a resistive torque. The resistive torques of both springs equalises when the base chassis 200 and the arm plate 600 are parallel.

The base plate 200 is adapted to rotate +/− around 30 degrees about the hinge axis relative to the flat neutral plane. When the rotational force is removed from the base chassis, the compressed spring urges the base plate back to the neutral position with respect to the arm plate. Aptly, the two spiral torsion springs 607,608, e.g. clock springs, are configured such that one resists flexion and the other resists extension and are adapted such that when one spring is being compressed, the other spring decouples from the base chassis and provides no resistance to the spring being compressed. The only time both springs may be 'active' is +/− around 5 degrees to either side of the neutral plane. The clock springs 607,608 are made of a spiral wound spring steel or other suitable material. Other forms of resilient member, such as compression and/or extension springs, or a torsion bar arrangement, or the like, may also be suitable to provide such a wrist mechanism to allow the hand to flex and extend relative to a user's arm.

In addition to the passive flex mechanism described above, the wrist region 108 further includes a locking arrangement 650 which allows a user to lock the hand 100 in a number of positions relative to the arm about the hinge axis 604. This is particularly useful for eating, for example.

Figure 6C:
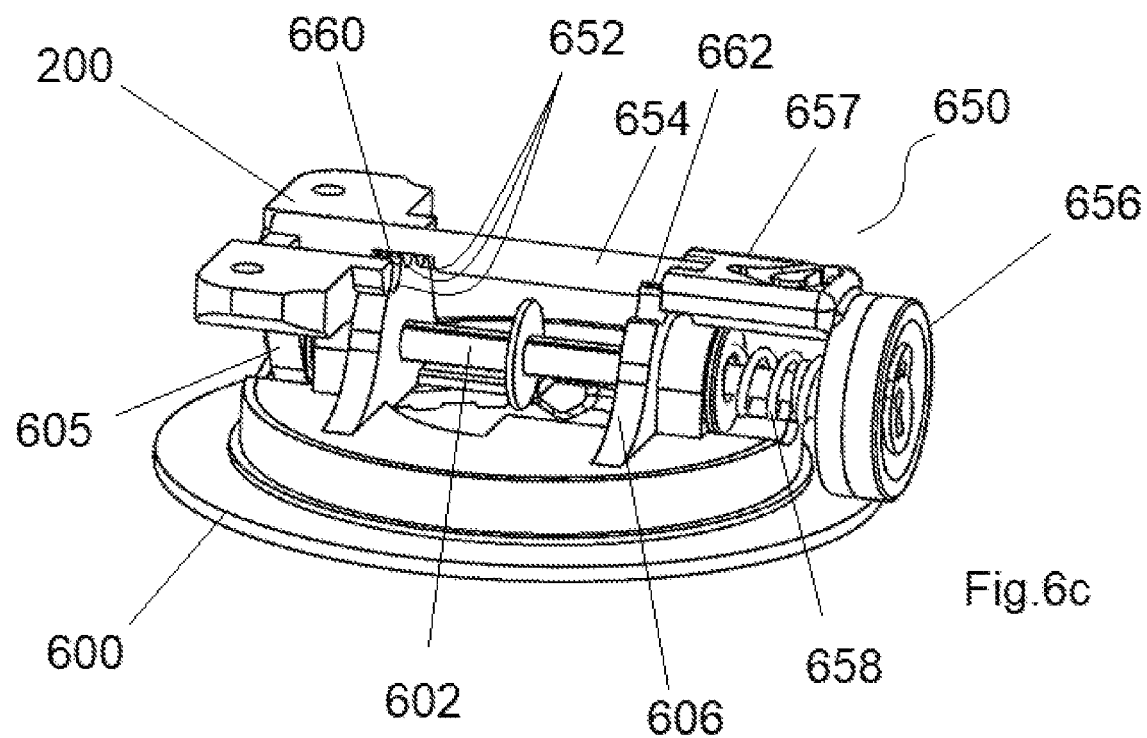
FIGS. 6c and 6d illustrate a lock arrangement of the wrist assembly of FIGS. 6a and 6b in an unlocked and locked state respectively.
Figure 6D:
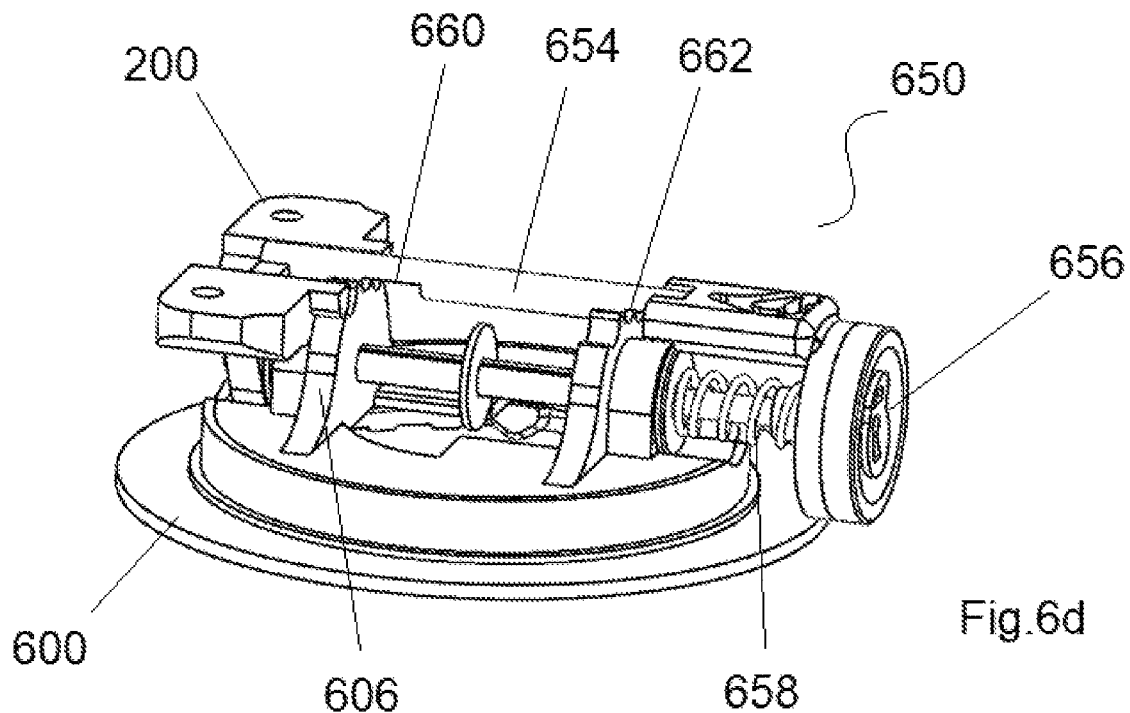
Figure 6J:
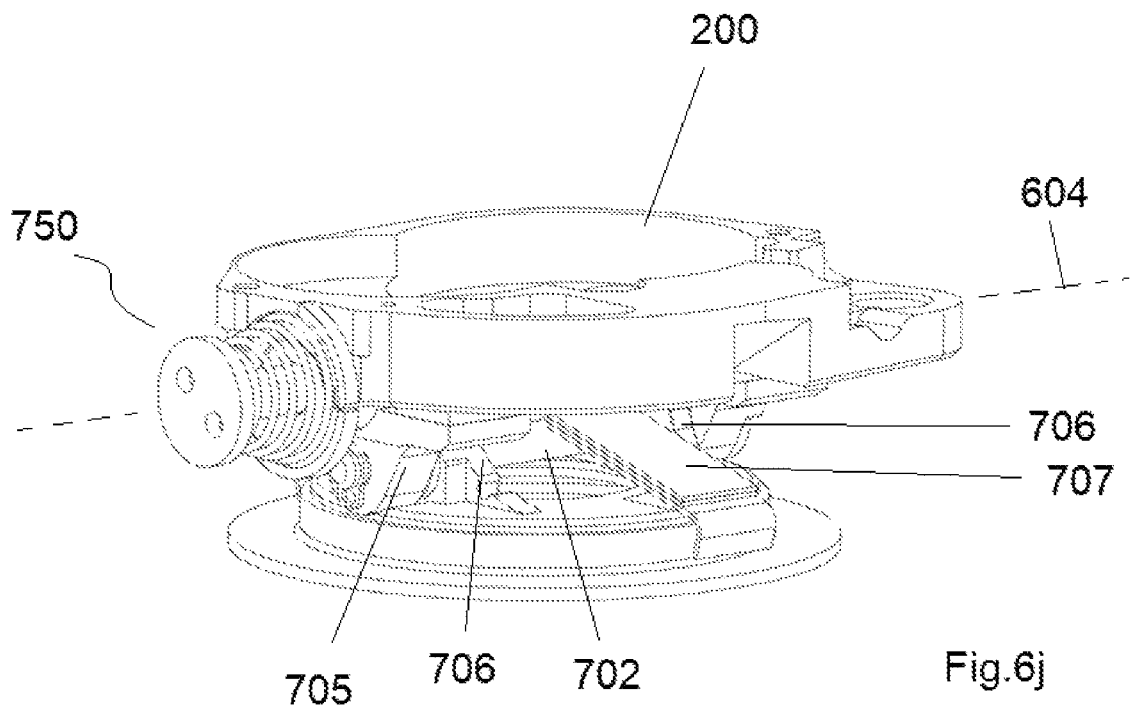
FIGS. 6j to 6v illustrate an alternative embodiment of the wrist assembly.

As illustrated in FIGS. 6*c* and 6*d*, the locking arrangement 650 consists of three primary components; static lock apertures 652, a spring-loaded lock bolt 654, and a lock button 656. The lock bolt 654 is mounted on the underside of the base chassis 200 and oriented substantially parallel with the hinge axis 604 of the wrist hinge/flex mechanism. The lock bolt 654 is slidable in an axial direction between an unlocked position (FIG. 6*c*) and a locked position (FIG. 6*d*). Each of the axially spaced apart lugs 606 extending from the arm plate 600 on which the hinge pin 602 is mounted includes a plurality of static lock apertures 652 which in the illustrated example are three spaced apart curved notches in an upper edge of each lug. Alternatively, each lock aperture may be a through hole in a corresponding one of the lugs, a slot, a square notch, or the like. Furthermore, an opposed arrangement can also be envisaged wherein the lock bolt is mounted on the arm plate and the static lock apertures are provided by the base chassis. The lock apertures 652 are indexed to correspond to predetermined locking angles of the wrist relative to the limb socket/arm of a user, i.e. a different rotational position of the base chassis 200 with respect to the arm plate 600 about the hinge axis 604.

The lock bolt 654 is slidable in an axis perpendicular to the array of lock apertures 652 and is generally of a shape which would lock into the apertures, preventing the base chassis 200 rotationally moving relative to the arm plate 600 about the hinge axis 604. The lock bolt 654 also has a pair of axially spaced apart gates 660,662 which allows the lugs to pass through the gates of the lock bolt 654 when the same is in the unlocked position and in turn allowing rotation between the base chassis 200 and the arm plate 600 about the hinge pin 602.

The lock bolt 654 is moved from the unlocked position to the locked position, and vice versa, by depressing the lock button 656. The lock bolt 654 is urged towards the lock button 656 but is not rigidly connected thereto. The lock button 654 is slidably coupled to the base chassis 200 and is urged away from the lock bolt 654 by a compression spring 658 towards a parked position.

As illustrated in FIGS. 6e to 6i, the lock button 656 comprises, or is coupled to, a track element 657 comprising a track 659 for engagement with an elongate and resilient member 661, e.g. a leaf spring, having a follower element 663 at a free end region thereof which follows the track of the tracked element 657. The track element 657 is slidably coupled to the lock bolt and an end region of the resilient member 661 distal the follower element 663 is fixed with respect to the base chassis 200.

The lock button 656 and track element 657 cycle between two positions corresponding to the locked and unlocked positions of the lock bolt 654 by being depressed by a user. As illustrated in FIGS. 6e to 6i, a position of the track element 657 is controlled by the leaf spring 661. The leaf spring 661 is allowed to flex in a direction approximately perpendicular to the axis of travel of the lock button 656. The track element 657 has two stable positions; locked and unlocked.

From the locked stable position (FIG. 6e), the button is pressed, causing the follower element 663 of the leaf spring 661 to slide up an unlocking path of the track and bend off the central axis (FIG. 6f). At the top of the unlocking path there is a pocket which the leaf spring springs into, as the button is released and urged away from the lock bolt by the compression spring 658, the follower element of the leaf spring is captured by a stop surface 665 of the track as the leaf spring straightens up (FIG. 6g). The lock bolt 654 is now in the unlocked position and the track element 657 is in a corresponding unlocked position. If the lock button is depressed again, the follower element 663 of the leaf spring 661 engages an angled surface of the track and is urged into a further depression in the track (FIG. 6h) defined by a further unlocking path of the track. When the lock button is released again, the leaf spring is urged down the further locking path of the track to return to the locked position (FIG. 6i).

In the unlocked position, the lock button 656 keeps the lock bolt gates 660,662 aligned with the edge of the lugs 606 and the lock apertures 652, allowing free rotation of the hand relative to the arm about the hinge axis 602. When the lock button 656 is in the locked position, the lock bolt spring urges the locking portion of the lock bolt to interface with a pair of the lock apertures. If the lock apertures are not perfectly aligned at the point the lock button is moved to the locked position, the lock bolt is spring-loaded and will drop into the next available aperture as the wrist is flexed.

The 'push-push' locking arrangement according to certain embodiments of the present invention allows a user with one or two prosthetic hands to efficiently select/adjust and lock a rotational position of the hand relative to the residual limb and with respect to the wrist flex axis, and also to release a locked rotational position to allow for wrist flex in either direction about the wrist flex hinge axis. The locking arrangement is also configured to spring into the next available locking position if the locking bolt is not aligned with a pair of locking apertures when in the locked position meaning the hand does not need to be perfectly aligned to latch the lock.

An alternative locking arrangement may be for the lock button to be rigidly coupled to the lock bolt to slide therewith between locked and unlocked positions and urged by a spring towards the locked position. However, such an arrangement would require a user to keep the button depressed with an able hand during rotation of the prosthetic hand relative to the limb socket/arm.

Figure 6K:
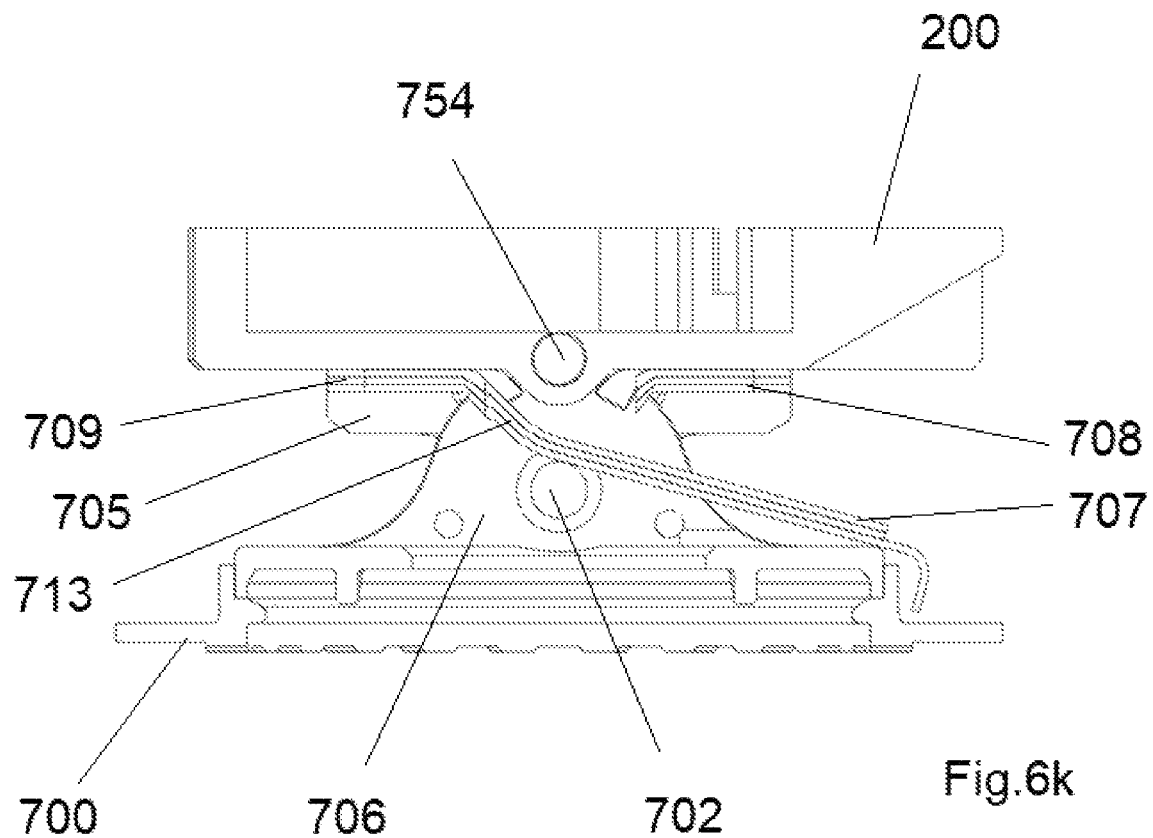
Figure 6L:
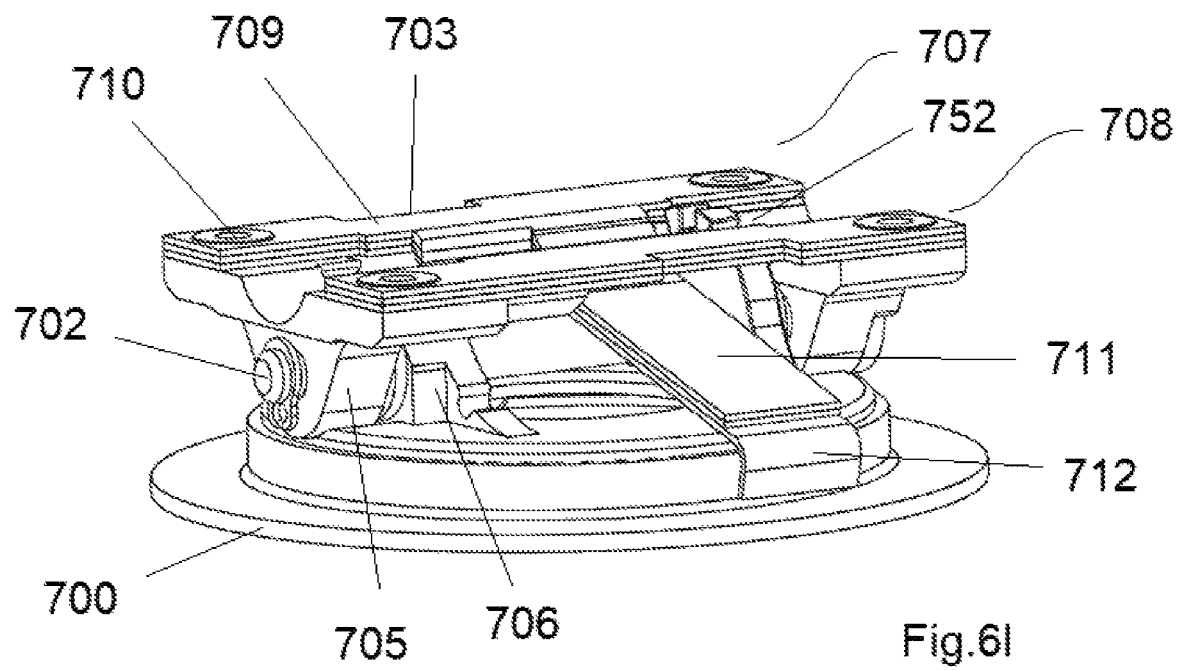

An alternative embodiment of the passive flex arrangement of the wrist assembly is illustrated in FIGS. 6j to 6m. Aptly, a pair of leaf springs 707,708 are mounted between the base chassis 200 and the lugs 705,706. Each leaf spring comprises a substantially planar and elongate main portion 709 which engages with flat upper surfaces of the lugs such that the main portion of each spring bridges the lugs on a respective side of the pin 702. As illustrated in FIG. 6l, the main bridge portion of a first one of the springs is disposed on one side of the pin 702 and the main bridge portion of the second one of the springs is disposed on the other side of the pin 702. Each end region of each elongate main portion has a through hole 710 to allow a suitable fixing, e.g. a bolt, to pass through the main portion of each spring when attaching the base chassis 200 to the outer lugs 705 to thereby sandwich the main bridge portions of the springs therebetween.

An elongate leg portion 711 extends inwardly towards pin axis and downwardly from the main portion 709 of each leaf spring 707,708 such that it passes over the hinge pin 702 and a free end region 712 thereof engages with the arm plate 700 at an opposite side of the hinge pin to the main portion from which it extends. The leg portion is oriented substantially perpendicularly to the main portion. The leg portion 711 is angled downwardly by around 5-85 degrees, aptly around 15 degrees, with respect to the planar main portion 709 when the base chassis is in the neutral position, as illustrated in FIG. 6k. Aptly, the leg portion 711 is coupled to the main portion 709 by an intermediate portion 713 which is angled downwardly by around 50 degrees to the planar main portion 709 such that it passes under and clears the locking element 754.

To allow the wrist assembly to flex by around at least 30 degrees to either direction, the planar main portion 709 of each spring, and a corresponding portion of the base chassis 200, comprises a notch 703 in its outer edge to accommodate the leg portion 707 of the other spring at full flex of the wrist.

Aptly, each of the leaf springs is configured such that the free end regions 712 thereof engage the arm plate 700 when the base chassis 200 is in the neutral equilibrium position, as illustrated in FIG. 6k. The free end region of the leg portion is bent downwardly to avoid sharp ends of the spring otherwise contacting and compromising the integrity of the soft glove portion surrounding the mechanics of the hand. This end portion could alternatively be bent 180 degrees (like a hair pin) for the same reason.

Aptly, the planar main portion of each leaf spring is around 38 mm long and around 6-7 mm wide. The intermediate portion is around 5 mm long and the leg portion is around 20 mm long. The intermediate portion and leg portion are around 7.5 mm wide. Each leaf spring is around 1.2 mm thick.

The leaf springs are aptly laminated, i.e. they each comprise two or more unconnected layers which are allowed to slide over each other during flexion to thereby reduce stress in the material which in turn reduces fatigue during flexing and minimises/eliminates the risk of spring failure in use. The leaf springs 707,708 are aptly made of a spring steel or other suitable material. Aptly, each spring is a linear leaf spring. The leaf springs according to certain embodiments of the present invention allow the wrist assembly to be more compact (shorter) than conventional wrist assemblies which rely on coiled torsion springs for example, whilst providing sufficient torque.

The base plate 200 is adapted to rotate +/− around 30 degrees about the hinge axis relative to the flat neutral plane. When the rotational force is removed from the base chassis, the compressed spring urges the base plate back to the neutral position with respect to the arm plate. Aptly, the two linear leaf springs 707,708 are configured such that one resists flexion and the other resists extension and are adapted such that when one spring is being compressed, the other spring decouples from the base chassis and provides no resistance to the spring being compressed. The only time both springs may be 'active' is +/− around 5 degrees to either side of the neutral plane.

As illustrated in FIGS. 6m to 6v, an alternative form of locking arrangement 750 according to certain embodiments of the present invention includes a lock button 756 depressible by a user and a driving cam member 766 coupled thereto by an elongate portion 780 slidably mounted in an aperture of a fixed support portion 768. The driving cam member 766 may be attached by suitable means to the elongate portion which extends from the lock button or the button, elongate portion and driving cam member 766 may be integrally formed. The lock button 756 and in turn the driving cam member 766 are slidable in an axial direction with respect to an axis of the elongate portion 780 when the button is pressed by a user. The elongate portion 780 is oriented substantially parallel with the hinge axis 704. A compression spring 758, or other suitable resilient member, located between the lock button 756 and the support portion 768 urges the button, and in turn the driving cam, outwardly in the axial direction such that a user is pressing the button against a reaction force of the spring. A pair of opposed elongate rail elements 782 extend inwardly from the support portion 768 in a direction parallel to the elongate portion 780 and engage with a respective one of a pair of opposed notches/grooves 783 in the outer surface of the driving cam member 766 such that the driving cam member is slidable along the rail elements 782 when the lock button is pressed and released, whilst being rotationally constrained by the rail/notch arrangement.

The locking arrangement 750 also includes a driven cam member 767 which is coupled to an end of an elongate locking element 754 such that it is rotatable with respect to the locking element 754. The driven cam member 767 however also includes opposed notches/grooves 784 in its outer surface for sliding engagement with the rail elements 782. The locking element 754 is mounted on the underside of the base chassis 200 and oriented substantially parallel with the hinge axis 704 of the wrist hinge/flex mechanism. The locking element 754 is axially slidable along a lock axis 772 between an unlocked position (as depicted in FIG. 6r) and a locked position (as depicted in FIG. 6n). The locking element 754 is rotationally constrained by the base chassis 200.

Figure 6M:
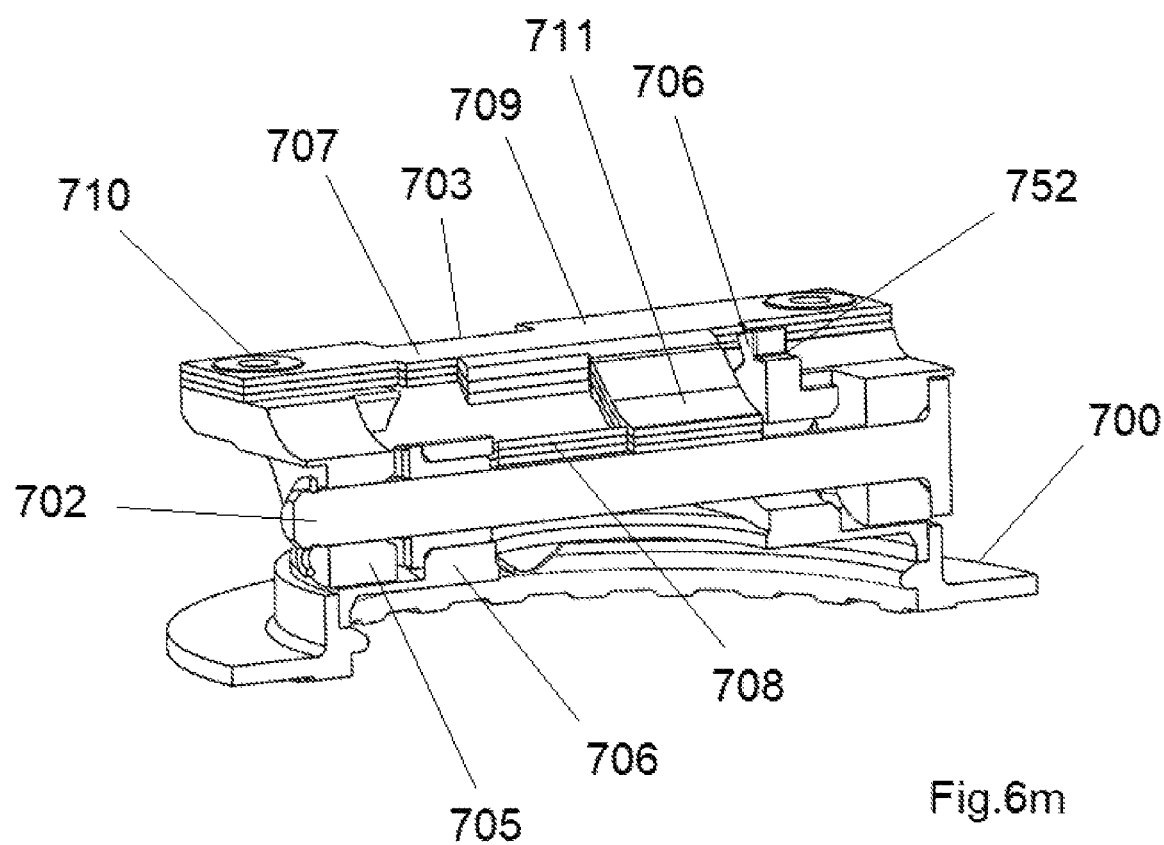
Figure 6N:
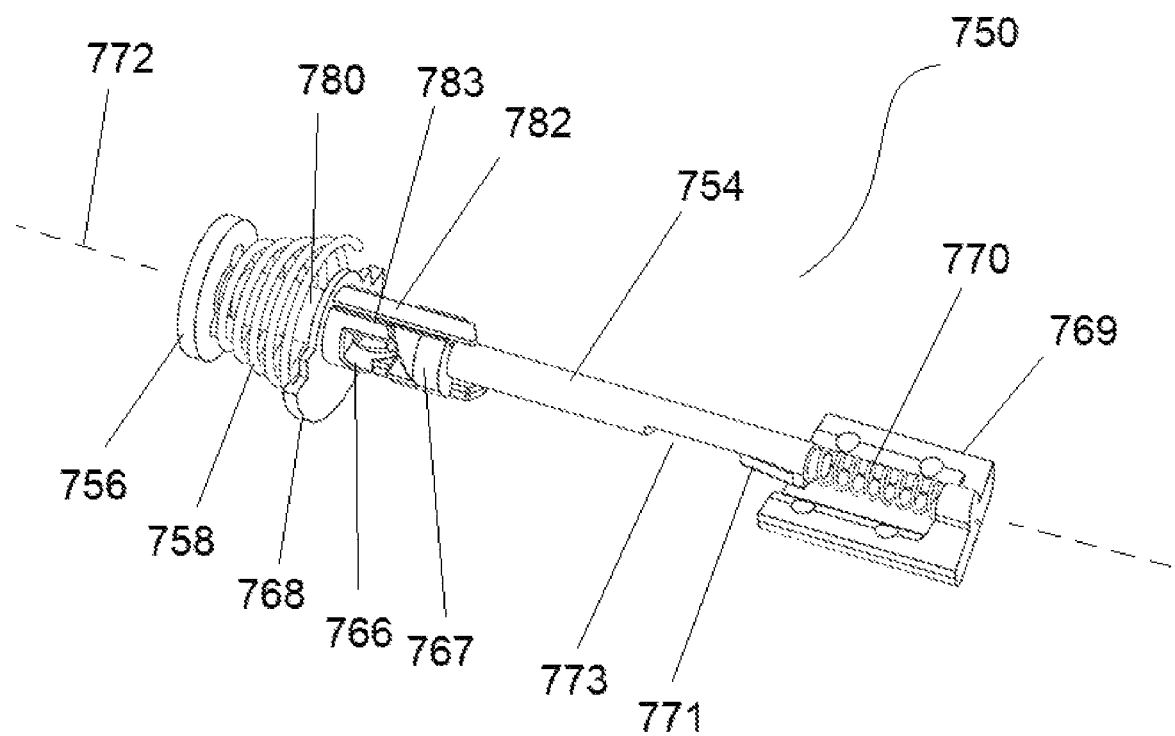

As illustrated in FIGS. 6l and 6m, one of the lugs 706 extending from the arm plate 700 on which the hinge pin 702 is mounted includes a plurality of static lock apertures 752 which, in a similar manner as illustrated in FIG. 6c, may be three spaced apart curved notches in an upper edge of the lug. Alternatively, each lock aperture may be a through hole in a corresponding one of the lugs, a slot, a square notch, or the like. Furthermore, an opposed arrangement can also be envisaged wherein the locking element 754 is mounted on the arm plate and the static lock apertures are provided by the base chassis. Aptly, the lock apertures are indexed to correspond to predetermined locking angles of the wrist relative to the limb socket/arm of a user, i.e. a different rotational position of the base chassis 200 with respect to the arm plate 700 about the hinge axis 704.

The locking element 754 is slidable along the locking axis 772 which is substantially perpendicular to the array of lock apertures 752 and is generally of a shape which would lock into the apertures, preventing the base chassis 200 rotationally moving relative to the arm plate 700 about the hinge axis 704. Aptly, the locking element 754 includes a tapered tooth element 771 or the like for engagement in a selected one of the lock apertures. The locking element 754 also has a gate 773 which allows the lugs to pass through the gate of the locking element 754 when the same is in the unlocked position and in turn allowing rotation between the base chassis 200 and the arm plate 700 about the hinge pin 702.

A second resilient member 770, e.g. compression spring, is provided between a second fixed support portion 769 and the end of the locking element distal to the driven cam member 767. The second spring urges the locking element towards the ends of the rail elements 782. The second spring 770 preloads the locking element 754 to the rotatable driven cam member 767 and also urges the driven cam member 767 against either the ends of the rail elements 782 (FIG. 6q) or the slidable driving cam member 766 (FIG. 6n) depending on the orientation of the driven cam member 767 with respect to the locking axis 772 and in turn the grooves/notches 784 of the driven cam member 767 with respect to the rail elements 782.

The first spring 758 preloads the lock button 756 and thus the driving cam member 766 such that the driving cam member 766 rests on the flanged face of the fixed housing portion 768. Pressing the lock button 756 allows the driving cam member 766 to move away from the flanged face along the locking axis 772.

The driving cam member 766 and the driven cam member 767 are substantially circular in cross section and each include at least one angled engagement surface such that when the engagement surface of the driving cam member engages the angled engagement surface of the driven cam member, the driven cam member is forced to rotate about the lock axis. Aptly, as illustrated, each of the cam members comprise a plurality of angled engagement surfaces, and aptly including at least one curved engagement surface. The engagement surfaces of the driving cam member 766 and the driven cam member 767 are angled in such a way to allow the linear motion of the driving cam member 766 to convert efficiently to rotation motion of the driven cam member 767 at quarter turns. Aptly, the engagement surfaces are angled by around 60 degrees.

FIG. 6n shows the locking mechanism in the locked position. In this position, the lock button 756 is in a fully out position so that the driving cam member 766 is resting against the flanged face of the fixed support portion 768. This is held in place by the first spring 758. The driven cam member 767 is orientated such that the grooves/notches 784 provided therein are allowed to slide over the rail elements 782. The driven cam member 767 is resting against the driving cam member 766 and the locking element 754 is resting against the driven cam member 767 due to the action of the second spring 770. The tooth element 771 of the locking element 754 is within a selected one of the lock apertures 752 of the lug 706. This prevents the base plate 200 rotating about the hinge axis with respect to the arm plate 700.

Figure 6O:
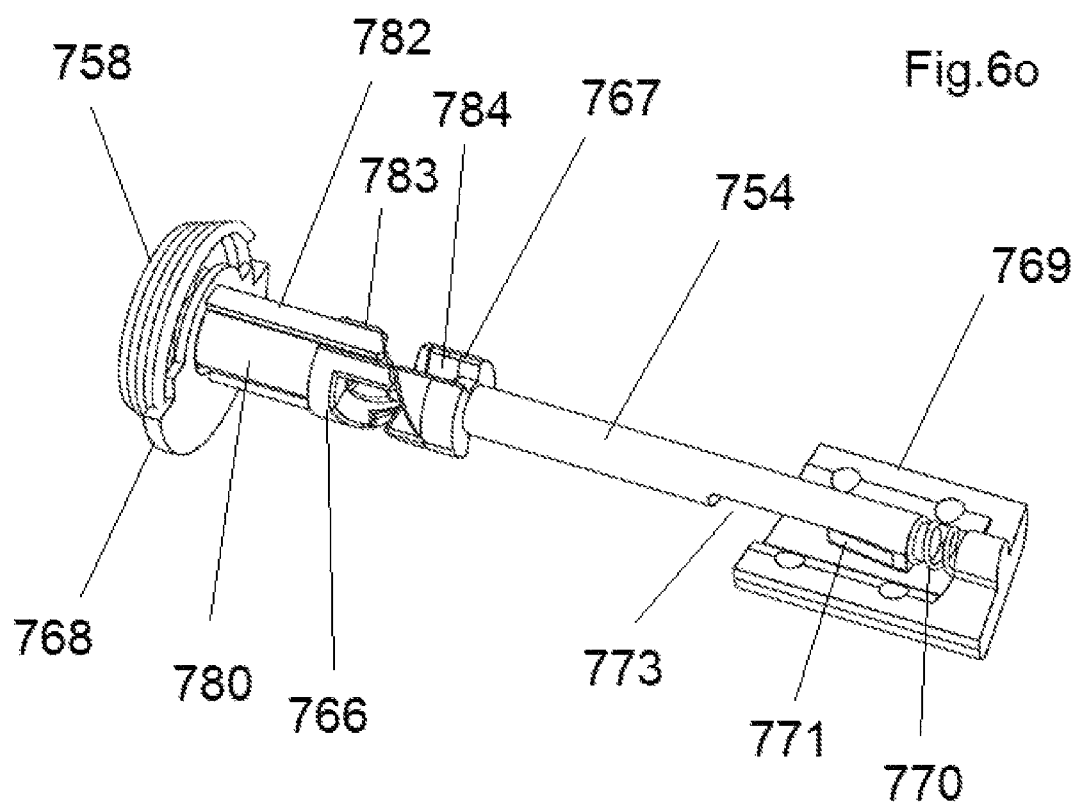

To unlock the wrist arrangement, the user presses the lock button 756 which in turns axially moves the driving cam member 766 along the rail element 782 in a direction of the lock axis 772. The driving cam member 766 pushes the driven cam member 767 along the lock axis. The driven cam member 767 is prohibited to rotate until the grooves/notches 784 therein are clear of the rail elements 782, as illustrated in FIG. 6o.

Figure 6P:
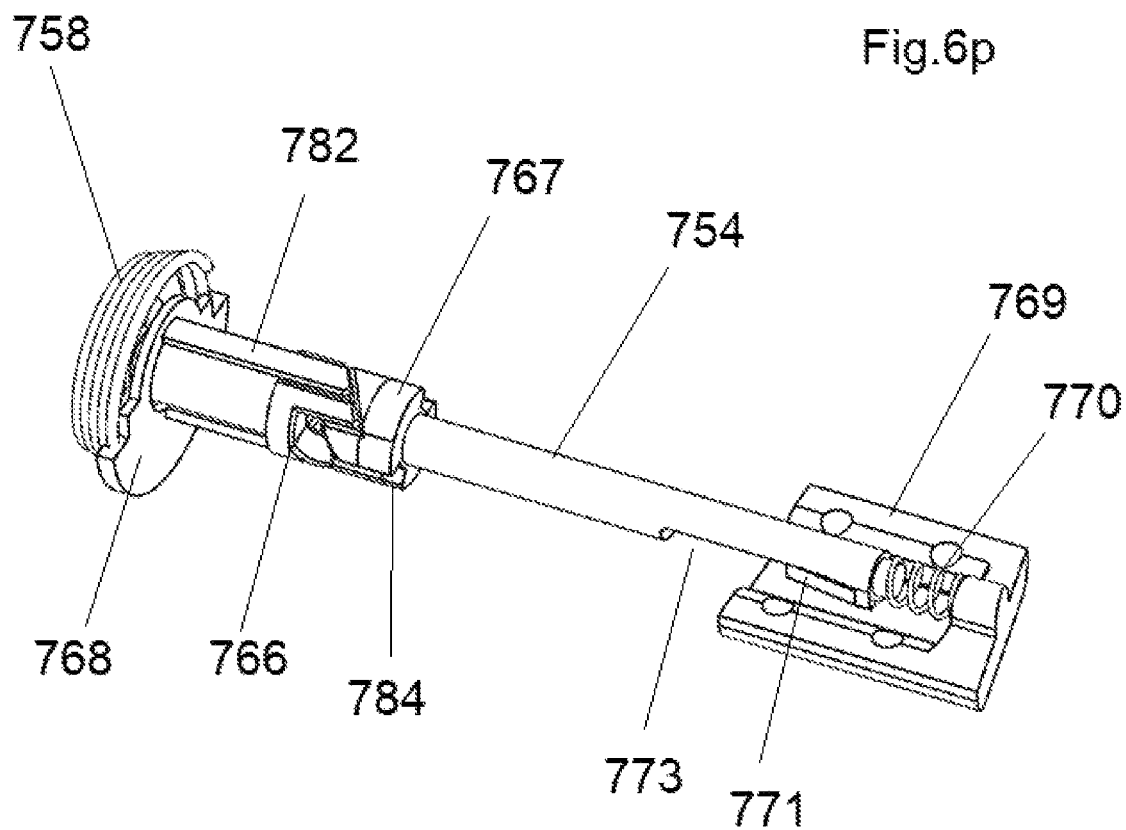

Once the grooves 784 of the driven cam member 767 are clear of the rail elements 782, the driven cam member 767 rotates until the teeth elements thereof are stopped by the correspondingly shaped teeth elements of the driving cam member 766, as illustrated in FIG. 6p. The rotation is due to the angled/sloped surfaces of the engaged teeth elements of the cam members 766, 767 and the urging force provided by the second spring 770.

Figure 6Q:
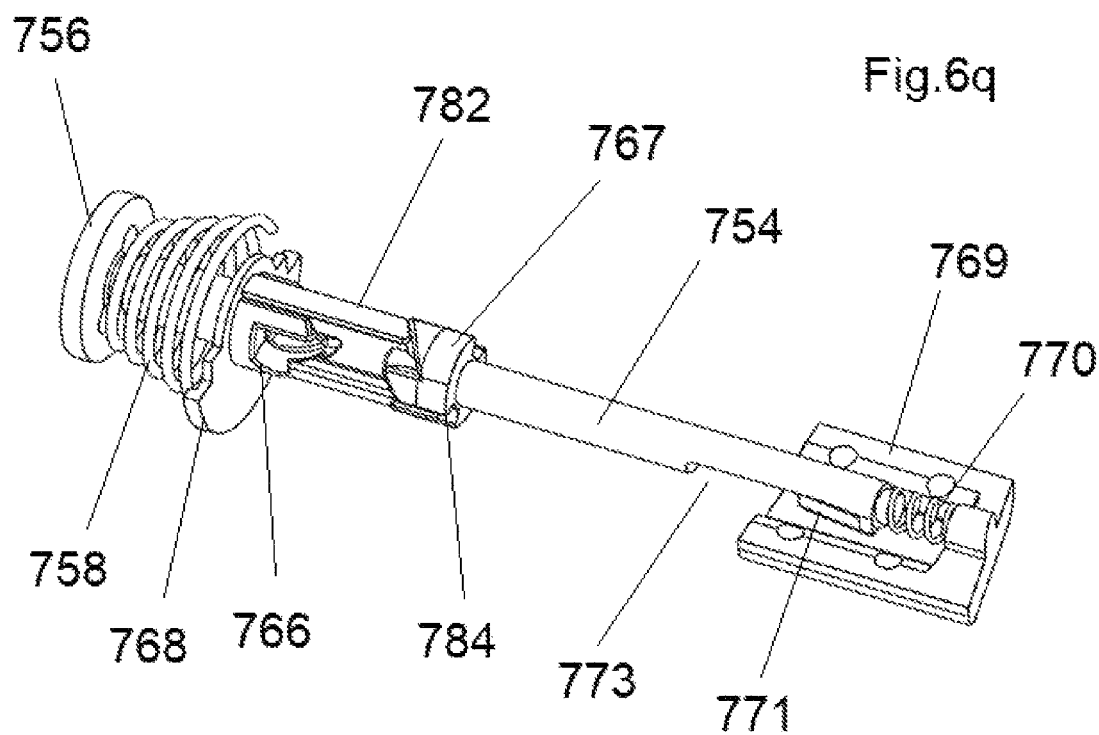
Figure 6R:
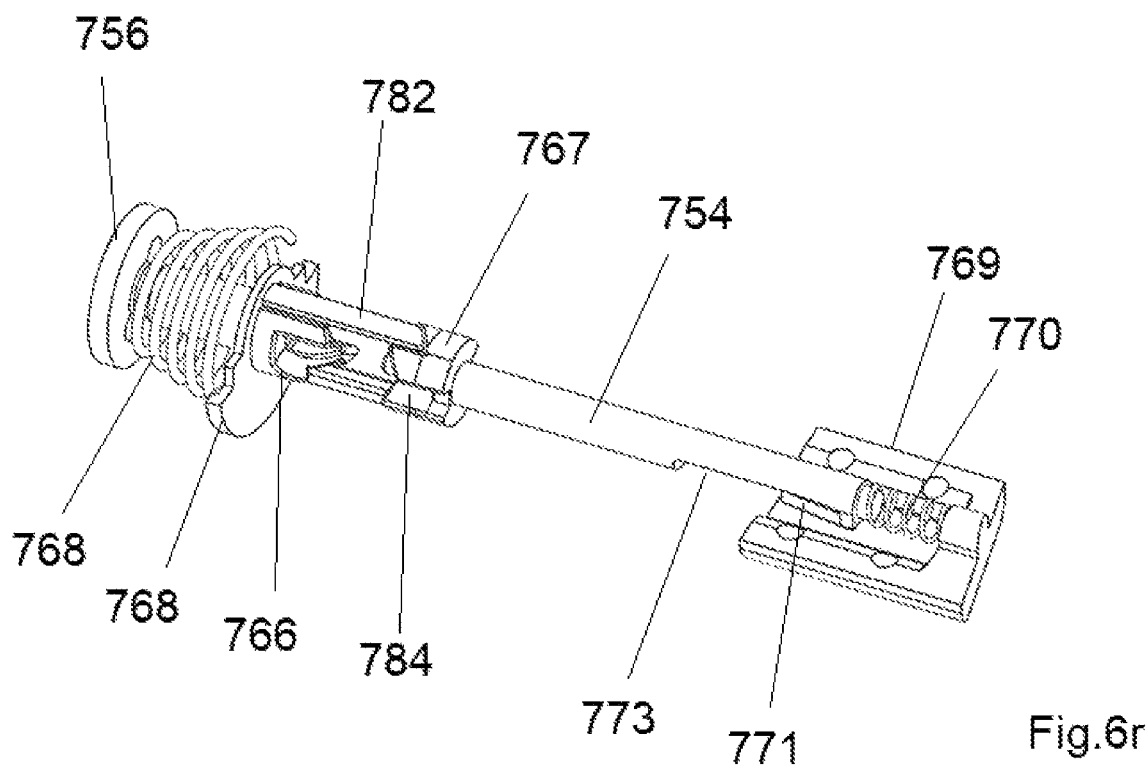

Once the lock button 756 is released, the first spring 758 returns the lock button and the driving cam member 766 back to its resting position, as illustrated in FIG. 6q. The driven cam member 767 is now allowed to rotate further until the rail elements 782 engage with the grooves 784 of the driven cam member 767 prevent any further movement, as illustrated in FIG. 6r. The rotation is due to the angled/sloped surfaces of the engaged teeth elements of the cam members 766, 767 and the urging force provided by the second spring 770. At this position, the tapered tooth element 771 of the locking element 754 is clear of the lock apertures 752 of the lug 706 and in turn the base chassis 200 is allowed to rotate about the hinge axis 704 with respect to the arm plate 700.

Figure 6S:
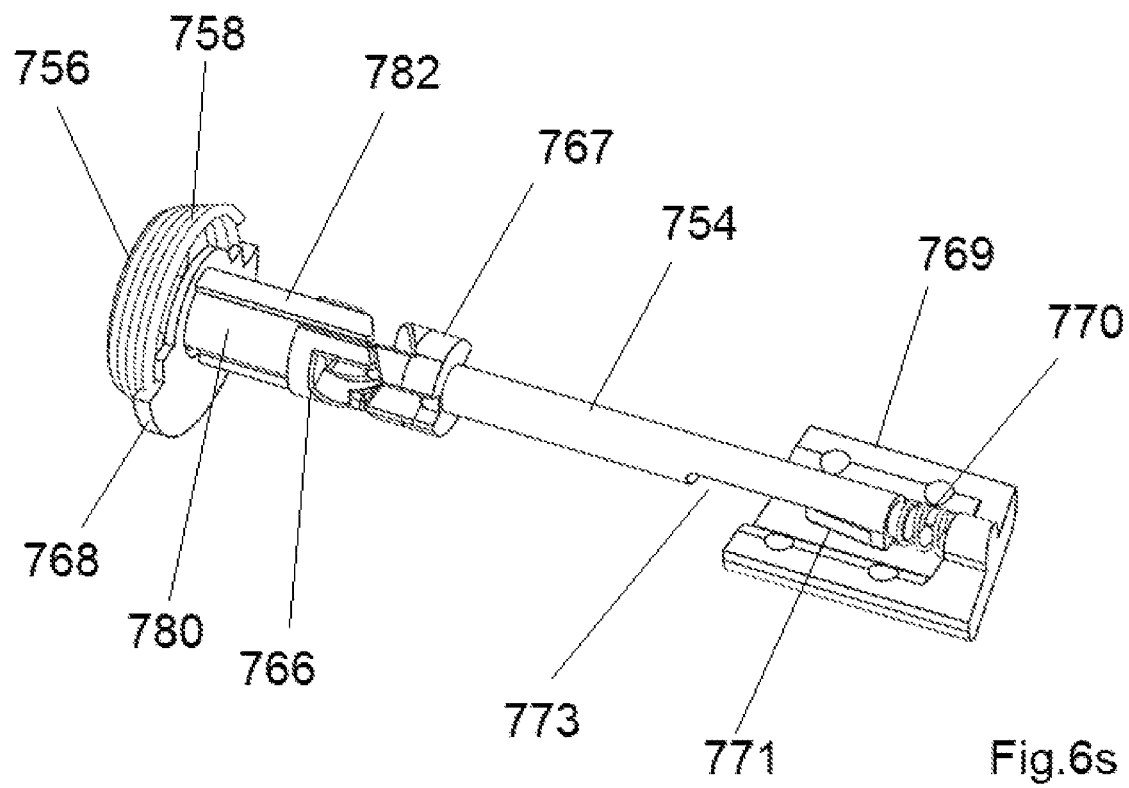
Figure 6T:
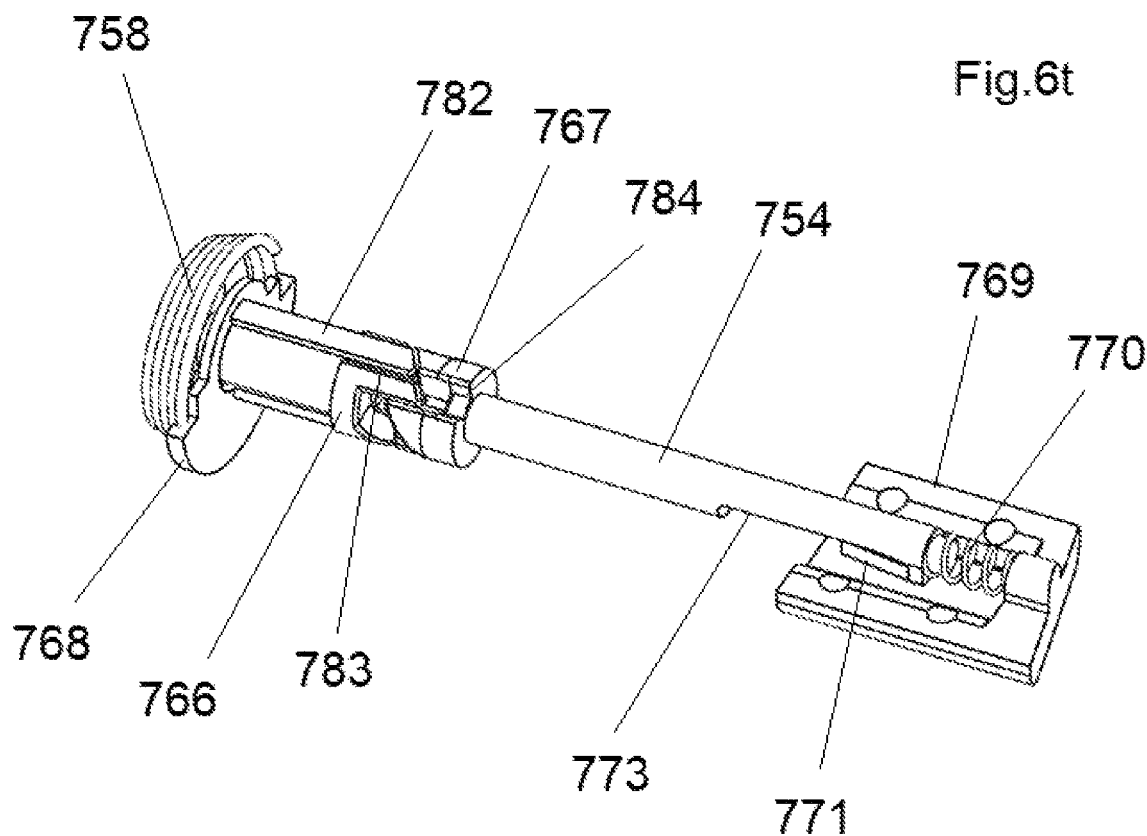

To lock the wrist, the user presses the lock button 756 which axially moves the driving cam member 766 along the rail elements 782 in a direction of the lock axis 772 until it engages with and pushes the driven cam member 767 along the lock axis. The driven cam member 767 is prohibited to rotate until the grooves 784 thereof are clear of the rail elements 782, as illustrated in FIG. 6s. Once the grooves 784 are clear of the rail elements 782, the driven cam member 767 rotates until the teeth elements thereof are stopped by the teeth element/s of the driving cam 766, as illustrated in FIG. 6t. The rotation is due to the angled/sloped surfaces of the engaged teeth elements of the cam members 766, 767 and the urging force provided by the second spring 770.

Figure 6U:
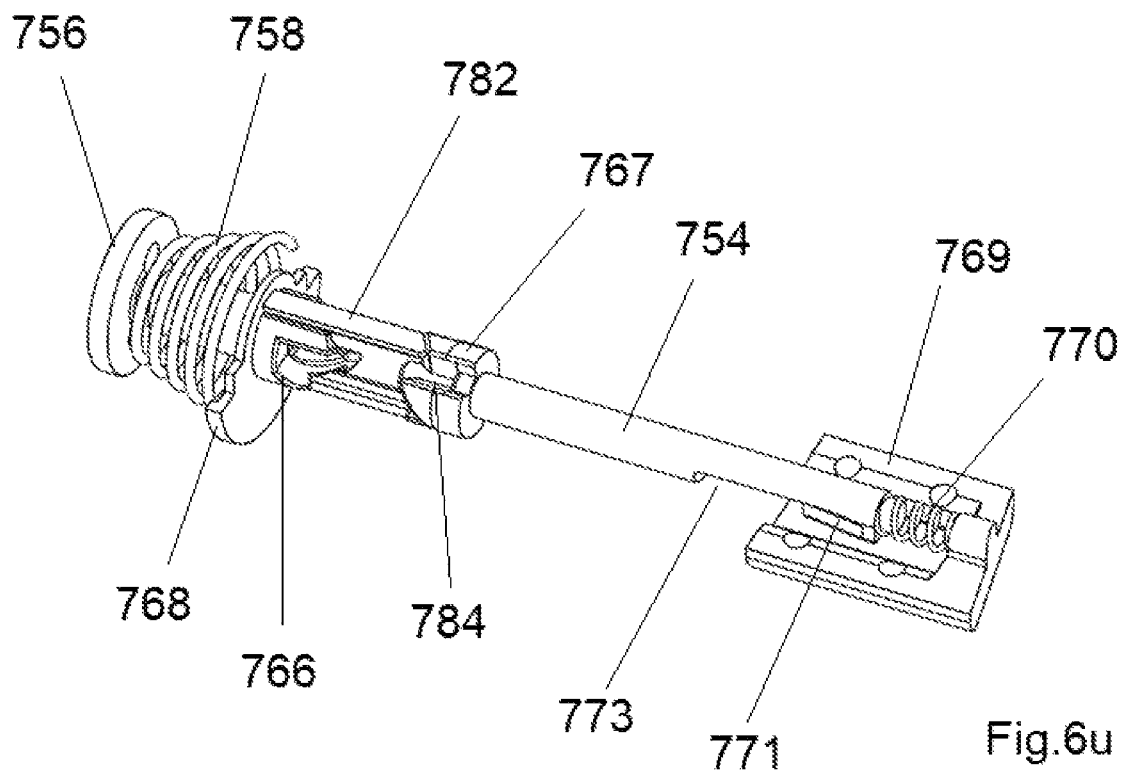
Figure 6V:
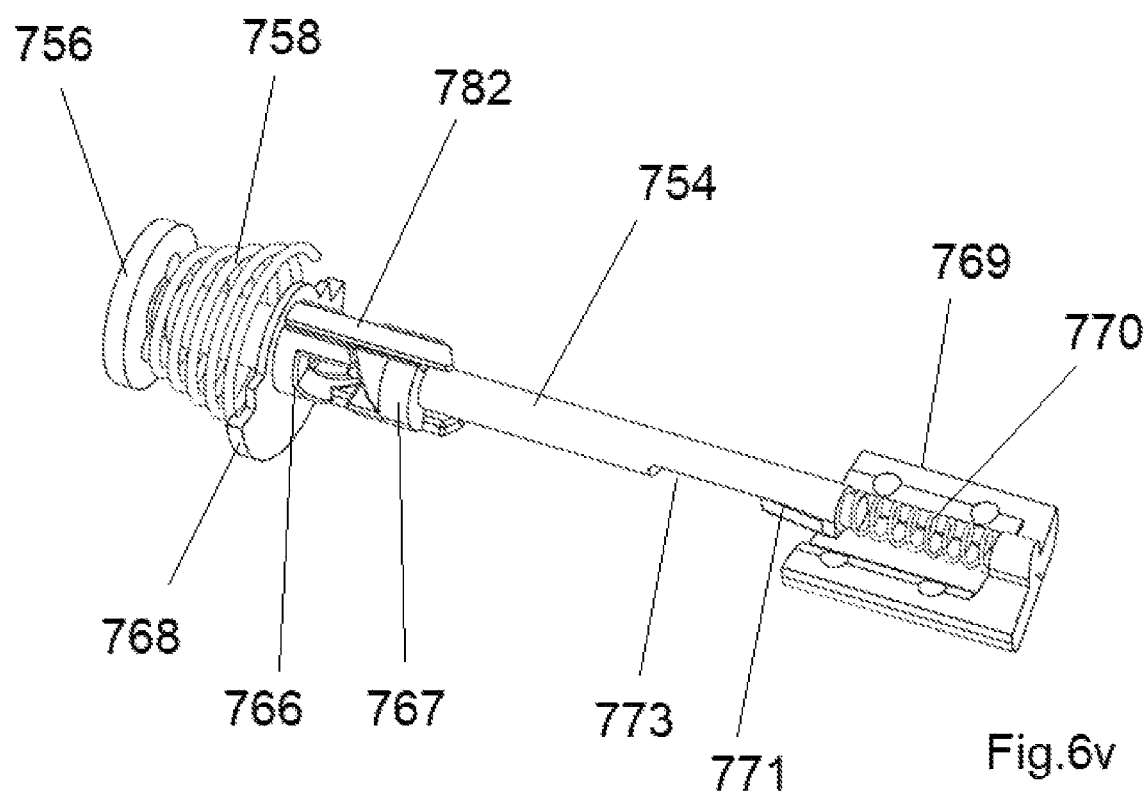

Once the lock button 756 is released, the first spring 758 returns the lock button and the driving cam member 766 back to its resting position, as illustrated in FIG. 6u. The driven cam member 767 is now allowed to rotate further, as a result of being engaged with and rotatably urged by the tapered end region of the rail elements 782, until the grooves 784 thereof align with the fixed rail elements 782. The driven cam member 767 is then slid back until it rests on the driving cam member 766 when urged by the second spring 770, as illustrated in FIG. 6v. The locking element 754 is in the locked state, wherein the tooth element 771 of the locking element 754 is within a selected one of the lock apertures 752 of the lug 706 to thereby prevent the base chassis 200 rotating with respect to the arm plate 700.

Control System

Figure 7A:
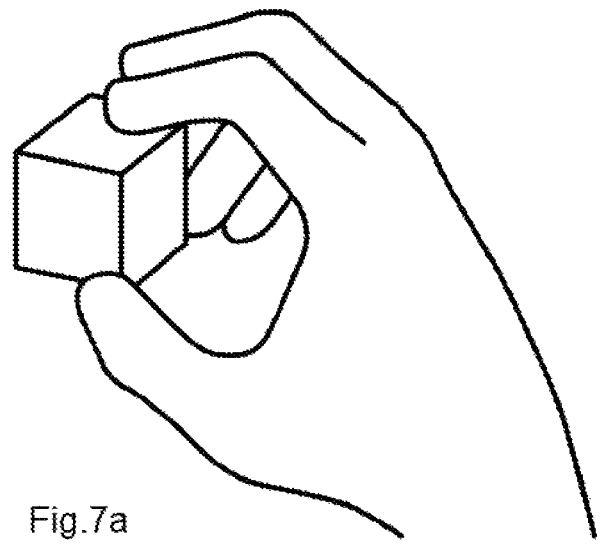
FIGS. 7a to 7d illustrate a variety of different grips which a user may wish to select.
Figure 7B:
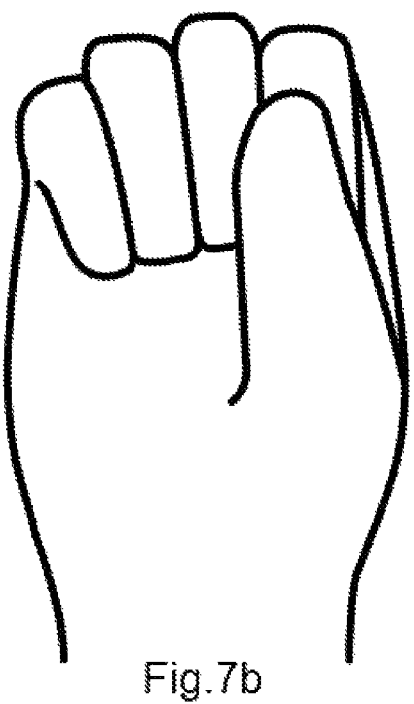
Figure 7C:
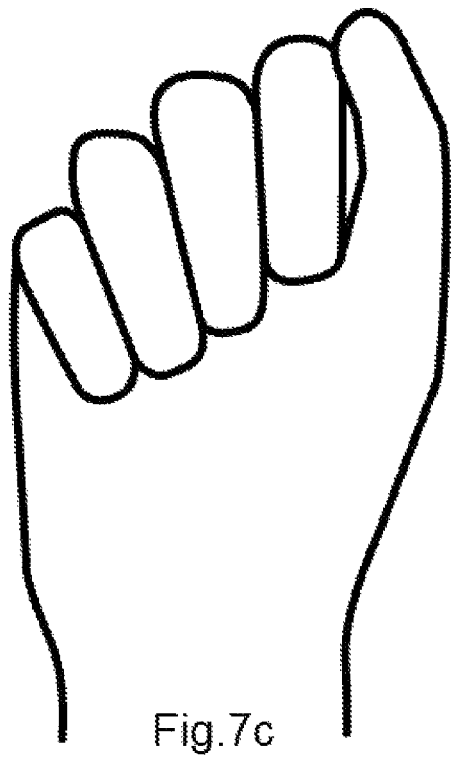
Figure 7D:

The prosthetic hand 100 according to certain embodiments of the present invention has six actuators (a respective one for flexing and extending each of the four fingers, one for flexing and extending the thumb, and one for rotating the thumb between opposed and non-opposed positions) which are selectively driven in a number of different configurations to deliver a wide array of desirable grips, a selection of which are illustrated in FIGS. 7a to 7d. FIG. 7a illustrates a tripod grip wherein the thumb is in an opposed position and is partially closed to grip an object, and the index and second finger are partially closed to grip the object, and the third and fourth fingers are fully closed. If nothing is grasped, the index finger, second finger and thumb tips should all converge and stop. FIG. 7b illustrates a power grip wherein all the fingers are fully closed followed by the thumb in a closed, opposed position. FIG. 7c illustrates a key grip wherein the fingers are all partially closed and the thumb is in the extended, non-opposed position. FIG. 7d illustrates a point grip wherein the second, third and fourth fingers are closed, the index finger is extended, and the thumb is in the flexed, non-opposed.

The control system can be broken down into four areas; Mode Configuration, Grip Selection, Grip Control and Digit control.

Mode Configuration Mode configuration concerns the variables defined primarily by the clinician to customise the device to the clinician and functional needs of the user/s. These can be the type of inputs, the amplification on the input signals and threshold levels at which the digits of the device start to move. It is possible to fully customise which grips are selected from a particular input. In addition to the clinician settings, the device according to certain embodiments of the present invention has two primary modes of operation; dynamic and latched, both of which have their advantages.

When in dynamic mode, the thumb parks in an open position, midway between opposed and unopposed positions, and the user can automatically alternate between opposed and unopposed grips (for example between the opposed grips of FIGS. 7a and 7b and the non-opposed grips of FIGS. 7c and 7d) with myo controls only, e.g. with an open/open cycle when the hand is in the open position, but this could equally be performed with externally control systems such as pattern recognition. Dynamic operation provides the user with the ability to cycle between unopposed and opposed grips using only myo electric signals. This can be advantageous for a user with reduced mobility or using two prosthetic hands.

When in latched mode, the thumb is parked in either open unopposed or open opposed and an open/open cycle performed by the user via the myo controls cycles between a plurality of grips which share the same thumb rotational start (parked) position. The thumb may be rotated using the rocker switch which in turn activates the thumb rotation motor, e.g. tap left the thumb moves left, tap right and the thumb moves right to thereby be in a desired parked position for one a plurality of corresponding grips to be selected by the user. Alternatively, a user could use co-contraction signal, 2× simultaneous myo signals, to activate the thumb rotation motor. Latched operation gives access to a relatively wide range of grips, but requires additional input from the user in addition to myo electric signals.

According to certain embodiments of the present invention, the user may switch between dynamic mode and latched mode by an additional input, other than using myo signals, in a non-complex, efficient and intuitive manner. For example, the user may press all four finger FSR's simultaneously or activate the thumb rocker switch twice in a given time frame by applying a lateral force to the thumb assembly either with an able limb or by tapping the thumb on a surface. As such, the user can swap between dynamic and latched mode, if required, with a non-complex, efficient and intuitive input.

There are a number of different predetermined hand grips, such as those illustrated in FIGS. 7a to 7d, and thus predetermined positions of the fingers 102 and thumb 104, stored in a memory of the controller. These different grips may be 'factory' default grips prestored in the memory during manufacture and calibration of the hand prior to sale, and/or custom grips configured by the user for a particular preference or requirement. All these grip definitions, along with other clinician settings, form the mode configuration global variable and are used during grip selection and grip and digit control.

Figure 8:
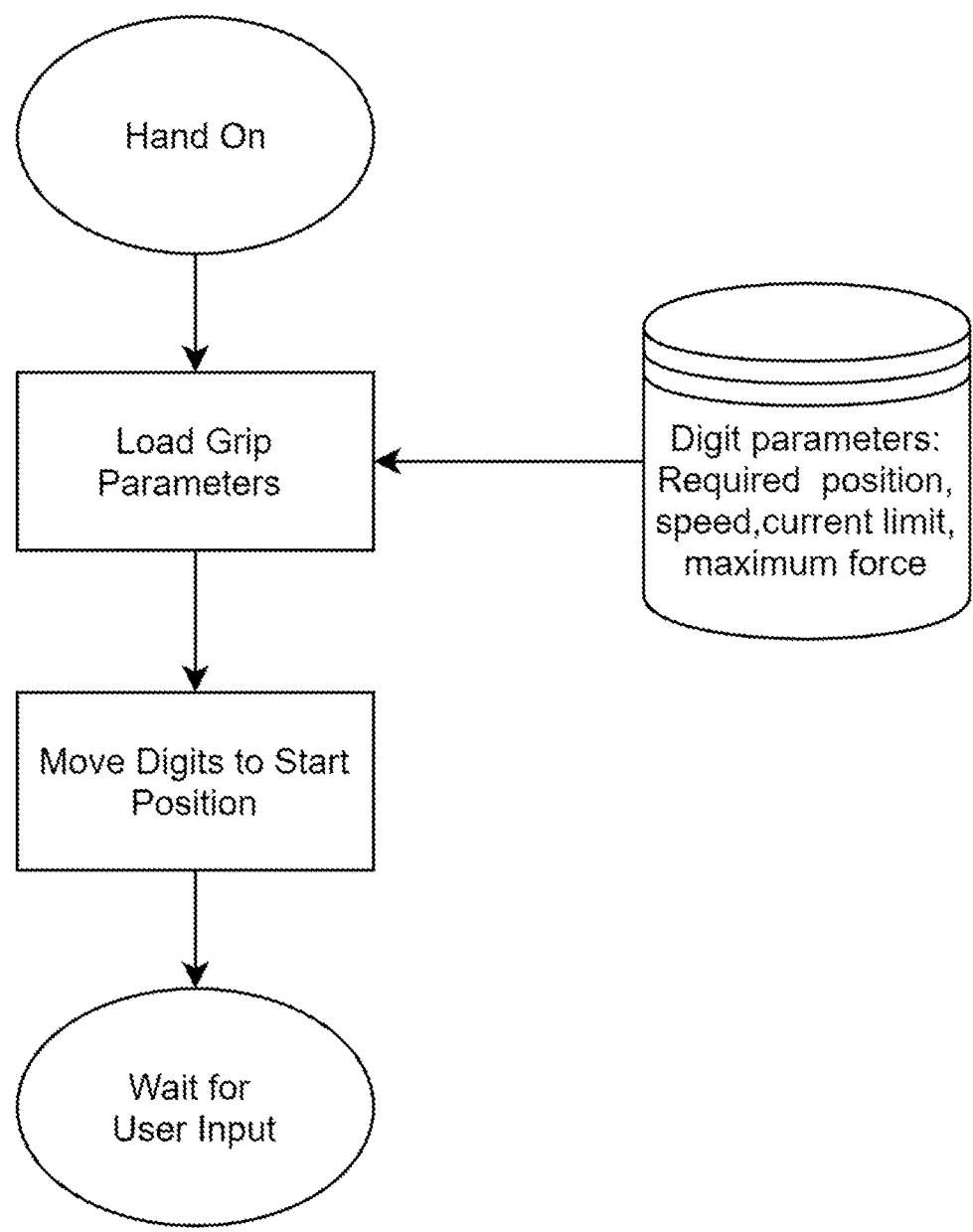
FIG. 8 illustrates an initialisation process of a control method according to certain embodiments of the present invention.

Mode configuration also dictates the 'power on' operation of the hand in terms of initialising at a default position or continuing from the last used state, as shown in FIG. 8. The hand does not require start-up calibration so any initial position for the digits could be used and the digits could optionally remain at the current positions.

Grip Selection

Grip selection is primarily performed by cycling through a predetermined list of grips using a known input. The preferred input is the open/open cycle myo signal when the hand is open which will cycle between at least two predetermined grips. This is a compromise between accessibility and ease of use. The longer the list, the more the user has to remember and the slower it is to access a particular grip.

Figure 9:
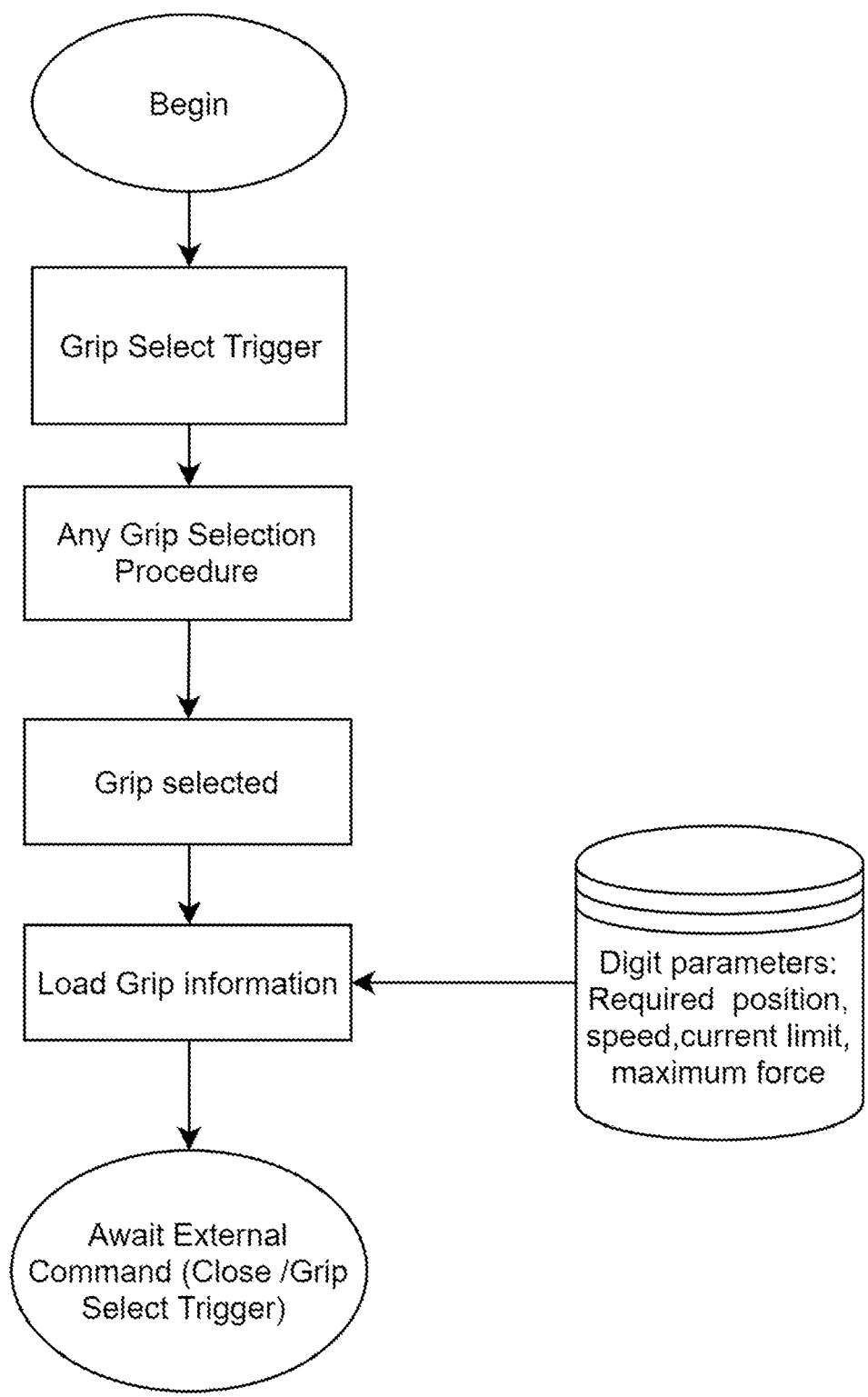
FIG. 9 illustrates a grip change process of the control method.

FIG. 9 illustrates a process used to change a grip according to certain embodiments of the present invention. The user is required to issue a grip selection trigger to differentiate it from normal open and close signals typically used for manipulating the hand. The grip selection trigger could be: hold open, open-open, co-contraction, RFID, onboard input/switch, external switch or pattern recognition. After the initial grip select trigger has been initiated by the user, additional signals may be sent to select a particular grip.

As described above, the prosthetic hand 100 according to certain embodiments of the present invention aptly has two modes of operation which control how the hand delivers a desired grip from an initial 'parked' position; a 'latched' mode and a 'dynamic' mode.

When the hand is in the 'latched' mode of operation and the hand (thumb and fingers) is open, the hand will park in one of a plurality of predetermined 'latched' park configurations each of which corresponds to grips which share an extended opposed or extended non-opposed thumb start position. For example, 'tripod' (FIG. 7a) and 'power' (FIG. 7b) grips both share a common extended opposed start thumb position, whereas 'key' (FIG. 7c) and 'finger point' (FIG. 7d) grips both share a common extended, non-opposed start thumb position. When a 'close' signal is received by the controller from the user, the first motor 210 will remain static and only the second motor 450 is operated to move the thumb 104 along the flexion/extension plane along with the fingers to deliver the desired grip. An 'open' myo signal will reverse the process and return the digits to the extended position.

When in the 'latched' park position, the thumb 104 can be moved from unopposed to opposed or vice versa by laterally moving the thumb 104 about the rocker axis 370 to trigger a one of the rocker switches 345,347 and actuating the first motor 210 accordingly. For example, if the thumb 104 is tapped laterally left or right, the thumb 10 will move to the alternate thumb position. In the current embodiment there are two thumb positions, but it is envisaged that numerous positions could be possible.

When the hand is in the 'dynamic' mode of operation and the hand is open, the thumb assembly 104 is parked in a position, aptly midway, between the opposed position and non-opposed position, i.e. at a position between the two rotational limits of the thumb about the hub axis 322. When in the parked 'dynamic' position, the thumb 104 is also in an extended position along the flexion/extension plane of the thumb. When a 'close' gripping signal is received by the controller from the user via electrode sensors in the limb socket, both the first motor 210 and the second motor 450 are operated simultaneously to move the thumb 104 both rotationally about hub axis 322 and along the flexion/extension plane to a desired position as selected by the user (as described further below). A corresponding 'open' signal received by the controller reverses the dual actuation process to move the thumb 104 back to the dynamic 'parked' position.

When the thumb 104 is away from its extended parked position, i.e. at a limit of its rotational movement about the hub axis 322 and not extended, an 'open' signal will only open the hand (extension of fingers and thumb) and any lateral movement in the thumb 104 is mechanically blocked or electrically ignored to prevent the rocker switches 345, 347 being triggered and the thumb 104 otherwise being moved from the opposed or non-opposed position.

In addition to the MYO electric signals and the lateral rocker switches on the thumb, a further method of operating the hand 100 according to certain embodiments of the present invention enables users to utilise a full range of grips using a relatively short instruction sequence. It also requires minimal cognitive effort to control the hand, particularly with respect to being able to locate infrequently accessed grips.

This control method uses the fingers and thumb 102,104 as switches/inputs to enable grip selection. According to certain embodiments of the present invention, the hand may be configured to use the force sensitive resistors on the digit tips as radio buttons. For example, pushing all four fingers onto a surface for one second could be used as an input to move the hand directly into a finger point grip.

Alternatively, or additionally, the fingers and thumb 102, 104 may be considered as three-way switches, with the finger or thumb states being straight, partially flexed, or fully closed, or analogue inputs by manually moving them. As described above, both the fingers and the thumb are able to passively flex from an open position to a closed position, while the respective linear potentiometer is able to read the position of the digit regardless of whether the respective motor is driven. It is envisaged that this could be for a simplified clinical adjustment, but the hand could also be configured to use this feature for grip selection.

The hand aptly includes a display, e.g. a touch screen, on the dorsal surface of the hand. In the current embodiment this is an e-paper screen, but could equally be an LCD, or OLED. The display may be configured to show the user which mode they are in, and even to change the order of grips. It is also envisaged that the display may be turned off when the user becomes proficient and no longer requires the grip confirmation.

The mode configuration global variables and the grip selection variables are used to select the correct grip. For example, as shown in FIG. 9, predetermined digit parameters (required position, speed, current limit, and maximum force) are loaded, and executed by the controller when a close signal is received from the user.

Grip Control

A grip may be represented by a sequence of instructions, essentially a list of waypoints that dictate the motion of the hand in response to an electromyography (EMG) signal, that will continue automatically as long as a signal is applied or a further signal may be required to step to the next stage of the sequence.

The required closing speed is determined from the amplitude of the myo-electrode signal provided by the user. The grip controller instructs each digit to move to the position required for the first step of the grip. Once the required conditions are satisfied, the grip controller requests feedback variables from each of the digits and initiates the next step of the grip in response to this feedback. Some grips require some digits to remain static until another digit has reached a particular position, this is handled by the grip controller and the instructions issued to the Digit Control logic.

This process is repeated until either the grip is completed, or the close signal is removed.

FIG. 8 illustrates the initialisation process at system start-up. At all times the hand will have a grip selected that will be performed given suitable open/close myo signals. On start-up, this may either be a factory default or user selected/last used grip pattern stored in a non-volatile memory. Associated with each grip is a parked position for each digit and these, along with sequencing information about finger movements to achieve the grip, will also be loaded. Additional information regarding motor current limit (related to motor torque and therefore grip force), maximum digit speeds, maximum force and auto-grip (described below with reference to FIG. 13) are aptly also loaded. For some grips, the motor torque for the thumb may take two values; a lower limit to ensure the thumb gearbox stays out of the high torque gear or the motive portion of the grip and then changing to a higher value when extra force is to be exerted. Alternatively, it may take a single value, such as an arbitrarily low value for handshaking, or as much as the electrical hardware can deliver for power grip where the gear change does not need to be delayed. The digit positions (5× flexion and 1× rotation) may be read directly from the linear potentiometers.

If the hand is not at a position compatible with the loaded grip, it should wait for an open signal to return it to the parked/start position. Alternatively, the hand may be considered to be in an intermediate position in the sequence and may respond to both open and close signals from the user.

Under normal circumstances, the grip sequence is aptly configured such that the digits will move unimpeded until they are brought into a position that they can exert force onto other digits or an object being gripped. When the grip opens it may be sequenced so that the digits will not clash and prevent the hand from opening.

Digit Control

Any combination of individual digits may be required to move to satisfy a control criterion. For automatically terminating the motion of the digit, one of three criteria will have to be met:

Target position achieved

Electrical current limit has been reached

Fingertip load achieved

The digits (fingers and thumb) will also stop in response to the user removing the is signal. Additional stage specific data may include:

Target speed, typically a scalar value of the maximum, used to enable increase user control on precision grips If electrical current limit has been reached for the fingers, should the power management high grip force stage be applied?

Should increased thumb force be applied at this stage?

Is grip maintenance required?

Auto move onto next step?

When the user indicates a change to the grip, all the associated control data is loaded.

Figure 10:
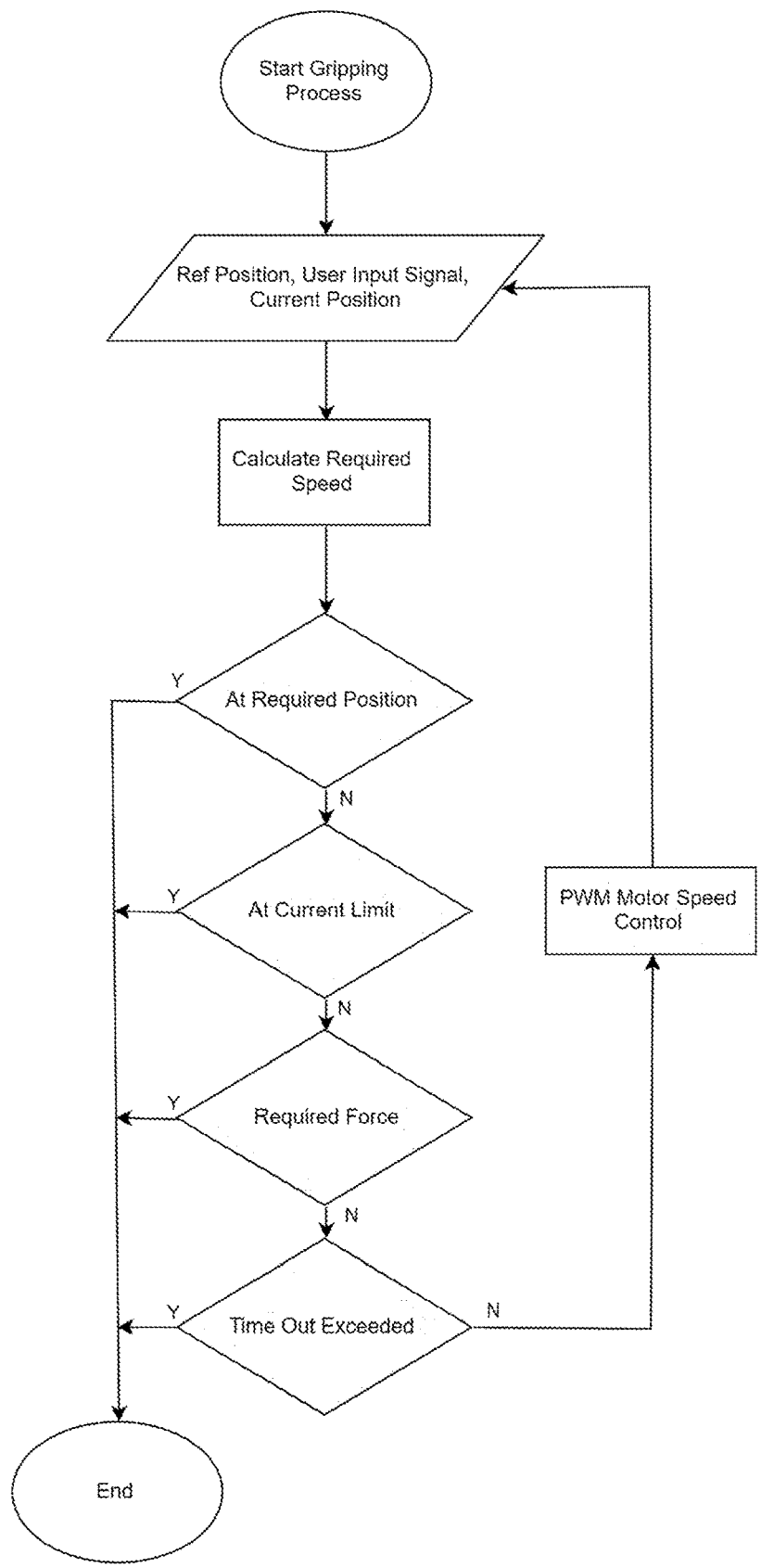
FIG. 10 illustrates a schematic representation of the digit motion control of the control method.

FIG. 10 illustrates a schematic representation of the digit control logic. For any given grip, the target position, current limit, and grip force limit are loaded from the stored grip definition. The required speed is determined from the motion sequence required to complete the grip and may also be a function of the amplitude of the myo signal provided by the user. The motor speed is determined from the Hall sensor on the motors, giving a finer resolution than the linear potentiometer. If the motor requires braking, then this may be achieved in an electronic manner by cross connecting the terminals. The required speed is adjusted according to the relative positions of the digits, synchronizing the motion of the fingers, by communicating with modules controlling the other digits. When the digit movement satisfies one of the exit criteria then it will stop. If the digit is the thumb, then this digit control phase may be repeated with a relatively high electrical current limit, forcing the gearbox 452 to change gear and allow the grip force to be increased significantly. The precise motor control required to accurately move the hand is facilitated by the combined use of the three parameters; finger position (as measured from the linear potentiometer), motor speed (as measured from the Hall sensor) and the digit tip force (as measured from the FSR).

Figure 11:
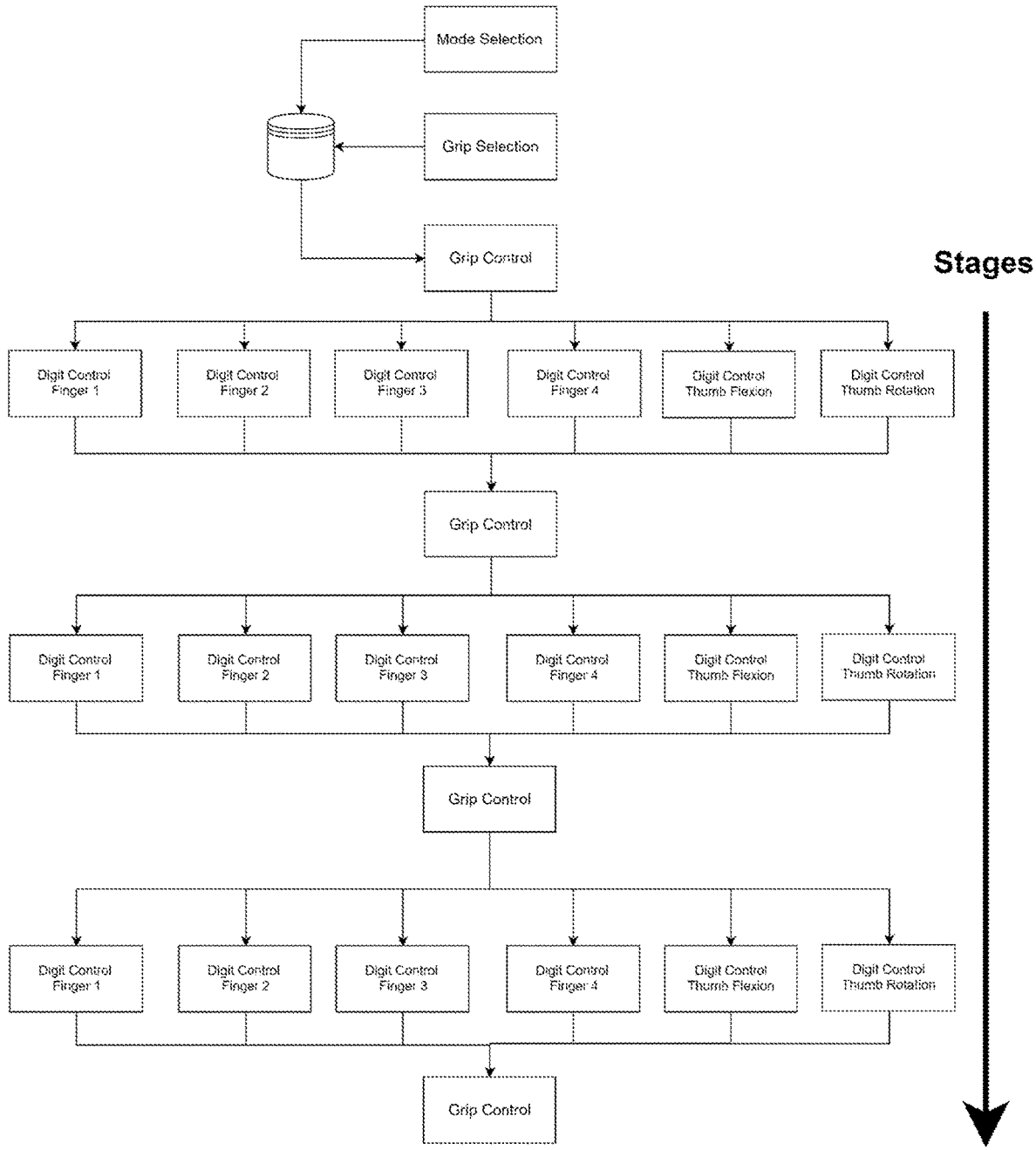
FIG. 11 illustrates the sequential stages of finger movement operation of the control method.

This process would work for the entire grip if all the fingers were to move at the same time. Many grips require the use of intermediate stages, such as power where the fingers will close before the thumb is moved inwards. In such cases the process must be repeated for each of the individual stages, as shown schematically in FIG. 11.

Figure 12:
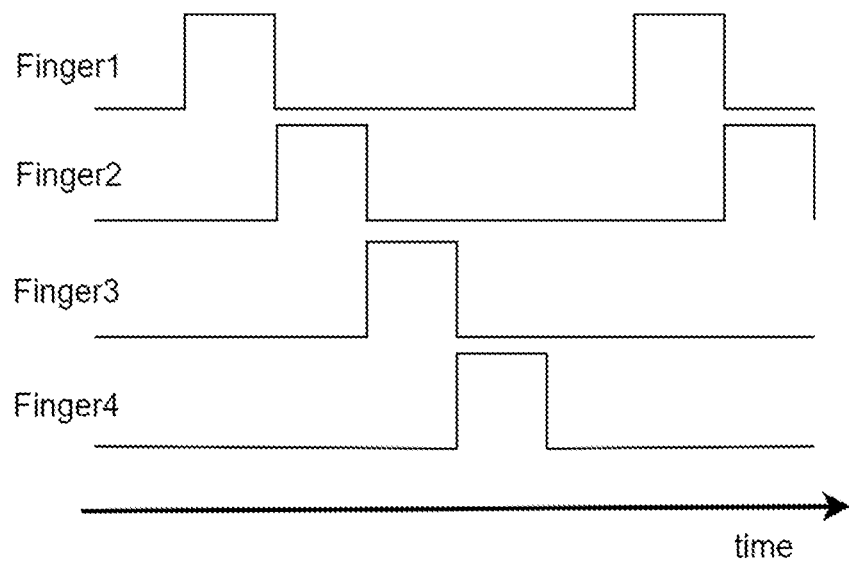
FIG. 12 illustrates a motor pulse sequence of the control method.

Motors typically draw their lowest electrical current when running fastest. The no load speed of a motor is the highest speed it will run at, but as load is increased on the motor in the form of a resistive torque in the drive line, rotation speed reduces and the current draw increases. In reality this means that the grip strength increases as the actuator speed decreases, up to the point that the motors stall. At this condition the motor would draw its highest required current, or stall current. If all the motors are simultaneously operating near their stall current, then this is likely to be higher than may be delivered by the battery system which is typically located inside the limb socket. The stall current of the proposed motors is approximately 2.7 A and the system is capable of delivering a maximum of 5 A but it may be desirable to limit the draw to be around 3.5 A under typical operation. Normal running of the motors must be curtailed before the stall current is reached, and this threshold will depend on the demand of all simultaneously running digits, i.e. the current limit in FIG. 10 is not simply a predefined constant. When the fingers are free moving, the current is low so that the fingers can all move simultaneously, when the total current draw becomes sufficiently high such that the fingers may not be running simultaneously, then the fingers will have stopped moving significantly and the visible effect of the interleaving of the motions (as illustrated in FIG. 12) is essentially masked from the user. FIG. 12 illustrates a pulse sequence that would allow all of the digits to provide their maximum gripping force.

By monitoring the rate at which the electrical current draw increases prior to the current limit being reached it may be possible to determine the stiffness of the object being gripped. For sufficiently soft objects, it may be beneficial to run two or three fingers simultaneously, again running through a sequence to ensure that all digits will attempt to move by the same amount.

This process is only relevant on digit closing. High forces cannot be transmitted to the actuator on opening as the leadscrew nut and slider will merely separate, as described above when detailing each finger assembly 102. If the leadscrew nut velocity, as determined from the movement in the potentiometer, and the pulse rate from the Hall sensor differ then it is likely that this separation has occurred, and a lower electrical current limit could be used to prevent the leadscrew nut driving too firmly against a dead stop.

The actuator control is implemented in an FPGA (Field Programmable Gate Array) which controls the drive to the motors, measures motor speed, motor position from the linear potentiometer, and finger force from the FSR (Force Sensitive Resistor) located on the tip of each digit. The advantage of this system is that multiple instances of the same control circuit can be generated to run in parallel on one device. Because the control system is generated in logic gates as opposed to lines of code running in a software algorithm, the response to changes in force and speed can be much quicker.

According to certain embodiments of the present invention an optional auto-grip function is provided as a user selectable feature and is aptly implemented on a per grip basis. A grip is deemed to have been achieved when all digits have terminated their movement due to having satisfied criteria in terms of position, tip force or motor current limit. The auto grip feature is effectively a per digit operation, and the action largely depends on the reasons for stopping the digit movement. Any digit that stopped its travel due to reaching its target position will remain in place due to the nature of the leadscrew nut preventing back driving or slippage in the system. Load may not be maintained as any reduction in force could only be countered by moving the digit beyond its terminal location. For digits that stop due to motor current limit or satisfying the desired fingertip load then the digit may enter into an automatic grip maintenance cycle, as outlined in FIG. 13. The fingertip load is then monitored and if the load drops then the appropriate motors are activated to try to re-establish the tip force.

Figure 13:
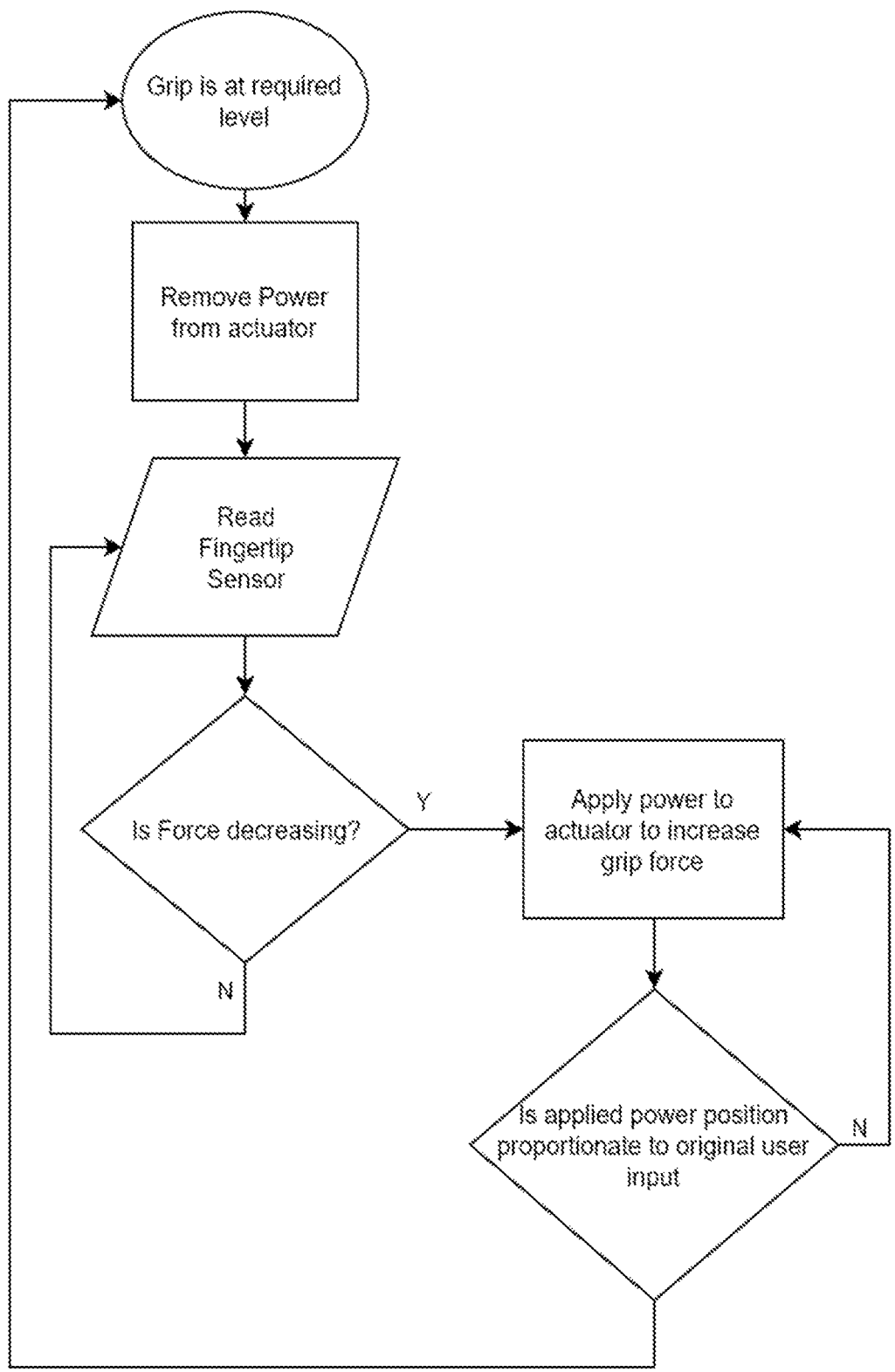
FIG. 13 illustrates a grip maintenance process of the control method.

When the auto-grip function is disabled the power to the digit ceases when either current limit, digit tip force, position or time limit targets have been satisfied. With auto-grip enabled, power to the digits is optionally continued to ensure that a constant grip force is maintained, as shown in FIG. 13.

Certain embodiments of the present invention therefore provide a prosthetic hand having improved functionality and operation. The hand is relatively quick and easy to operate, particularly in terms of selecting a desired grip from a variety of different selectable grips. The hand is configured to maximise the number of different selectable grip configurations and is accurate, consistent, non-complex, and relatively quick to calibrate. The hand is able to produce grip forces similar to that of a 'myo' electrically-controlled terminal device, whilst retaining the dexterity and compliant gripping of a multi-articulated hand. The prosthetic hand has a relatively compact finger and/or thumb drive assembly, and a relatively slim/shallow palm region including a relatively powerful actuator mounted therein and relatively close to the wrist to thereby ensure a centre of gravity of the device is relatively close to the user's body and patient fatigue is reduced. A method of operating a prosthetic hand to select a desired grip from a variety of different grip configurations for the prosthetic hand to adopt for a particular application is also provided. Whilst a prosthetic hand has been described throughout, certain embodiments of the present invention are applicable to other prosthetic terminal devices, such as a prosthetic foot, or a robotic device.

The invention claimed is:

1. Apparatus for supporting a mechanical hand, comprising:
   a support member pivotally coupled at a hinge axis to a mounting member; and
   at least one leaf spring configured to resist movement of the support member about the hinge axis,
   wherein:
      the at least one leaf spring comprises a first leaf spring configured to resist movement of the support member in a first direction about the hinge axis, and a second leaf spring configured to resist movement of the support member in a second direction about the hinge axis, the second direction being opposed to the first direction;
      the at least one leaf spring comprises an elongate main portion coupled to the support member and at least one elongate leg portion extending from the main portion and engageable with the mounting member to provide a reaction force when the support member is forced to move about the hinge axis;
      the at least one elongate leg portion defines a first angle with respect to a plane of the main portion which is around 5-85 degrees; and
      the at least one elongate leg portion is coupled to the main portion by an intermediate portion which defines a second angle with the respect to the plane of the main portion which is greater than the first angle.

2. The apparatus according to claim 1, wherein the at least one leaf spring is configured to urge the support member towards a neutral equilibrium position with respect to the mounting member.

3. The apparatus according to claim 2, wherein each spring is configured such that both the first leaf spring and the second leaf spring engage the mounting member when the support member is in the neutral equilibrium position.

4. The apparatus according to claim 1, wherein the at least one leaf spring comprises a plurality of unconnected layers.

5. The apparatus according to claim 1, wherein the at least one leaf spring is a linear leaf spring.

6. The apparatus according to claim 1, comprising a lock arrangement to lock the support member with respect to the mounting member in a rotational position about the hinge axis.

7. The apparatus according to claim 6, wherein the lock arrangement comprises a locking button to move a locking element to a locked position from an unlocked position, and vice versa.

8. The apparatus according to claim 7, wherein:
   the lock arrangement is configured to move the locking element to and from the locked position by applying a force to the lock button in a first direction, and
   the locking button is urged in a second direction opposed to the first direction by at least one spring.

9. The apparatus according to claim 7, wherein:
the lock arrangement comprises a driving cam member coupled to the locking button, and a driven cam member coupled to the locking element, and
the cam members are configured such that a translation of the driving cam member causes the driven cam member to rotate about a locking axis of the locking element when the cam members are engaged.

10. The apparatus according to claim 9, wherein:
the driving cam member is rotationally constrained by at least one rail element along which the driving cam member is translatable, and
the driven cam member is rotatable about the locking axis with respect to the locking element and rotationally constrainable by the at least one rail element along which the driving cam member is translatable.

11. The apparatus according to claim 10, wherein the at least one rail element comprises a tapered end region for engagement with a cam surface of the driven cam element to rotatably urge the driven cam member about the locking axis when axially urged against the tapered end region.

12. The apparatus according to claim 7, wherein the locking element is selectively engageable with at least one locking aperture when in the locked position.

13. The apparatus according to claim 12, wherein the at least one locking aperture is selectable from a plurality of spaced apart locking apertures each corresponding to a different rotational position of the support member with respect to the mounting member about the hinge axis.

14. The apparatus according to claim 13, wherein the locking apertures extend into an outer edge of at least one lug and the locking element comprises at least one recess for receiving the outer edge of the lug to allow the locking element to pass over the locking apertures when the locking element is in the unlocked position.

15. A mechanical hand comprising apparatus according to claim 1.

16. Apparatus for supporting a mechanical hand, comprising:
a support member pivotally coupled at a hinge axis to a mounting member;
at least one leaf spring configured to resist movement of the support member about the hinge axis; and
a lock arrangement to lock the support member with respect to the mounting member in a rotational position about the hinge axis, the lock arrangement comprising:
a locking button to move a locking element to a locked position from an unlocked position, and vice versa;
a driving cam member coupled to the locking button; and
a driven cam member coupled to the locking element,
wherein the driving and driven cam members are configured such that a translation of the driving cam member causes the driven cam member to rotate about a locking axis of the locking element when the cam members are engaged.

17. The apparatus according to claim 16, wherein:
the driving cam member is rotationally constrained by at least one rail element along which the driving cam member is translatable, and
the driven cam member is rotatable about the locking axis with respect to the locking element and rotationally constrainable by the at least one rail element along which the driving cam member is translatable.

18. The apparatus according to claim 17, wherein the at least one rail element comprises a tapered end region for engagement with a cam surface of the driven cam element to rotatably urge the driven cam member about the locking axis when axially urged against the tapered end region.

19. The apparatus according to claim 16, wherein the locking element is selectively engageable with at least one locking aperture when in the locked position.

20. The apparatus according to claim 19, wherein:
the at least one locking aperture is selectable from a plurality of spaced apart locking apertures each corresponding to a different rotational position of the support member with respect to the mounting member about the hinge axis; and
the locking apertures extend into an outer edge of at least one lug and the locking element comprises at least one recess for receiving the outer edge of the lug to allow the locking element to pass over the locking apertures when the locking element is in the unlocked position.

* * * * *